United States Patent
Plant et al.

(10) Patent No.: US 7,186,722 B2
(45) Date of Patent: Mar. 6, 2007

(54) 2-HETEROARYL-3,4-DIHYDRO-2H-PYRROLE DERIVATIVES AND THE USE THEREOF AS PESTICIDES

(75) Inventors: Andrew Plant, Winnersh (GB); Rüdiger Fischer, Pulheim (DE); Thomas Seitz, Langenfeld (DE); Christoph Erdelen, Leichlingen (DE); Andreas Turberg, Haan (DE); Olaf Hansen, Leichlingen (DE)

(73) Assignee: Bayer Cropscience AG (DE)

( * ) Notice: Subject to any disclaimer, the term of this patent is extended or adjusted under 35 U.S.C. 154(b) by 0 days.

(21) Appl. No.: 10/467,879

(22) PCT Filed: Jan. 31, 2002

(86) PCT No.: PCT/EP02/00992

§ 371 (c)(1),
(2), (4) Date: Jan. 12, 2004

(87) PCT Pub. No.: WO02/064588

PCT Pub. Date: Aug. 22, 2002

(65) Prior Publication Data

US 2004/0116477 A1 Jun. 17, 2004

(30) Foreign Application Priority Data

Feb. 13, 2001 (DE) .................. 101 06 457

(51) Int. Cl.
- *A01N 43/36* (2006.01)
- *C07D 401/04* (2006.01)
- *C07D 407/04* (2006.01)
- *C07D 409/04* (2006.01)
- *C07D 333/22* (2006.01)

(52) U.S. Cl. .................. 514/252.05; 514/255.05; 514/256; 514/343; 514/422; 544/238; 544/333; 544/405; 546/276.4; 546/334; 546/340; 548/517; 548/525; 548/526; 548/527; 549/50; 549/58; 549/77; 549/78

(58) Field of Classification Search .................. 544/238, 544/333, 405; 546/276.4, 334, 340; 548/517, 548/525, 526, 527; 549/50, 58, 77, 78; 514/252.05, 514/255.05, 256, 343, 422

See application file for complete search history.

(56) References Cited

U.S. PATENT DOCUMENTS 6,489,490 B1 * 12/2002 Plant et al. .................. 548/525
6,599,924 B1 * 7/2003 Plant et al. .................. 514/343
6,632,833 B1 * 10/2003 Plant et al. .................. 514/422

FOREIGN PATENT DOCUMENTS

CA 2332522 11/1999
WO 94/29268 12/1994
WO 98/22438 5/1998
WO 00/21958 4/2000

OTHER PUBLICATIONS

Houben-Weyl: Methoden Der Organischen Chemie, 4th edition, pp. 956-975, (date unavailable) Organonitrogen Compounds I, Editor D. Klaman.

Houben-Weyl: Methoden Der Organischen Chemie, 4th edition, pp. 1243-1290, (date unavailable) Organonitrogen Compounds II, Editor D. Klaman.

Tetrahedron: Asymmetry 9, (month unavailable) 1998, pp. 1035-1042, "Novel enantioselective Synthesis of trans-α-(2-carboxycycloprop-1-yl)glycines: conformationally constrained L-glutamate analogues" by A. S. Demir et al.

Tetrahedron Letters 40, (month unavailable) 1999, pp. 4825-4828, "Synthesis of New Pyrrolidine C-Nucleosides via Staudinger-aza-Wittig Cyclization of γ-Azido Ketone" by D. C. Kim et al.

Tetrahedron, vol. 53, No. 10, pp. 3693-3706, (month unavailable) 1997, "Synthesis of 3-Halopyrroles" by N. De Kimpe et al.

Tetrahedron 55, (month unavailable) 1999, pp. 8353-8364, "Synthesis of Nectrisine and Related Compounds, and Their Biological Evaluation" by Y. J. Kim et al.

J. Chem. Soc., Chem. Commun., (month unavailable) 1982, pp. 1224-1225, "A New Efficient Access to Cyclic Imines" by P. H. Lambert et al.

Synthesis, Jan. 1996, pp. 123-132, "Synthesis of Enantiopure 1,2-Didehydropyrrolidine, D-Proline, and Oxazoline Derivatives via Staudinger-Aza-Wittig Cyclization of γ-Azido Aldehydes" by J. Mulzer et al.

Protective Groups in Organic Synthesis, 3rd edition, (month unavailable) 1999, pp. 520-525, by T. W. Greene and P. G. M. Wuts.

J. Org. Chem., vol. 3, No. 24, (month unavailable) 1978, pp. 4593-4596, Biologically Oriented Organic Sulfur Chemistry. 19. Synthesis and Properties of 2-Amino-5-mercapto-5-methylhexanoic Acid, a Bishomologue of Penicillamine. Use of Boron Trifluoride Etherate for Catalyzing Markownikoff Addition of a Thiol to an Olefin[1a-fu] by G. A. Dilbeck et al.

(Continued)

Primary Examiner—Fiona T. Powers
(74) Attorney, Agent, or Firm—Richard E. L. Henderson; Raymond J. Harmuth

(57) ABSTRACT

Novel $\Delta^1$-pyrrolines of the Formula (I)

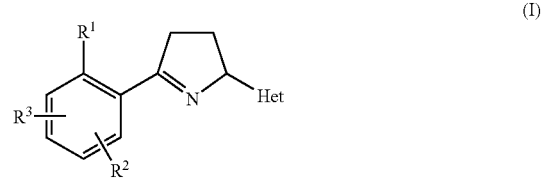

(I)

in which
$R^1$, $R^2$, $R^3$ and Het have the meanings given in the description,
a plurality of processes for preparing these compounds and their use for controlling pests, and also novel intermediates and processes for their preparation.

23 Claims, No Drawings

OTHER PUBLICATIONS

J. Chem. Soc., (month unavailable) 1964, pp. 4142-4145, "793. Cularine and Related Compounds. Part VIII.[1] A Modified Total Synthesis of (±)-Cularine Methiodide.[2]" by T. Kametani et al.

J. Org. Chem., vol. 43, No. 19, (month unavailable 1978, pp. 3711-3713, "Synthesis of L-2-Amino-4-methoxy-*trans*-but-3-enoic Acid" by D. D. Keith et al.

Synthesis, ed. 3, (month unavailable) 1999, pp. 553-555, "Amides".

Tetrahedron Letters, vol. 38, No. 22, pp. 3841-3844, (month unavailable) 1997, "One Pot Biaryl Synthesis *via in situ* Boronate Formation" by A. Giroux et al.

Aust. J. Chem., (month unavailable) 1964, 17, pp. 794-802, "Pyrimidine Reactions VI.* The Amination of Chloropyrimidines With n-Alkylamines" by D. J. Brown et al.

Chem. Ber., 125, (month unavailable) 1992, pp. 1169-1190, "Enantioselective Synthesis of Optically Active Pyridine Derivatives and $C_2$Symmetric 2,2'-Bipyridines" by C. Bolm et al.

Chem. Pharm. Bull., 43(2), pp. 247-255, (month unavailable) 1995, "Studies on Agents with Vasadilator and β-Blocking Activities. II" by T. Seki et al.

Eur. J. Med. Chem., 24, (month unavailable) 1989, pp. 249-258, "Non-basic histamine $H_1$-Antagonists. I. Synthesis and biological evaluation of some substituted 2-(2-pyridylaminoalkylamino) pyrimidones and related compounds" by R. J. Ife et al.

J. Chem. Soc. C, (month unavailable) 1971, pp. 1889-1891, "Pyrimidine Reactions. Part XXII.[1] The Relative Reactivities of Some Corresponding Chloro-, Bromo-, and Iodo-pyrimidines in Aminolysis" by B. W. Arantz et al.

J. Chem. Soc., Perkin Trans. 1, (month unavailable) 1995, pp. 2497-2502, "Ag+ Ion-selective larioat ethers: high pressure syntheses and cation recognition properties" by K. Matsumoto et al.

Org. Prep. Proced Int., (month unavailable) 1993, vol. 25, No. 2, A Practical Procedure for the Synthesis of 5-Substitued γ-Lactams: by Z.Y. Wei et al.

J. Med. Chem., (month unavailable) 1991, 34, pp. 315-319, "Boron-Containing Thiouracil Derivatives for Neutron-Capture Therapy of Melanoma" by W. Tjarks et al.

J. Org. Chem., (month unavailable) 1984, 49, pp. 2240-2245, "Intramolecular Diels-Alder Reactions of 1,2-Diazines: General Indoline Synthesis. Studies on the Preparation of the Central and Right-Hand Segments of CC-1065" by D. L. Boger et al.

J. Org. Chem., (month unavailable) 1990, 55, pp. 69-73, "Lithiation of Methoxypyridines Directed By α-Amino Alkoxides" by D. L. Comins et al.

Organic Preparations And Procedures Int., 30 (4), pp. 433-437, (month unavailable) 1998, "Facile Synthesis Of 5-(Dihydroxyboryl)-2,4-*bis*(Alkoxy)Pyrimidines And N(1)-Substituted 5-(Dihydroxyboryl)uracils" by H. Wojtowicz-Rajchel et al.

Synthesis, No. 7, pp. 1163-1168, (month unavailable) 1999, "Synthesis of Substituted 3-Amino-6-Arylpyridazines via Suzuki Reaction" by Isabelle Parrot et al.

Tetrahedron Letters 40, (month unavailable) 1999, "Resin-bound thiophenols as $S_NAR$-labile linkers: application to the solid phase synthesis of aminopyridazines" by I. Parrot et al.

Tetrahedron Letters, vol. 37, No. 26, pp. 4447-4450, (month unavailable) 1996, "Synthesis of 4-(N-Alkyl-N-Heteroaryl)amino-3,4-Dihydro-3-Hydroxy-2,2-Dimethyl-2H-1-Benzopyran-6-Carbonitrile Derivatives via an Unusual 1,4-Oxygen to Nitrogen Heteroaryl Migration" by C. Z. Ding et al.

Tetrahedron Letters 41, (month unavailable) 2000, pp. 4335-4338, "Selective monolithiation of 2,5-dibromopyridine with butyl-lithium" by X. Wang et al.

J. Org. Chem., (month unavailable) 1995, 60,, pp. 7508-7510, "Palladium(0)-Catalyzed Cross-Coupling Reaction of Alkoxydiboron with Haloarenes: A Direct Procedure for Arylboronic Esters" by T. Ishiyama et al.

Tetrahedron Letters, vol. 38, No. 19, pp. 3447-3450, (month unavailable) 1997, "Synthesis of Arylboronates *via* the Palladium(0)-Catalyzed Cross-Coupling Reaction of Tetra(alkoxo)diborons With Aryl Triflates" by T. Ishiyama et al.

Tetrahedron Letters, vol. 36, No. 50, pp. 9085-9088, (month unavailable) 1995, "Selectivity in Palladium(0)-Catalyzed Cross-Coupling Reactions: Application to a Tandem Stille Reaction." by S. A. Hitchcock et al.

Appl Microbiol Biotechnol, (month unavailable) 1997, 47: pp. 650-657, "Isolation and Characterization of highly (R)-specific N-acetyl-1-phenylethylamine amidohydrolase, a new enzyme from *Arthrobacter aurescens* AcR5b" by M. Graf et al.

Chem. Ind., 37, (month unavailable) 1985, pp. 730-732, "Schiffsfarben—eine Spezialität der Seenahen Lackindustrie" by H. R. Ungerer.

Tetrahedron Letters 39, (month unavailable) 1998, pp. 2705-2706, "A Novel Protecting Group For Hindered Phenols" by M. M. Hansen et al.

Tetrahedron, vol. 32, pp. 1571-1573, (month unavailable) 1976, "A New Synthesis of N-Acyl Aromatic α-Amino Acids-Amidoalklyation of Aromatic And Heterocyclic Compounds With Glyoxylic Acid Derivatives[1]" by D. Ben-Ishai et al.

J. Org. Chem., (month unavailable) 1991, 56, pp. 1822-1827, "Organometallic Reactions of ω-Heterosubstituted *N*-Acyl Lactams. A New Route to γ- Keto Aldehydes from 5- Ethoxy-2-pyrrolidinone" by D. Savoia et al.

Synthesis, Apr. 1980, pp. 315-317, "Eine einfache Herstellung von (o-Alkoxylactamen durch anodische Alkoxylierung" by M. Mitzlaff et al.

Gregor Wille et al, "Short Synthesis of the Bacterial Pigments Violacein and Deoxyviolacein", Synthesis, 5, Jan. 2001, pp. 759-762, XP002201463.

* cited by examiner

2-HETEROARYL-3,4-DIHYDRO-2H-PYRROLE DERIVATIVES AND THE USE THEREOF AS PESTICIDES

The present invention relates to novel $\Delta^1$-pyrrolines, to a plurality of processes for their preparation and to their use as pesticides.

It is already known that numerous $\Delta^1$-pyrrolines have insecticidal properties (cf. WO 00/21958, WO 99/59968, WO 99/59967 and WO 98/22438). The activity of these substances is good; however, in some cases it is unsatisfactory.

This invention now provides $\Delta^1$-pyrrolines of the formula (I),

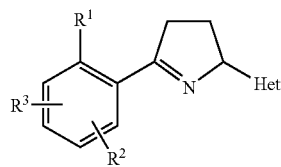

in which
$R^1$ represents halogen, in each case optionally substituted alkyl, alkoxy or —S(O)$_w$R$^4$,
$R^2$ and $R^3$ independently of one another represent hydrogen, halogen or in each case optionally substituted alkyl, alkoxy or alkoxyalkyl,
$R^4$ represents optionally substituted alkyl,
Het represents heteroaryl which is optionally mono- or polysubstituted by identical or different $R^5$,
$R^5$ represents the grouping —X—Y-Z-E with the proviso that Y does not represent a direct bond if X does not represent a direct bond,
X represents a direct bond, oxygen, —S(O)$_w$—, —NR$^6$—, carbonyl, carbonyloxy, oxycarbonyl, oxysulphonyl (OSO$_2$), alkylene, halogenalkylene, alkenylene, halogenoalkenylene, alkinylene, alkyleneoxy, oxyalkylene, oxyalkyleneoxy, —S(O)$_w$-alkylene, cyclopropylene or oxiranylene,
Y represents a direct bond or represents in each case optionally substituted phenylene, naphthylene, tetrahydronaphthylene or heterocyclylene,
Z represents a direct bond or —(CH$_2$)$_n$—,
E represents hydrogen, halogen, hydroxyl, cyano, formyl, nitro, trialkylsilyl, pentafluorothio, —S(O)$_w$R$^7$, —OSO$_2$R$^7$, —NR$^8$R$^9$, —COR$^7$, —CO$_2$R$^7$, —OC(O)R$^7$, —CONR$^{10}$R$^{11}$, —N(R$^{12}$)COR$^{13}$, —C(R$^{14}$)=N—OR$^{15}$, —SO$_2$NR$^{16}$R$^{17}$; represents in each case optionally substituted alkyl, alkenyl, alkinyl, alkoxy, alkenyloxy, cycloalkyl, cycloalkylalkyl, cycloalkyloxy, aryl, arylalkyl, aryloxy, aryloxyalkyl, saturated or unsaturated heterocyclyl or heterocyclylalkyl,
$R^6$ represents in each case optionally substituted alkyl, cycloalkyl, cycloalkylalkyl, aryl or arylalkyl,
$R^7$ represents in each case optionally substituted alkyl, cycloalkyl, aryl or arylalkyl,
$R^8$ and $R^9$ independently of one another represent hydrogen, —SO$_2$R$^7$, —COR$^7$, —CO$_2$R$^7$, represent in each case optionally substituted alkyl, alkenyl, cycloalkyl, cycloalkylalkyl, aryl, arylalkyl or saturated or unsaturated heterocyclyl or heterocyclylalkyl,
$R^8$ and $R^9$ furthermore together represent in each case optionally substituted alkenylene or alkylene, where the alkylene chain may in each case be interrupted by —O—, —S— or —NR$^{18}$—,
$R^{10}$ and $R^{11}$ independently of one another represent hydrogen, —SO$_2$R$^7$, represent in each case optionally substituted alkyl, alkenyl, cycloalkyl, cycloalkylalkyl; aryl, arylalkyl or saturated or unsaturated heterocyclyl or heterocyclylalkyl,
$R^{10}$ and $R^{11}$ furthermore together represent optionally substituted alkylene, where the alkylene chain may in each case be interrupted by —O—, —S— or —NR$^{18}$—,
$R^{12}$ and $R^{13}$ independently of one another represent hydrogen, represent in each case optionally substituted alkyl, cycloalkyl, cycloalkylalkyl, aryl or arylalkyl,
$R^{12}$ and $R^{13}$ furthermore together represent in each case optionally substituted alkylene or alkenylene,
$R^{14}$ and $R^{15}$ independently of one another represent hydrogen, represent in each case optionally substituted alkyl or alkenyl,
$R^{16}$ and $R^{17}$ independently of one another represent hydrogen, represent optionally substituted alkyl or cycloalkyl,
$R^{16}$ and $R^{17}$ furthermore together represent optionally substituted alkylene, alkoxyalkylene or alkylthioalkylene,
$R^{18}$ represents hydrogen, —SO$_2$R$^7$, —COR$^7$ or —CO$_2$R$^7$; represents in each case optionally substituted alkyl, alkenyl, cycloalkyl, cycloalkylalkyl, aryl, arylalkyl or saturated or unsaturated heterocyclyl or heterocyclylalkyl,
w represents 0, 1 or 2,
n represents 1, 2, 3 or 4.

Depending on the nature and number of substituents, the compounds of the formula (I) can, if appropriate, be present as geometrical and/or optical isomers, regioisomers and/or configurational isomers or isomer mixtures thereof of varying composition. What is claimed by the invention are both the pure isomers and the isomer mixtures.

Furthermore, it has been found that the novel compounds of the formula (I) can be obtained by one of the processes described below.

$\Delta^1$-Pyrrolines of the formula (I)

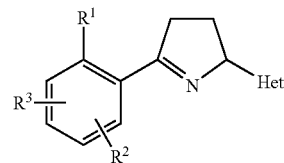

in which
$R^1$, $R^2$, $R^3$ and Het have the meanings given above
can be prepared by
A) treating amino ketones of the formula (II)

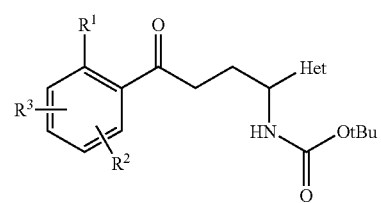

in which

R¹, R², R³ and Het have the meanings given above with a Lewis acid or a protonic acid, if appropriate in the presence of a diluent, or B) reacting azides of the formula (III)

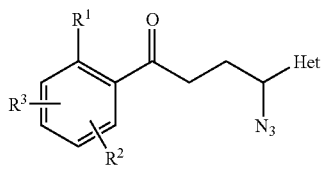
(III)

in which

R¹, R², R³ and Het have the meanings given above with a trialkylphosphine or a triarylphosphine or a trialkyl phosphite or a reducing agent in the presence of a diluent and, if appropriate, in the presence of a catalyst, or C) reacting amides of the formula (IV)

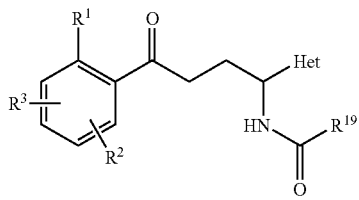
(IV)

in which

R¹⁹ represents alkyl, halogenoalkyl, aryl or arylalkyl and

R¹, R², R³ and Het have the meanings given above with an N-deacetylating agent, if appropriate in the presence of a diluent.

Δ¹-Pyrrolines of the formula (I-a)

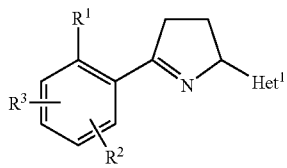
(I-a)

in which

Het¹ represents heteroaryl which is monosubstituted by $R^{5-1}$, $R^{5-1}$ represents the grouping —Y¹-E, Y¹ represents in each case optionally substituted phenylene or heterocyclylene, R¹, R², R³ and E have the meanings given above can be prepared by D) reacting Δ¹-pyrrolines of the formula (I-b)

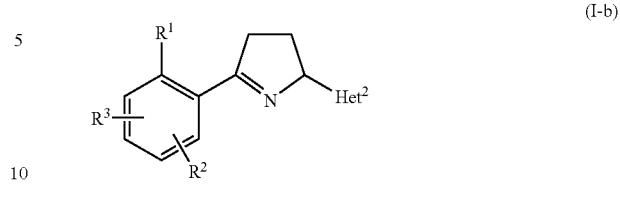
(I-b)

in which

Het² represents heteroaryl which is monosubstituted by $R^{5-2}$, $R^{5-2}$ represents chlorine, bromine, iodine, —OSO₂CF₃ or —OSO₂(CF₂)₃CF₃ and R¹, R² and R³ have the meanings given above with (hetero)cycles of the formula (V)

A¹-Y¹-E     (V)

in which

Y¹ and E have the meanings given above and

A¹ represents chlorine, bromine, iodine, —OSO₂CF₃ or —OSO₂(CF₂)₃CF₃, in the presence of a catalyst, in the presence of a diboronic ester and, if appropriate, in the presence of an acid binder and, if appropriate, in the presence of a diluent, in a tandem reaction, or E) reacting Δ¹-pyrrolines of the formula (VI)

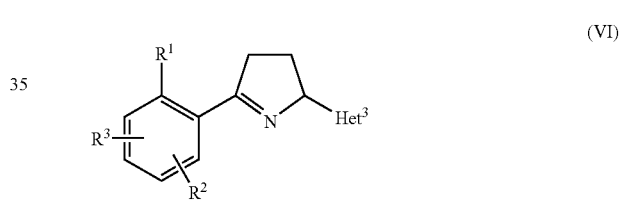
(VI)

in which

Het³ represents heteroaryl which is monosubstituted by A²,

A² represents —B(OH)₂, (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxaborol-2-yl and R¹, R² and R³ have the meanings given above with heterocycles of the formula (V)

A¹-Y¹-E     (V)

in which

Y¹, E and A¹ have the meanings given above in the presence of a catalyst, if appropriate in the presence of an acid binder and if appropriate in the presence of a diluent, or F) reacting Δ¹-pyrrolines of the formula (I-b)

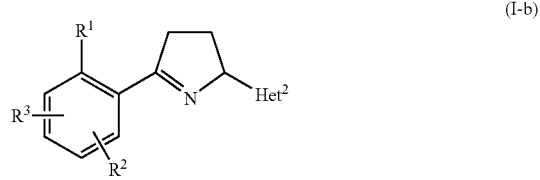
(I-b)

in which

R¹, R², R³ and Het² have the meanings given above with boronic acid derivatives of the formula (VII)

$$A^2\text{-}Y^1\text{-}E \quad (II)$$

in which

Y¹, E and A² have the meanings given above in the presence of a catalyst, if appropriate in the presence of an acid binder and if appropriate in the presence of a diluent, or G) reacting Δ¹-pyrrolines of the formula (I-c)

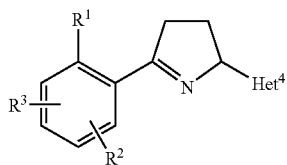

(I-c)

in which

Het⁴ represents heteroaryl which is monosubstituted by R⁵⁻³,

R⁵⁻³ represents bromine or iodine and

R¹, R² and R³ have the meanings given above with organometallic compounds of the formula (VIII)

$$M\text{-}Y^1\text{-}E \quad (VIII)$$

in which

Y¹ and E have the meanings given above and

M represents ZnCl, Sn(Me)₃ or Sn(n-Bu)₃, in the presence of a catalyst, if appropriate in the presence of an acid binder and if appropriate in the presence of a diluent.

Finally, it has been found that the compounds of the formula (I) according to the invention have very good insecticidal properties and can be used both in crop protection and in the protection of materials for controlling, undesirable pests, such as insects.

The formula (I) provides a general definition of the Δ¹-pyrrolines according to the invention.

R¹ preferably represents halogen, alkyl, halogenoalkyl, alkoxy, halogenoalkoxy or —S(O)$_w$R⁴.

R² and R³ independently of one another preferably represent hydrogen, halogen, alkyl, halogenoalkyl, alkoxy, halogenoalkoxy or alkoxyalkyl.

R⁴ preferably represents alkyl or halogenoalkyl.

Het preferably represents 5- to 14-membered heteroaryl which comprises 1 to 3 aromatic rings and one or more heteroatoms from the group consisting of nitrogen, oxygen and sulphur and is optionally mono- to tetrasubstituted by identical or different R⁵.

R⁵ preferably represents the grouping —X—Y-Z-E, with the proviso that Y does not represent a direct bond if X does not represent a direct bond.

X preferably represents a direct bond, oxygen, —S(O)$_w$—, —NR⁶—, carbonyl, carbonyloxy, oxycarbonyl, oxysulphonyl (OSO₂), alkylene, halogenoalkylene, alkenylene, halogenoalkenylene, alkinylene, alkyleneoxy, oxyalkylene, oxyalkyleneoxy, —S(O)$_w$-alkylene, cyclopropylene or oxiranylene.

Y preferably represents a direct bond or represents phenylene, naphthylene, tetrahydronaphthylene or 5- to 10-membered saturated or unsaturated heterocyclylene having one or more heteroatoms from the group consisting of nitrogen, oxygen and sulphur, each of which radicals is optionally mono- to tetrasubstituted by identical or different radicals from the list W¹.

Z preferably represents a direct bond or —(CH₂)$_n$—.

E preferably represents hydrogen, halogen, hydroxyl, cyano, formyl, nitro, trialkylsilyl, pentafluorothio, —S(O)$_w$R⁷, —OSO₂R⁷, —NR⁸R⁹, —COR⁷, —CO₂R⁷, —OC(O)R⁷, —CONR¹⁰R¹¹, —N(R¹²)COR¹³, —C(R¹⁴)=N—OR¹⁵, —SO₂NR¹⁶R¹⁷; represents alkyl, alkenyl, alkinyl, alkoxy, alkenyloxy, each of which is optionally mono- or polysubstituted by identical or different substituents from, the group consisting of halogen, cyano, alkoxy and/or —NR⁸R⁹; or represents cycloalkyl, cycloalkylalkyl, cycloalkyloxy, aryl, arylalkyl, aryloxy, aryloxyalkyl, saturated or unsaturated 5- to 10-membered heterocyclyl or heterocyclylalkyl having one or more heteroatoms from the group consisting of nitrogen, oxygen and sulphur, each of which radicals is optionally mono- or polysubstituted by identical or different substituents from the group consisting of halogen, cyano, nitro, alkyl, halogenoalkyl, alkenyl, halogenoalkenyl, alkoxy, halogenoalkoxy, alkylthio and halogenoalkylthio.

W¹ preferably represents halogen, cyano, formyl, nitro, trialkylsilyl, alkyl, halogenoalkyl, alkoxy, halogenoalkoxy, alkenyl, halogenoalkenyl, alkenyloxy, halogenoalkenyloxy, alkylcaronyl, alkoxycarbonyl, —S(O)$_w$R⁷, —C(R¹⁴)=N—OR¹⁵, —SO₂NR¹⁶R¹⁷, —(CH₂)$_p$NR¹⁶R¹⁷, —(CH₂)$_p$N(R¹⁶)COR¹⁷, —(CH₂)$_p$N(R¹⁶)SO₂R¹⁷, —OSO₂R¹⁶, —OSO₂NR¹⁶R¹⁷.

R⁶ preferably represents alkyl, halogenoalkyl or represents cycloalkyl, cycloalkylalkyl, aryl or arylalkyl, each of which is optionally mono- or polysubstituted by identical or different substituents from the group consisting of halogen, alkyl, halogenoalkyl, alkoxy, halogenoalkoxy, alkylthio and/or halogenoalkylthio.

R⁷ preferably represents alkyl which is optionally mono- or polysubstituted by identical or different substituents from the group consisting of halogen and —NR⁸R⁹, represents cycloalkyl, aryl or arylalkyl, each of which is optionally mono- or polysubstituted by identical or different substituents from the group consisting of halogen, cyano, alkyl, halogenoalkyl, alkoxy, halogenoalkoxy, alkylthio and halogenoalkylthio.

R⁸ and R⁹ independently of one another preferably represent hydrogen, —SO₂R⁷, —COR⁷, —CO₂R⁷, represent alkyl or alkenyl, each of which is optionally mono- or polysubstituted by identical or different substituents from the group consisting of halogen, alkylcarbonyl, alkylcarbonyloxy, alkylamino, dialkylamino, alkoxy, halogenoalkoxy, alkylthio and halogenoalkylthio; represents cycloalkyl, cycloalkylalkyl, aryl, arylalkyl or saturated or unsaturated 5- to 10-membered heterocyclyl or heterocyclylalkyl having one or more heteroatoms from the group consisting of nitrogen, oxygen and sulphur, each of which radicals is optionally mono- or polysubstituted by identical or different substituents from the group consisting of halogen, cyano, alkyl, halogenoalkyl, alkoxy, halogenoalkoxy, alkylthio and halogenoalkylthio.

R⁸ and R⁹ furthermore together preferably represent alkenylene which is optionally mono- or polysubstituted by identical or different substituents from the group consisting of halogen, cyano, alkoxy, halogenoalkoxy, alkylthio and halogenoalkylthio or represent alkylene which is optionally mono- or polysubstituted by identical or different substituents from the group consisting of halogen, cyano, alkyl, halogenoalkyl, alkoxy, halogenoalkoxy, alkylthio and halogenoalkylthio, where the alkylene chain may in each case be interrupted by —O—, —S— or —NR$^{18}$—.

R$^{10}$ and R$^{11}$ independently of one another preferably represent hydrogen, —SO$_2$R$^7$, represent alkyl or alkenyl, each of which is optionally mono- or polysubstituted by identical or different substituents from the group consisting of halogen, alkylamino, dialkylamino, alkoxy and alkylthio; represent cycloalkyl, cycloalkylalkyl, aryl, arylalkyl or saturated or unsaturated 5- to 10-membered heterocyclyl or heterocyclylalkyl having one or more heteroatoms from the group consisting of nitrogen; oxygen and sulphur, each of which radicals is optionally mono- or polysubstituted by identical or different substituents from the group consisting of halogen, cyano, alkyl, halogenoalkyl, alkoxy, halogenoalkoxy, alkylthio and halogenoalkylthio.

R$^{10}$ and R$^{11}$ furthermore together preferably represent alkylene which is optionally mono- or polysubstituted by identical or different substituents from the group consisting of halogen, cyano, alkyl, halogenoalkyl, alkoxy, halogenoalkoxy, alkylthio and halogenoalkylthio, where the alkylene chain may in each case be interrupted by —O—, —S— or —NR$^{18}$—.

R$^{12}$ and R$^{13}$ independently of one another preferably represent hydrogen, represent alkyl which is optionally mono- or polysubstituted by identical or different substituents from the group consisting of cyano, alkoxy and alkylthio, represent cycloalkyl, cycloalkylalkyl, aryl or arylalkyl, each of which is optionally mono- or polysubstituted by identical or different substituents from the group consisting of halogen, cyano, alkyl, halogenoalkyl, alkoxy, halogenoalkoxy, alkylthio and halogenoalkylthio.

R$^{12}$ and R$^{13}$ furthermore together preferably represent alkylene or alkenylene, each of which is optionally mono- or polysubstituted by identical or different substituents from the group consisting of halogen, alkyl, halogenoalkyl, alkoxy, halogenoalkoxy, alkylthio and halogenoalkylthio.

R$^{14}$ and R$^{15}$ independently of one another preferably represent hydrogen, represent alkyl, halogenoalkyl, alkenyl or halogenoalkenyl.

R$^{16}$ and R$^{17}$ independently of one another preferably represent hydrogen) alkyl, halogenoalkyl or represent cycloalkyl which is optionally mono- or polysubstituted by identical or different substituents from the group consisting of halogen and alkyl.

R$^{16}$ and R$^{17}$ furthermore together preferably represent alkylene, alkoxyalkylene or alkylthioalkylene, each of which is optionally mono- or polysubstituted by identical or different substituents from the group consisting of halogen and alkyl.

R$^{18}$ preferably represents hydrogen, —SO$_2$R$^7$, —COR$^7$ or —CO$_2$R$^7$; represents alkyl or alkenyl, each of which is optionally mono- or polysubstituted by identical or different substituents from the group consisting of halogen, cyano, alkylamino, dialkylamino, alkoxy, halogenoalkoxy, alkylthio and halogenalkylthio; represents cycloalkyl, cycloalkylalkyl, aryl, arylalkyl, saturated or unsaturated 5- to 10-membered heterocyclyl or heterocyclylalkyl having one or more heteroatoms from the group consisting of nitrogen, oxygen and sulphur, each of which radicals is optionally mono- or polysubstituted by identical or different substituents from the group consisting of halogen, cyano, alkyl, halogenoalkyl, alkoxy, halogenoalkoxy, alkylthio and halogenoalkylthio.

w preferably represents 0, 1 or 2.

n preferably represents 1, 2, 3 or 4.

p preferably represents 0, 1 or 2.

R$^1$ particularly preferably represents halogen, C$_1$–C$_6$-alkyl, C$_1$–C$_6$-halogenoalkyl, C$_1$–C$_6$-alkoxy, C$_1$–C$_6$-halogenoalkoxy or —S(O)$_w$R$^4$.

R$^2$ and R$^3$ independently of one another particularly preferably represent hydrogen, halogen, C$_1$–C$_6$-alkyl, C$_1$–C$_6$-halogenoalkyl, C$_1$–C$_6$-alkoxy, C$_1$–C$_6$-halogenoalkoxy or C$_1$–C$_6$-alkoxy-C$_1$–C$_6$-alkyl.

R$^4$ particularly preferably represents C$_1$–C$_6$-alkyl or C$_1$–C$_6$-halogenoalkyl.

Het particularly preferably represents 5- to 14-membered heteroaryl which comprises 1 to 3 aromatic rings and 1 to 4 heteroatoms including 0 to 4 nitrogen atoms, 0 to 2 nonadjacent oxygen atoms and/or 0 to 2 nonadjacent sulphur atoms (in particular thienyl, benzothienyl, furyl, benzofuryl, indolyl, thienothienyl, thienofuryl, thienobenzothienyl, thienobenzofuryl, pyridinyl, pyrimidinyl, pyridazinyl, pyrazinyl, triazolyl or tetrazolyl), each of which radicals is optionally mono- to tetrasubstituted by identical or different R$^5$.

R$^5$ particularly preferably represents the grouping —X—Y-Z-E, with the proviso that Y does not represent a direct bond if X does not represent a direct bond.

X particularly preferably represents a direct bond, oxygen, —S(O)$_w$—, —NR$^6$—, carbonyl, carbonyloxy, oxycarbonyl, oxysulphonyl (OSO$_2$), C$_1$–C$_6$-alkylene, C$_1$–C$_6$-halogenoalkylene, C$_2$–C$_6$-alkenylene, C$_2$–C$_6$-halogenoalkenylene, C$_2$–C$_6$-alkinylene, C$_1$–C$_6$-alkyleneoxy, C$_1$–C$_6$-oxyalkylene, oxy-C$_1$–C$_6$-alkyleneoxy, —S(O)$_w$—C$_1$–C$_6$-alkylene, cyclopropylene or oxiranylene.

Y particularly preferably represents a direct bond or represents 1,4-phenylene, 1,3-phenylene, 1,2-phenylene, 2,6-naphthylene, 2,7-naphthylene, 1,4-naphthylene, 2,6-(1,2,3,4-tetrahydro)naphthylene, 2,7-(1,2,3,4-tetrahydro)naphthylene, 1,4-(1,2,3,4-tetrahydro)naphthylene, 5,8-(1,2,3,4-tetrahydro)naphthylene, each of which is optionally mono- to tetrasubstituted by identical or different radicals from the list W$^1$; or represents 5- or 6-membered saturated or unsaturated heterocyclylene which comprises 1 to 3 heteroatoms including 0 to 3 nitrogen atoms, 0 to 2 nonadjacent oxygen atoms and/or 0 to 2 nonadjacent sulphur atoms (in particular furylene, thienylene, pyrrolylene, oxazolylene, thiazolylene, pyridinylene, pyrimidinylene, pyridazinylene or pyrazinylene), each of which radicals is optionally mono- to tetrasubstituted by identical or different radicals from the list W$^1$.

Z particularly preferably represents a direct bond or —(CH$_2$)$_n$—.

E particularly preferably represents hydrogen, fluorine, chlorine, bromine, hydroxyl, cyano, formyl, nitro, tri-(C$_1$–C$_6$-alkyl)silyl, pentafluorothio, —S(O)$_w$R$^7$, —OSO$_2$R$^7$, —NR$^8$R$^9$, —COR$^7$, —CO$_2$R$^7$, —OC(O)R$^7$, —CONR$^{10}$R$^{11}$, —N(R$^{12}$)COR$^{13}$, —C(R$^{14}$)=N—OR$^{15}$, —SO$_2$NR$^{16}$R$^{17}$; represents C$_1$–C$_{20}$-alkyl, C$_2$–C$_{20}$-alkenyl, C$_2$–C$_{10}$-alkinyl, C$_1$–C$_{20}$-alkoxy, C$_2$–C$_{20}$-alkenyloxy, each of which is optionally mono- or polysubstituted by identical or different radicals from the group consisting of halogen, cyano, C$_1$–C$_{10}$-alkoxy and —NR$^8$R$^9$; or represents C$_3$–C$_{12}$-cycloalkyl, C$_3$–C$_7$-cycloalkyl-C$_1$–C$_4$-alkyl, C$_3$–C$_{12}$-cycloalkyloxy, aryl, aryl-C$_1$–C$_4$-alkyl, aryloxy, aryloxy-C$_1$–C$_4$-alkyl, saturated or unsaturated 5- to 10-membered heterocyclyl or heterocyclyl-C$_1$–C$_4$-alkyl which comprises 1 to 4 heteroatoms including 0 to 4 nitrogen atoms, 0 to 2 nonadjacent oxygen atoms and/or 0 to 2 nonadjacent sulphur atoms (in particular tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, piperidino, morpholinyl, thiomorpholinyl, morpholino, thiomorpholino, triazinyl, triazolyl, quinolinyl or isoquinolinyl), each of which radicals is optionally mono- to tetrasubstituted by identical or different substituents from the group consisting of halogen, cyano, nitro, $C_1$–$C_6$-alkyl, $C_1$–$C_6$-halogenoalkyl, $C_2$–$C_6$-alkenyl, $C_2$–$C_6$-halogenoalkenyl, $C_1$–$C_6$-alkoxy, $C_1$–$C_6$-halogenoalkoxy, $C_1$–$C_6$-alkylthio and $C_1$–$C_6$-halogenoalkylthio.

$W^1$ particularly preferably represents fluorine, chlorine, bromine, cyano, formyl, nitro, tri-($C_1$–$C_6$-alkyl)silyl, $C_1$–$C_6$-alkyl, $C_1$–$C_6$-halogenoalkyl, $C_1$–$C_6$-alkoxy, $C_1$–$C_6$-halogenoalkoxy, $C_2$–$C_6$-alkenyl, $C_2$–$C_6$-halogenoalkenyl, $C_2$–$C_6$-alkenyloxy, $C_2$–$C_6$-halogenoalkenyloxy, $C_1$–$C_6$-alkylcarbonyl, $C_1$–$C_6$-alkoxycarbonyl, —S(O)$_w$R$^7$, —C(R$^{14}$)=N—OR$^{15}$, —SO$_2$NR$^{16}$R$^{17}$, —(CH$_2$)$_p$NR$^{16}$R$^{17}$, —(CH$_2$)$_p$N(R$^{16}$)COR$^{17}$, —(CH$_2$)$_p$N(R$^{16}$)SO$_2$R$^{17}$, —OSO$_2$R$^{16}$, —OSO$_2$NR$^{16}$R$^{17}$.

$R^6$ particularly preferably represents $C_1$–$C_6$-alkyl, $C_1$–$C_6$-halogenoalkyl or represents $C_3$–$C_7$-cycloalkyl, $C_3$–$C_6$-cycloalkyl-$C_1$–$C_4$-alkyl, aryl or aryl-$C_1$–$C_4$-alkyl, each of which is optionally mono- to tetrasubstituted by halogen, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

$R^7$ particularly preferably represents $C_1$–$C_{20}$-alkyl which is optionally mono- or polysubstituted by identical or different substituents from the group consisting of halogen and —NR$^8$R$^9$, represents $C_3$–$C_6$-cycloalkyl, aryl or aryl-$C_1$–$C_4$-alkyl, each of which is optionally mono- to octasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

$R^8$ and $R^9$ independently of one another particularly preferably represent hydrogen, —SO$_2$R$^7$, —COR$^7$, —CO$_2$R$^7$, represent $C_1$–$C_{20}$-alkyl or $C_2$–$C_{20}$-alkenyl, each of which is optionally mono- or polysubstituted by identical or different substituents from the group consisting of halogen, $C_1$–$C_6$-alkylcarbonyl, $C_1$–$C_6$-alkylcarbonyloxy, $C_1$–$C_6$-alkylamino, di-($C_1$–$C_6$-alkyl)amino, $C_1$–$C_6$-alkoxy, $C_1$–$C_6$-halogenoalkoxy, $C_1$–$C_6$-alkylthio, $C_1$–$C_6$-halogenoalkylthio; represent $C_3$–$C_{12}$-cycloalkyl, $C_3$–$C_7$-cycloalkyl-$C_1$–$C_4$-alkyl, aryl, aryl-$C_1$–$C_4$-alkyl or saturated or unsaturated 5- to 10-membered heterocyclyl or heterocyclyl-$C_1$–$C_4$-alkyl which comprises 1 to 4 heteroatoms including 0 to 4 nitrogen atoms, 0 to 2 nonadjacent oxygen atoms and/or 0 to 2 nonadjacent sulphur atoms (in particular tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl), each of which radicals is optionally mono- to tetrasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio or $C_1$–$C_6$-halogenoalkylthio.

$R^8$ and $R^9$ furthermore together particularly preferably represent $C_2$–$C_{12}$-alkenylene which is optionally mono- or polysubstituted by identical or different substituents from the group consisting of halogen, cyano, $C_1$–$C_6$-alkoxy, $C_1$–$C_6$-halogenoalkoxy, $C_1$–$C_6$-alkylthio and $C_1$–$C_6$-halogenoalkylthio or represent $C_3$–$C_{12}$-alkylene which is optionally mono- or polysubstituted in the alkylene moiety by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio, where the alkylene chain may in each case be interrupted by —O—, —S— or —NR$^8$—.

$R^{10}$ and $R^{11}$ independently of one another particularly preferably represent hydrogen, —SO$_2$R$^7$, represent $C_1$–$C_6$-alkyl or $C_2$–$C_6$-alkenyl, each of which is optionally mono- to tridecasubstituted by identical or different substituents from the group consisting of halogen, $C_1$–$C_6$-alkylamino, di-($C_1$–$C_6$-alkyl)amino, $C_1$–$C_6$-alkoxy, $C_1$–$C_6$-halogenoalkoxy, $C_1$–$C_6$-alkylthio and $C_1$–$C_6$-halogenoalkylthio; represent $C_3$–$C_7$-cycloalkyl, $C_3$–$C_7$-cycloalkyl-$C_1$–$C_4$-alkyl, aryl, aryl-$C_1$–$C_4$-alkyl or saturated or unsaturated 5- to 10-membered heterocyclyl or heterocyclyl-$C_1$–$C_4$-alkyl which comprises 1 to 4 heteroatoms including 0 to 4 nitrogen atoms, 0 to 2 nonadjacent oxygen atoms and/or 0 to 2 nonadjacent sulphur atoms (in particular tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl), each of which radicals is optionally mono- to tetrasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

$R^{10}$ and $R^{11}$ furthermore together particularly preferable represent $C_3$–$C_6$-alkylene, —(CH$_2$)$_2$—O—(CH$_2$)$_2$—, —(CH$_2$)$_2$—S—(CH$_2$)$_2$— or —(CH$_2$)$_2$—N(R$^{18}$)—(CH$_2$)$_2$—, each of which is optionally mono- to tetrasubstituted in the alkylene moiety by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

$R^{12}$ and $R^{13}$ independently of one another particularly preferably represent hydrogen, represent $C_1$–$C_6$-alkyl which is optionally mono- to tridecasubstituted by identical or different substituents from the group consisting of halogen, cyano, $C_1$–$C_6$-alkoxy and $C_1$–$C_6$-alkylthio, represent $C_3$–$C_7$-cycloalkyl, $C_3$–$C_7$-cycloalkyl-$C_1$–$C_4$-alkyl, aryl or aryl-$C_1$–$C_4$-alkyl, each of which is optionally mono- to octasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

$R^{12}$ and $R^{13}$ furthermore together particularly preferably represent $C_3$–$C_{10}$-alkylene or $C_3$–$C_{10}$-alkenylene, each of which is optionally mono- to octasubstituted by identical or different substituents from the group consisting of halogen, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

$R^{14}$ and $R^{15}$ independently of one another particularly-preferably represent hydrogen, represent $C_1$–$C_6$-alkyl, $C_1$–$C_6$-halogenoalkyl, $C_2$–$C_6$-alkenyl or $C_2$–$C_6$-halogenoalkenyl.

$R^{16}$ and $R^{17}$ independently of one another particularly preferably represent hydrogen, $C_1$–$C_6$-alkyl, $C_1$–$C_6$-halogenoalkyl or represent $C_3$–$C_7$-cycloalkyl which is optionally mono- to octasubstituted by identical or different substituents from the group consisting of fluorine, chlorine, bromine and/or $C_1$–$C_6$-alkyl.

$R^{16}$ and $R^{17}$ furthermore together particularly preferably represent $C_3$–$C_6$-alkylene, $C_1$–$C_3$-alkoxy-$C_1$–$C_3$-alkylene or $C_1$–$C_3$-alkylthio-$C_1$–$C_3$-alkylene, each of which is optionally mono- to nonasubstituted by identical or different substituents from the group consisting of fluorine, chlorine, bromine and $C_1$–$C_6$-alkyl.

$R^{18}$ particularly preferably represents hydrogen, —$SO_2R^7$, —$COR^7$ or —$CO_2R^7$; represents $C_1$–$C_{20}$-alkyl or $C_2$–$C_{20}$-alkenyl, each of which is optionally mono- or polysubstituted by identical or different substituents from the group consisting of halogen, cyano, $C_1$–$C_6$-alkylamino, di-($C_1$–$C_6$-alkyl)amino, $C_1$–$C_6$-alkoxy, $C_1$–$C_6$-halogenoalkoxy, $C_1$–$C_6$-alkylthio and $C_1$–$C_6$-halogenoalkylthio; represents $C_3$–$C_{12}$-cycloalkyl, $C_3$–$C_7$-cycloalkyl-$C_1$–$C_4$-alkyl, aryl, aryl-$C_1$–$C_4$-alkyl, saturated or unsaturated 5- to 10-membered heterocyclyl or heterocyclyl-$C_1$–$C_4$-alkyl which comprises 1 to 4 heteroatoms including 0 to 4 nitrogen atoms, 0 to 2 nonadjacent oxygen atoms and/or 0 to 2 nonadjacent sulphur atoms (in particular tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl), each of which radicals is optionally mono- to tetrasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio.

w particularly preferably represents 0, 1 or 2.

n particularly preferably represents 1, 2 or 3.

p particularly preferably represents 0, 1 or 2.

$R^1$ very particularly preferably represents fluorine, chlorine, bromine, $C_1$–$C_4$-alkyl, $C_1$–$C_4$-halogenoalkyl having 1 to 9 fluorine, chlorine and/or bromine atoms, $C_1$–$C_4$-alkoxy, $C_1$–$C_4$-halogenoalkoxy having 1 to 9 fluorine, chlorine and/or bromine atoms or —$S(O)_wR^4$.

$R^2$ and $R^3$ independently of one another very particularly preferably represent hydrogen, fluorine, chlorine, bromine, $C_1$–$C_4$-alkyl, $C_1$–$C_4$-halogenoalkyl having 1 to 9 fluorine, chlorine and/or bromine atoms, $C_1$–$C_4$-alkoxy or $C_1$–$C_4$-halogenoalkoxy having 1 to 9 fluorine, chlorine and/or bromine atoms.

$R^4$ very particularly preferably represents $C_1$–$C_4$-alkyl or represents in each case fluorine- or chlorine-substituted methyl or ethyl.

Het very particularly preferably represents 2-thienyl, 3-thienyl, 2-benzo[b]thienyl, 2-furyl, 3-furyl, 2-benzo[b]furyl, 2-indolyl, 2-thieno[3,2-b]thienyl, 2-thieno[3,2-b]furyl, 5-thieno[3,2-b]furyl, 2-thieno[2,3-f][1]benzothienyl, 2-thieno[2,3-f][1]benzofuryl, 6-thieno[2,3-f][1]benzofuryl, 2-pyridinyl, 3-pyridinyl, 2-pyrimidinyl, 5-pyrimidinyl, 3-pyridazinyl, 4-pyridazinyl, 2-pyrazinyl, triazolyl or tetrazolyl, each of which is optionally mono- to trisubstituted by identical or different $R^5$.

$R^5$ very particularly preferably represents the grouping —X—Y-Z-E, with the proviso that Y does not represent a direct bond if X does not represent a direct bond.

X very particularly preferably represents a direct bond, oxygen —$S(O)_w$—, —$NR^6$—, carbonyl, carbonyloxy, oxycarbonyl, oxysulphonyl ($OSO_2$), $C_1$–$C_4$-alkylene, $C_1$–$C_4$-halogenoalkylene having 1 to 8 fluorine, chlorine and/or bromine atoms, $C_2$–$C_4$-alkenylene, $C_2$–$C_4$-halogenoalkenylene having 1 to 6 fluorine, chlorine and/or bromine atoms, $C_2$–$C_4$-alkinylene, $C_1$–$C_4$-alkyleneoxy, oxy-$C_1$–$C_4$-alkylene, oxy-$C_1$–$C_4$-alkyleneoxy or —$S(O)_w$—$C_1$–$C_4$-alkylene.

Y very particularly preferably represents a direct bond or represents 1,4-phenylene, 1,3-phenylene, 1,2-phenylene, 2,6-naphthylene, 2,7-naphthylene, 1,4-naphthylene, 2,6-(1,2,3,4-tetrahydro)naphthylene, 2,7-(1,2,3,4-tetrahydro)naphthylene, 1,4-(1,2,3,4-tetrahydro)naphthylene, 5,8-(1,2,3,4-tetrahydro)naphthylene, 2,4-furylene, 2,4-thienylene, 2,4-pyrrolylene, 2,5-oxazolylene, 2,5-thiazolylene, 2,5-pyridinylene, 2,6-pyridinylene, 2,5-pyrimidinylene, 3,6-pyridazinylene or 2,5-pyrazinylene, each of which is optionally mono- to trisubstituted by identical or different radicals from the list $W^1$.

Z very particularly preferably represents a direct bond or —$(CH_2)_n$—.

E very particularly preferably represents hydrogen, fluorine, chlorine, bromine, hydroxyl, cyano, formyl, nitro, trimethylsilyl, dimethyl-tert-butylsilyl, —$S(O)_wR^7$, —$OSO_2R^7$, —$NR^8R^9$, —$COR^7$, —$CO_2R^7$, —$OC(O)R^7$, —$CONR^{10}R^{11}$, —$N(R^{12})COR^{13}$, —$SO_2NR^{16}R^{17}$; represents $C_1$–$C_{16}$-alkyl, $C_2$–$C_{16}$-alkenyl, $C_2$–$C_6$-alkinyl, $C_1$–$C_{16}$-alkoxy, $C_2$–$C_{16}$-alkenyloxy, each of which is optionally mono- or polysubstituted by identical or different substituents from the group consisting of fluorine, chlorine, bromine, cyano, $C_1$–$C_6$-alkoxy and —$NR^8R^9$; or represents $C_3$–$C_{10}$-cycloalkyl, $C_3$–$C_6$-cycloalkyl-$C_1$–$C_4$-alkyl, $C_3$–$C_{10}$-cycloalkyloxy, phenyl, phenoxy, benzyl, phenylethyl, benzyloxy, tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, piperidino, morpholinyl, thiomorpholinyl, morpholino, thiomorpholino, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_2$–$C_6$-alkenyl, $C_2$–$C_6$-halogenoalkenyl, $C_1$–$C_4$-alkoxy, $C_1$–$C_4$-halogenoalkoxy, $C_1$–$C_4$-alkylthio and $C_1$–$C_4$-halogenoalkylthio.

$W^1$ very particularly preferably represents fluorine, chlorine, bromine, cyano, formyl; trimethylsilyl, dimethyl-tert-butylsilyl, $C_1$–$C_4$-alkyl, $C_1$–$C_4$-alkoxy, $C_2$–$C_4$-alkenyl, $C_2$–$C_4$-alkenyloxy; represents $C_1$–$C_4$-halogenoalkyl, $C_1$–$C_4$-halogenoalkoxy having in each case 1 to 9 fluorine, chlorine and/or bromine atoms, $C_2$–$C_4$-halogenoalkenyl, $C_2$–$C_4$-halogenoalkenyloxy having in each case 1 to 8 fluorine, chlorine and/or bromine atoms; represents $C_1$–$C_4$-alkylcarbonyl, $C_1$–$C_4$-alkoxycarbonyl, —$S(O)_wR^7$, —$SO_2NR^{16}R^{17}$, —$(CH_2)_pNR^{16}R^{17}$, —$(CH_2)_pN(R^{16})COR^{17}$, —$(CH_2)_pN(R^{16})SO_2R^{17}$, —$OSO_2R^{16}$, —$OSO_2NR^{16}R^{17}$.

$R^6$ very particularly preferably represents methyl, ethyl, n-propyl, isopropyl, n-butyl, isobutyl, sec-butyl, tert-butyl, trifluoromethyl, trifluoroethyl, or represents cyclopropyl, cyclopropylmethyl, cyclopentyl, cyclopentylmethyl, cyclohexyl, cyclohexylmethyl, phenyl, benzyl or phenylethyl, each of which is optionally mono- to tetrasubstituted by identical or different substituents from the group consisting of fluorine, chlorine, brome, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and $C_1$–$C_4$-halogenoalkylthio having in each case 1 to 9 fluorine, chlorine and/or bromine atoms.

$R^7$ very particularly preferably represents $C_1$–$C_{10}$-alkyl which is optionally mono- or polysubstituted by identical or different substituents from, the group consisting of fluorine, chlorine, bromine and —$NR^8R^9$, represents cyclopropyl, cyclopentyl, cyclohexyl, phenyl or benzyl, each of which is optionally mono- to tetrasubstituted by identical or different substituents from the group consisting of fluorine, chlorine, bromine, cyano, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and $C_1$–$C_4$-halogenoalkylthio.

$R^8$ and $R^9$ independently of one another very particularly preferably represent hydrogen, —$SO_2R^7$, —$COR^7$, —$CO_2R^7$, represent $C_1$–$C_{16}$-alkyl or $C_2$–$C_{16}$-alkenyl, each of which is optionally mono- or polysubstituted by identical or different substituents from the group consisting of fluorine, chlorine, bromine, $C_1$–$C_4$-alkylcarbonyl, $C_1$–$C_4$-alkylcarbonyloxy, $C_1$–$C_4$-alkylamino, di-($C_1$–$C_4$-alkyl)-amino, $C_1$–$C_4$-alkoxy, $C_1$–$C_4$-halogenoalkoxy, $C_1$–$C_4$-alkylthio and $C_1$–$C_4$-halogenoalkylthio; represent $C_3$–$C_{10}$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^8$ and $R^9$ furthermore together very particularly preferably represent $C_2$–$C_{10}$-alkenylene which is optionally mono- or polysubstituted by identical or different substituents from the group consisting of fluorine, chlorine, bromine, $C_1$–$C_4$-alkoxy, $C_1$–$C_4$-halogenoalkoxy, $C_1$–$C_4$-alkylthio and $C_1$–$C_4$-halogenoalkylthio or represent $C_3$–$C_{10}$-alkylene, which is optionally mono- or polysubstituted in the alkylene moiety by identical or different substituents from the group consisting of fluorine, chlorine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio, where the alkylene chain may in each case be interrupted by —O—, —S— or —$NR^{18}$—.

$R^{10}$ and $R^{11}$ independently of one another very particularly preferably represent hydrogen, —$SO_2R^7$, represent $C_1$–$C_6$-alkyl or $C_2$–$C_6$-alkenyl, each of which is optionally mono- to nonasubstituted by identical or different substituents from the group consisting of fluorine, chlorine, bromine, $C_1$–$C_4$-alkylamino, di-($C_1$–$C_4$-alkyl)amino, $C_1$–$C_4$-alkoxy, $C_1$–$C_4$-halogenoalkoxy, $C_1$–$C_4$-alkylthio and $C_1$–$C_4$-halogenoalkylthio; represent $C_3$–$C_6$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$ alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^{10}$ and $R^{11}$ furthermore together very particularly preferably represent $C_4$–$C_6$-alkylene, —$(CH_2)_2$—O—$(CH_2)_2$—, —$(CH_2)_2$—S—$(CH_2)_2$— or —$(CH_2)$—N$(R^{18})$—$(CH_2)_2$—, each of which is optionally mono- to tetrasubstituted in the alkylene-moiety by identical or different substituents from the group consisting of fluorine, chlorine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^{12}$ and $R^{13}$ independently of one another very particularly preferably represent hydrogen, represent $C_1$–$C_6$-alkyl which is optionally mono- to nonasubstituted by identical or different substituents from the group consisting of fluorine, chlorine, bromine, $C_1$–$C_4$-alkoxy and $C_1$–$C_4$-alkylthio, represent $C_3$–$C_6$-cycloalkyl, $C_3$–$C_6$-cycloalkyl-$C_1$–$C_4$-alkyl, phenyl, benzyl or phenylethyl, each of which is optionally mono- to tetrasubstituted by identical or different substituents from the group consisting of fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^{12}$ and $R^{13}$ furthermore together very particularly preferably represent $C_3$–$C_8$-alkylene or $C_3$–$C_8$-alkenylene, each of which is optionally mono- to tetrasubstituted by identical or different substituents from the group consisting of fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^{16}$ and $R^{17}$ independently of one another very particularly preferably represent hydrogen, $C_1$–$C_6$-alkyl, $C_1$–$C_4$-halogenoalkyl having 1 to 9 fluorine, chlorine and/or bromine atoms or represent $C_3$–$C_6$-cycloalkyl which is optionally mono- to tetrasubstituted by identical or different substituents from the group consisting of fluorine, chlorine; bromine and $C_1$–$C_4$-alkyl.

$R^{16}$ and $R^{17}$ furthermore together very particularly preferably represent —$(CH_2)_3$—, —$(CH_2)_4$—, —$(CH_2)_5$—, —$(CH_2)_2$—O—$(CH_2)_2$— or —$(CH_2)_2$—S—$(CH_2)_2$—.

$R^{18}$ very particularly preferably represents hydrogen, —$SO_2R^7$, represents —$COR^7$ or —$CO_2R^7$; represents $C_1$–$C_{16}$-alkyl or $C_2$–$C_{16}$-alkenyl, each of which is optionally mono- or polysubstituted by identical or different substituents from the group consisting of fluorine, chlorine, bromine, cyano, methylamino, ethylamino, di-($C_1$–$C_6$-alkyl)amino, $C_1$–$C_4$-alkoxy, $C_1$–$C_4$-halogenoalkoxy, $C_1$–$C_4$-alkylthio and $C_1$–$C_4$-halogenoalkylthio; represents $C_3$–$C_{10}$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl $C_1$–$C_4$-alkoxy, $C_1$–$C_4$-halogenoalkoxy, $C_1$–$C_4$-alkylthio and $C_1$–$C_4$-halogenoalkylthio.

w very particularly preferably represents 0, 1 or 2.

n very particularly preferably represents 1 or 2.

p very particularly preferably represents 0 or 1.

$R^1$ especially preferably represents fluorine, chlorine, bromine, methyl, trifluoromethyl, methoxy, trifluoromethoxy, methylthio or trifluoromethylthio.

$R^2$ and $R^3$ independently of one another especially preferably represent hydrogen, fluorine, chlorine, bromine, methyl, trifluoromethyl, methoxy or trifluoromethoxy.

Het especially preferably represents 2-thienyl, 3-thienyl, 2-benzo[b]thienyl, 2-furyl, 3-furyl, 2-benzo[b]furyl, 2-thieno[3,2-b]thienyl, 2-thieno[3,2-b]furyl, 5-thieno[3,2-b]furyl, 2-thieno[2,3-f][1]benzothienyl, 2-thieno[2,3-f][1]benzofuryl, 6-thieno[2,3-f][1]benzofuryl, 2-pyridinyl, 3-pyridinyl, 2-pyrimidinyl, 5-pyrimidinyl, 3-pyridazinyl, 4-pyridazinyl or 2-pyrazinyl, each of which is optionally mono- or disubstituted by identical or different $R^5$.

$R^5$ especially preferably represents the grouping —X—Y-Z-E, with the proviso that Y does not represent a direct bond if X does not represent a direct bond.

X especially preferably represents a direct bond, oxygen, sulphur, —$SO_2$—, —$NR^6$—, —CO—, —C(O)—O—, —O—C(O)—, —$CH_2$—, —$(CH_2)_2$—, —C=C— (E or Z), —C≡C—, —$CH_2$O—, —$(CH_2)_2$O—, —$OCH_2$—, —$O(CH_2)_2$—, —O—$CH_2$—O—, —$SCH_2$—, —$S(CH_2)_2$—, —$CH_2$S— or —$(CH_2)_2$S—.

Y especially preferably represents a direct bond or represents 1;4-phenylene, 1,3-phenylene, 2,6-naphthylene, 2,7-naphthylene, 2,4-furylene, 2,4-thienylene, 2,5-pyridinylene, 2,5-pyrimidinylene, 3,6-pyridazinylene or 2,5-pyrazinylene, each of which is optionally mono- or disubstituted by identical or different radicals from the list $W^1$.

Z especially preferably represents a direct bond, methylene or ethylene.

E especially preferably represents hydrogen, fluorine, chlorine, bromine, hydroxyl, cyano, formyl, —$S(O)_wR^7$, —$OSO_2R^7$, —$NR^8R^9$, —$COR^7$, —$CO_2R^7$, —$OC(O)R^7$, —$CONR^{10}R^{11}$, —$N(R^{12})COR^{13}$, —$SO_2NR^{16}R^{17}$; represents $C_1$–$C_{16}$alkyl, $C_2$–$C_{16}$-alkenyl, $C_1$–$C_{16}$-alkoxy, $C_2$–$C_{16}$-alkenyloxy, each of which is optionally mono- or polysubstituted by identical or different substituents from the group consisting of fluorine, chlorine, bromine, cyano, $C_1$–$C_6$-alkoxy and —$NR^8R^9$; or represents cyclopropyl, cyclopentyl, cyclohexyl, cyclopropyloxy, cyclopentyloxy, cyclohexyloxy, cyclopropylmethyl, cyclopentylmethyl, cyclohexylmethyl, phenyl, phenoxy, benzyl, phenylethyl, benzyloxy, tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, piperidino, morpholinyl, thiomorpholinyl, morpholino, thiomorpholino, triazinyl, triazolyl, quinolinyl or isoquinolinyl, each of which is optionally mono- to trisubstituted by identical or different substituents from the group consisting of fluorine, chlorine, bromine, cyano, methyl, ethyl, n-propyl, isopropyl, —$CF_3$, —$CHF_2$, —$CClF_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, —$CF_2CHFCF_3$, vinyl, allyl, 1-propenyl, butenyl, —CF=CHF, —CF=$CH_2$, —CF=$CCl_2$, —CH=$CF_2$, —$CF_2CF$=$CF_2$, —CH=CFH, —$CH_2CF$=$CF_2$, —CF=$CF_2$, —$CF_2CH$=$CF_2$, methoxy, ethoxy, n-propoxy, isopropoxy, n-butoxy, isobutoxy, sec-butoxy, tert-butoxy, trifluoromethoxy, difluoromethoxy, chlorodifluoromethoxy, trifluoroethoxy, methylthio, ethylthio, n-propylthio, isopropylthio, n-butylthio, isobutylthio, sec-butylthio, tert-butylthio, trifluoromethylthio, difluoromethylthio, chlorodifluoromethylthio and trifluoroethylthio.

$W^1$ especially preferably represents fluorine, chlorine, bromine, cyano, formyl, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, vinyl, allyl, trifluoromethyl, trifluoroethyl, trifluoromethoxy, trifluoroethoxy, —$OCF_2CF_2H$, —CH=$CF_2$, —CH=$CCl_2$, —OCF=$CF_2$, —COMe, —COEt, —$CO_2Me$, —$CO_2Et$, —$CO_2$(t-Bu), —SMe, —SOMe, —$SO_2Me$, —$SCF_3$, —$SOCF_3$, —$SO_2CF_3$, —$SCHF_2$, —$SOCHF_2$, —$SO_2CHF_2$, —$SO_2NMe_2$, —$NMe_2$, —$NEt_2$, —N(n-Pr)$_2$, —N(Me)COMe, —N(Me)COEt, —N(Me)COPr, —N(Me)CO(t-Bu), 2-pyrrolidonyl, 2-piperidonyl, —N(Me)$SO_2Me$, —N(Me)$SO_2Et$, —N(Me)$SO_2CF_3$, —N(Et)$SO_2CF_3$, —N(Me)$SO_2(CF_2)_3CF_3$ or —$OSO_2NMe_2$;

$R^6$ especially preferably represents methyl, ethyl, n-propyl, isopropyl, n-butyl, isobutyl, sec-butyl, tert-butyl, trifluoromethyl, trifluoroethyl, cyclopropyl, cyclopropylmethyl, cyclopentyl, cyclopentylmethyl, cyclohexyl, cyclohexylmethyl, phenyl, benzyl or phenylethyl.

$R^7$ especially preferably represents methyl, ethyl, n-propyl, isopropyl, n-butyl, isobutyl, sec-butyl, tert-butyl, pentyl, hexyl, —$CF_3$, —$CHF_2$, —$CCl_3$, —$CCl_2F$, dimethylaminomethyl, dimethylaminoethyl, diethylaminomethyl, diethylaminoethyl, cyclopropyl, cyclopentyl, cyclohexyl, phenyl or benzyl.

$R^8$ and $R^9$ independently of one another especially preferably represent hydrogen, —$SO_2R^7$, —$COR^7$, —$CO_2R^7$, represent $C_1$–$C_{16}$-alkyl or $C_2$–$C_{16}$-alkenyl, each of which is optionally mono- or polysubstituted by identical or different substituents from the group consisting of fluorine, chlorine, bromine, $C_1$–$C_4$-alkylcarbonyl, $C_1$–$C_4$-alkylcarbonyloxy, $C_1$–$C_4$-alkylamino, di-($C_1$–$C_4$-alkyl) amino, $C_1$–$C_4$-alkoxy, $C_1$–$C_4$-halogenoalkoxy, $C_1$–$C_4$-alkylthio and $C_1$–$C_4$-halogenoalkylthio; represent $C_3$–$C_8$-cycloalkyl, cyclopropylmethyl, cyclopentylmethyl, cyclohexylmethyl, cyclopropylethyl, cyclopentylethyl, cyclohexylethyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio.

$R^8$ and $R^9$ furthermore together especially preferably represent $C_2$–$C_8$-alkenylene which is optionally mono- or polysubstituted by identical or different substituents from the group consisting of fluorine, chlorine, bromine, $C_1$–$C_4$-alkoxy, $C_1$–$C_4$-halogenoalkoxy, $C_1$–$C_4$-alkylthio and $C_1$–$C_4$-halogenoalkylthio or represent $C_3$–$C_8$-alkylene, which is optionally mono- or polysubstituted in the alkylene moiety by identical or different substituents from the group consisting of fluorine, chlorine, cyano, methyl, ethyl, n-propyl, isopropyl, n-butyl, isobutyl, sec-butyl, tert-butyl, $C_1$–$C_4$-halogenoalkyl, methoxy, ethoxy, n-propoxy, isopropoxy, n-butoxy, isobutoxy, sec-butoxy, tert-butoxy, $C_1$–$C_4$-halogenoalkoxy, methylthio, ethylthio, n-propylthio, isopropylthio, n-butylthio, isobutylthio, sec-butylthio, tert-butylthio and $C_1$–$C_4$-halogenoalkylthio, where the alkylene chain may in each case be interrupted by —O—, —S— or —$NR^{18}$—.

$R^{10}$ and $R^{11}$ independently of one another especially preferably represent hydrogen, —$SO_2CF_3$, methyl, ethyl, n-propyl, isopropyl, n-butyl, isobutyl, sec-butyl, tert-butyl, pentyl, hexyl, —$CF_3$, —$CH_2CF_3$, —$(CF_2)_3CF_3$, methoxymethyl, methoxyethyl, cyclopropyl, cyclopentyl, cyclohexyl, or represent phenyl or benzyl, each of which is optionally mono- to trisubstituted by identical or different substituents from the group consisting of fluorine, chlorine, bromine, methyl, trifluoromethyl, methoxy and trifluoromethoxy.

$R^{10}$ and $R^{11}$ furthermore together especially preferably represent —$(CH_2)_4$—, —$(CH_2)_5$—, —$(CH_2)_6$—, —$CH_2$—$CH(CH_3)$—$CH_2$—$CH(CH_3)$—$CH_2$—, —$(CH_2)_2$—O—$(CH_2)_5$—, —$(CH_2)_2$—S—$(CH_2)_2$— or —$(CH_2)_2$—N$(R^{18})$—$(CH_2)_2$—.

$R^{12}$ and $R^{13}$ independently of one another especially preferably represent hydrogen, methyl, ethyl, n-propyl, isopropyl, n-butyl, isobutyl, sec-butyl, tert-butyl, n-hexyl, trifluoromethyl, trifluoroethyl, cyclopropyl, cyclopentyl, cyclohexyl or represent phenyl or benzyl, each of which is optionally mono- to tetrasubstituted by identical or different substituents from the group consisting of fluorine, chlorine, bromine, methyl, trifluoromethyl, methoxy and trifluoromethoxy.

$R^{12}$ and $R^{13}$ furthermore together especially preferably represent —$(CH_2)_3$—, —$(CH_2)_4$—, —$(CH_2)_5$— or —$(CH_2)_6$—, each of which is optionally mono- to tetrasubstituted by identical or different substituents from the group consisting of fluorine, chlorine, bromine, methyl, ethyl, methoxy, ethoxy, methylthio, ethylthio, trifluoromethyl, trifluoromethoxy and trifluoromethylthio.

$R^{16}$ and $R^{17}$ independently of one another especially preferably represent hydrogen, methyl, ethyl, n-propyl, isopropyl, n-butyl, isobutyl, sec-butyl, tert-butyl, n-hexyl, trifluoromethyl, trifluoroethyl, cyclopropyl, cyclopentyl or cyclohexyl.

$R^{16}$ and $R^{17}$ furthermore together especially preferably represent —$(CH_2)_3$—, —$(CH_2)_4$—, —$(CH_2)_5$—, —$(CH_2)_2$—O—$(CH_2)_2$— or —$(CH_2)_2$—S—$(CH_2)_2$—.

$R^{18}$ especially preferably represents hydrogen, —$SO_2R^7$; represents —$COR^7$ or —$CO_2R^7$; represents $C_1$–$C_{16}$-alkyl or $C_2$–$C_{16}$-alkenyl, each of which is optionally mono- or polysubstituted by identical or different substituents from the group consisting of fluorine, chlorine, bromine, cyano, methylamino, ethylamino, di-($C_1$–$C_6$-alkyl)amino, $C_1$–$C_4$-alkoxy, $C_1$–$C_4$-halogenoalkoxy, $C_1$–$C_4$-alkylthio and $C_1$–$C_4$-halogenoalkylthio; represents $C_3$–$C_8$-cycloalkyl, cyclopropylmethyl, cyclopentylmethyl, cyclohexylmethyl, cyclopropylethyl, cyclopentylethyl, cyclohexylethyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, methyl, ethyl, n-propyl, isopropyl, n-butyl, isobutyl, sec-butyl, tert-butyl, $C_1$–$C_4$-halogenoalkyl, methoxy, ethoxy, n-propoxy, isopropoxy, n-butoxy, isobutoxy, sec-butoxy, tert-butoxy, $C_1$–$C_4$-halogenoalkoxy, methylthio, ethylthio, n-propylthio, isopropylthio, n-butylthio, isobutylthio, sec-butylthio, tert-butylthio and $C_1$–$C_4$-halogenoalkylthio.

Very particular preference is furthermore given to compounds of the formulae (I-1) to (I-16).

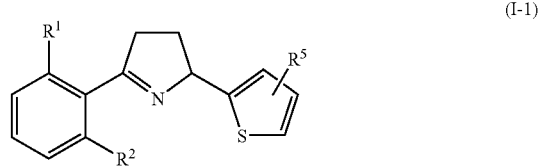
(I-1)

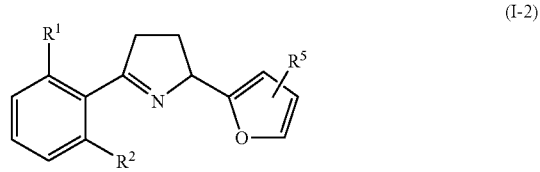
(I-2)

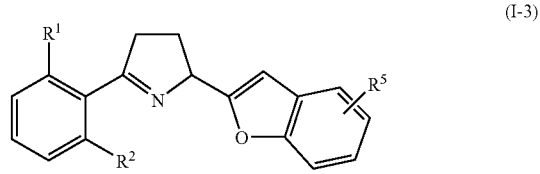
(I-3)

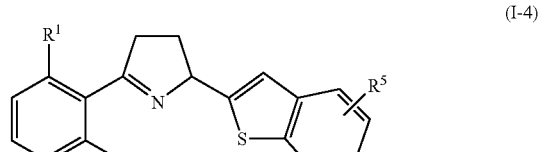
(I-4)

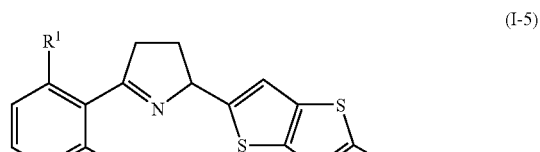
(I-5)

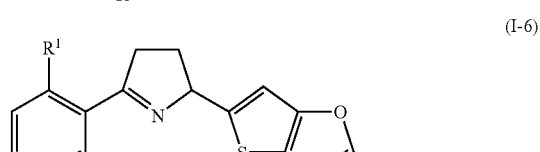
(I-6)

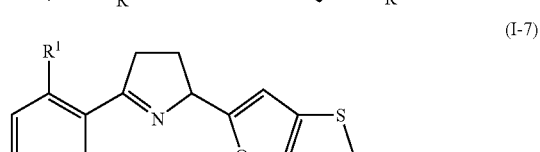
(I-7)

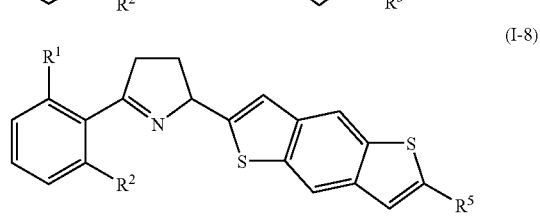
(I-8)

-continued

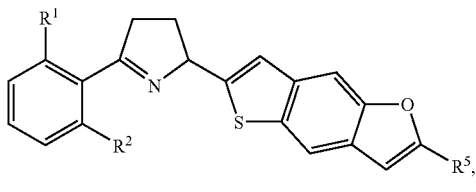 (I-9)

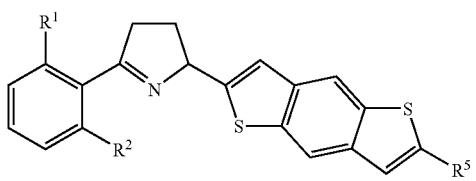 (I-10)

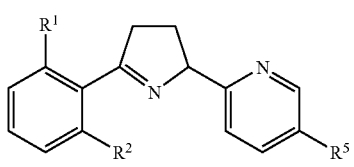 (I-11)

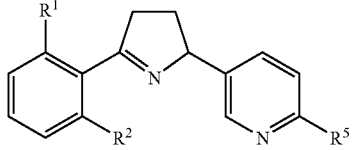 (I-12)

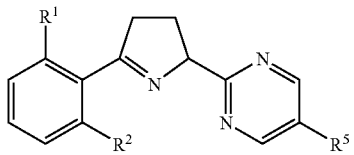 (I-13)

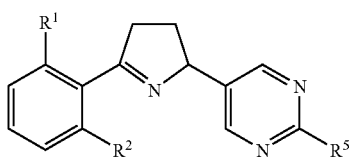 (I-14)

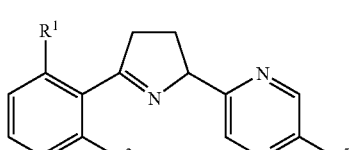 (I-15)

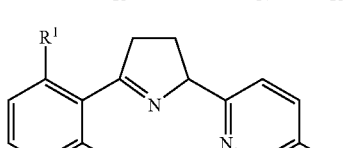 (I-16)

in which in each case
$R^1$ represents fluorine r chlorine,
$R^2$ represents hydrogen or fluorine and
$R^5$ has the meanings given above.

In the compounds of the formulae (I-1) to (I-16), $R^1$, $R^2$ and $R^5$ preferably, particularly preferably, very particularly preferably and especially preferably have those meanings which have already been mentioned above as being preferred, particularly preferred, etc., for these radicals.

Very particular preference is furthermore given to compounds of the formula (I-d) having the (R)-configuration

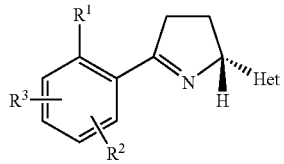 (I-d)

in which
$R^1$, $R^2$, $R^3$ and Het have the meanings given above.

In the compounds of the formula (I-d), $R^1$, $R^2$, $R^3$ and Het preferably, particularly preferably, very particularly preferably and especially preferably have those meanings which have already been mentioned above as being preferred, particularly preferred, etc., for these radicals.

Very particular preference is furthermore given to compounds of the formulae (I-17) to (I-32) having the (R)-configuration

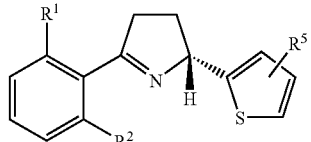 (I-17)

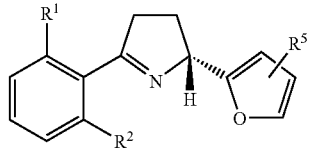 (I-18)

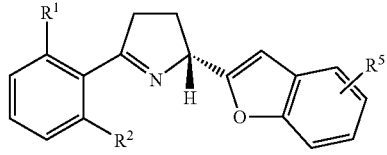 (I-19)

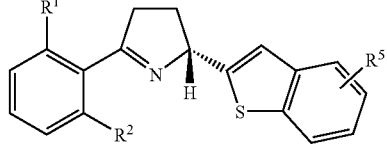 (I-20)

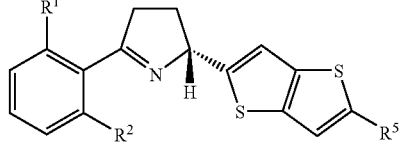 (I-21)

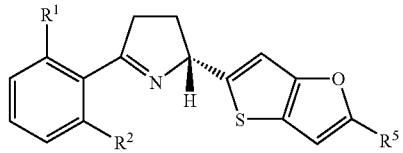 (I-22)

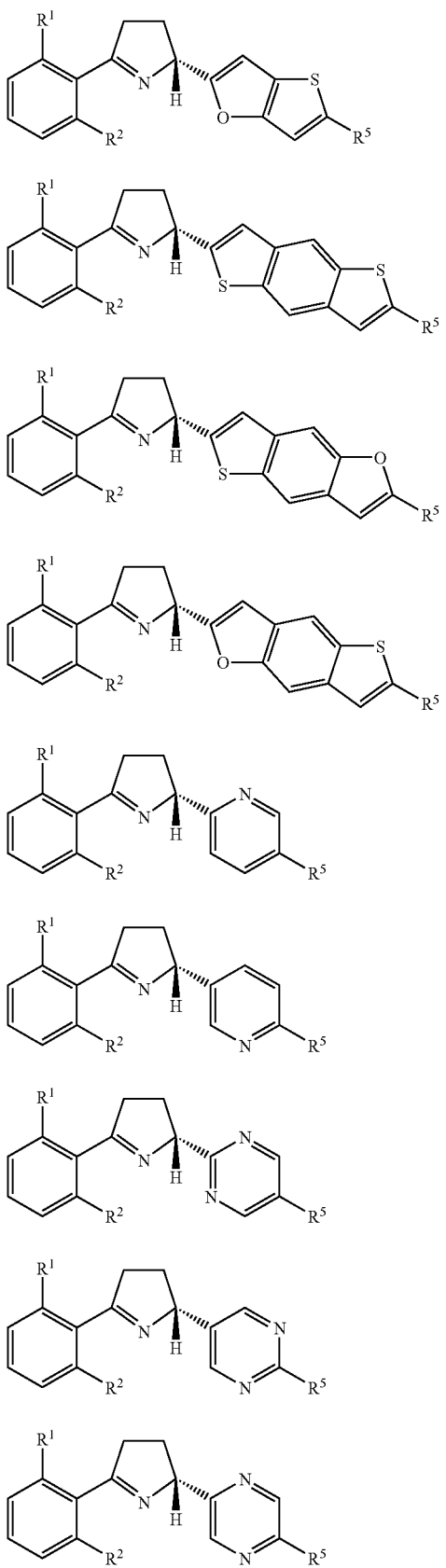

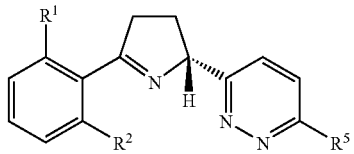

in which in each case

R¹ represents fluorine or chlorine,
R² represents hydrogen or fluorine and
R⁵ has the meanings given above.

In the compounds of the formulae (I-17) to (I-32), $R^1$, $R^2$ and $R^5$ preferably, particularly preferably, very particularly preferably and especially preferably have those meanings which have already been mentioned above as being preferred, particularly preferred, etc., for these radicals.

Compounds of the formula (I-d) are obtained by customary processes for optical resolution, such as, for example, by chromatographing the corresponding racemates on a chiral stationary phase. In this manner, it is possible to separate both racemic end products and racemic intermediates into the two enantiomers.

Saturated hydrocarbon radicals, such as alkyl, can in each case be straight-chain or branched as far as this is possible, including in combination with heteroatoms, such as, for example, an alkoxy.

However, the abovementioned general or preferred radical definitions or illustrations can also be combined with one another as desired, i.e. between the respective ranges and preferred ranges. They apply both to the end products and, correspondingly, to the precursors and intermediates.

Using tert-butyl-1-(5-bromo-2-thienyl)-4-(2,6-difluorophenyl)-4-oxobutylcarbamate as starting material and trifluoroacetic acid (TFA), the course of the process (A) according to the invention can be illustrated by the equation below.

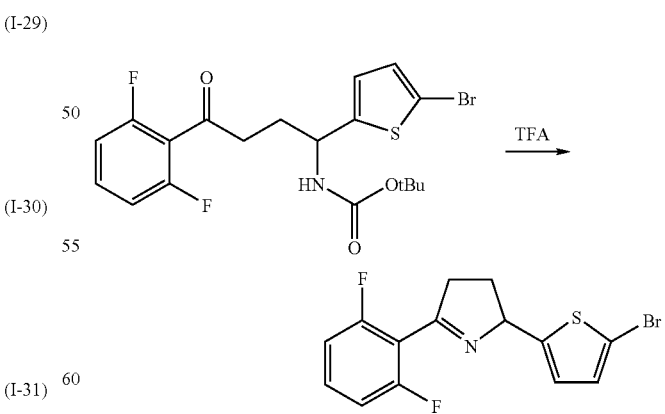

Using 4-azido-4-(6-chloro-3-pyridinyl)-1-(2,6-difluorophenyl)-1-butanone as starting material and triphenylphosphine (PPh₃), the course of the process (B) according to the invention can be illustrated by the equation below.

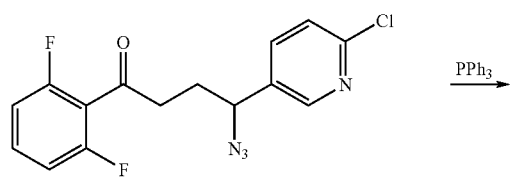

Using N-[1-(4-bromo-2-thienyl)-4-(2,6-difluorophenyl)-4-oxobutyl]acetamide as starting material and hydrochloric acid (HCl), the course of the process (C) according to the invention can be illustrated by the equation below.

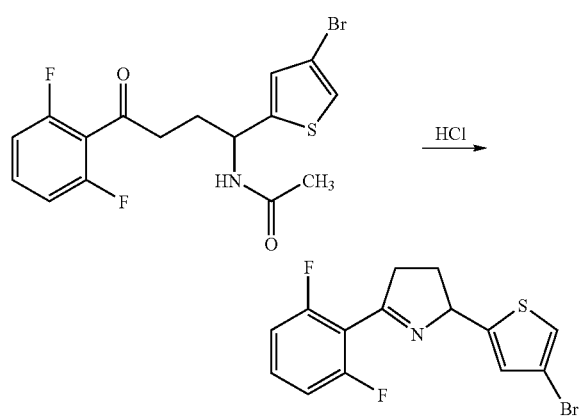

Using 2-chloro-5-[5-(2,6-difluorophenyl)-3,4-dihydro-2H-pyrrol-2-yl]pyridine and N-(5-bromo-2-pyrimidinyl)-N,N-diethylamine as starting materials and 4,4,4',4',5,5,5',5'-octamethyl-2,2'-bis-1,3,2-dioxaborolane and a palladium catalyst, the course of the process (D) according to the invention can be illustrated by the equation below.

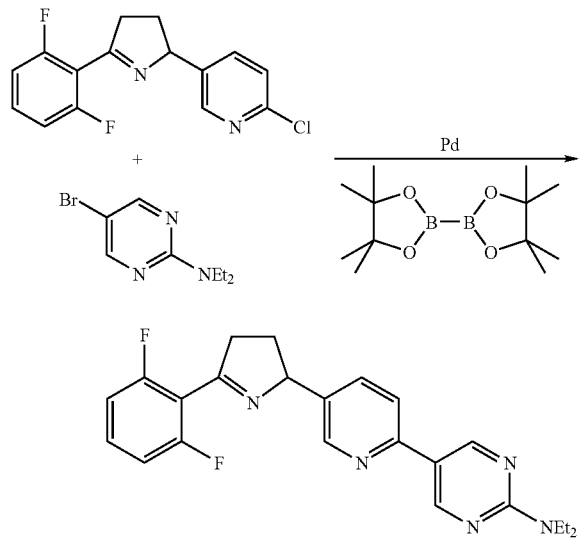

Using 2-(4,4,5,5'-tetramethyl-1,3,2-dioxaborolan-2-yl)-5-[5-(2,6-difluorophenyl)-3,4-dihydro-2H-pyrrol-2-yl]pyridine and 5-bromo-2-trifluoromethoxypyrimidine as starting materials and a palladium catalyst, the course of the process (E) according to the invention can be illustrated by the equation below.

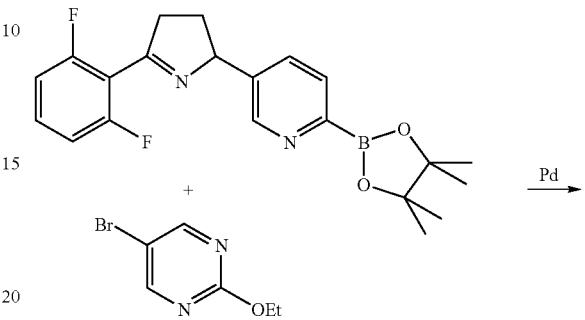

Using 2-chloro-5-[5-(2,6-difluorophenyl)-3,4-dihydro-2H-pyrrol-2-yl]pyridine and 4-trifluoromethoxyphenylboronic acid as starting materials and a palladium catalyst, the course of the process (F) according to the invention can be illustrated by the equation below.

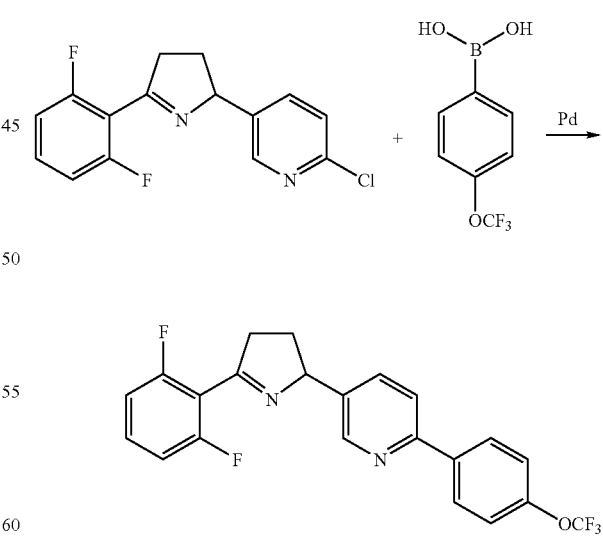

Using 2-bromo-5-[5-(2,6-difluorophenyl)-3,4-dihydro-2H-pyrrol-2-yl]pyridine and 2-trifluoromethyl-5-(tributylstannyl)pyridine as starting materials and a palladium catalyst, the course of the process (G) according to the invention can be illustrated by the equation below.

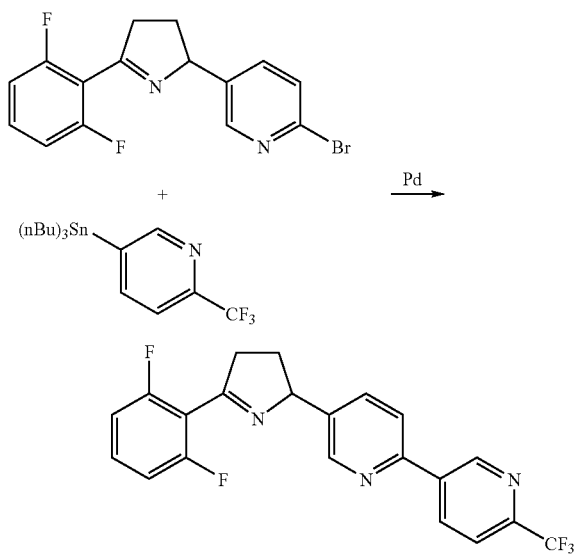

Explanation of the Processes and Intermediates

Process (A)

The formula (II) provides a general definition of the aminoketones required as starting materials for carrying out the process (A) according to the invention. In this formula $R^1$, $R^2$, $R^3$ and Het preferably, particularly preferably, very particularly preferably and especially preferably have those meanings which have already been mentioned in connection with the description of the compounds of the formula (I) according to the invention as being preferred, particularly preferred, etc., for these radicals.

Aminoketones of the formula (II) are novel. They can be prepared by a) reacting lactams of the formula (IX)

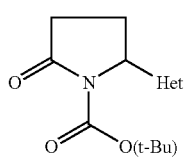

(IX)

in which

Het has the meanings given above with metallated aromatic compounds of the formula (X)

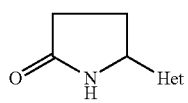

(X)

in which $R^1$, $R^2$ and $R^3$ have the meanings given above and $M^1$ represents Li, MgCl, MgBr, MgI or ZnCl, at temperatures between minus 70° C. and plus 70° C., if appropriate in the presence of a diluent (for example tetrahydrofuran).

The formula (IX) provides a general definition of the lactams required as starting materials for carrying out the process (a). In this formula, Het preferably, particularly preferably, very particularly preferably and especially preferably has those meanings which have already been mentioned in connection with the description of the compounds of the formula (I) according to the invention as being preferred, particularly preferred, etc., for this radical.

Lactams of the formula (IX) are novel. They can be prepared by b) reacting lactams of the formula (XI)

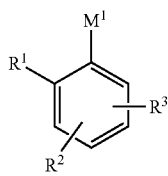

(XI)

in which

Het has the meanings given above for example with di-tert-butyl dicarbonate in the presence of a base (for example dimethylaminopyridine) and, if appropriate, in the presence of a diluent (for example dichloromethane) (cf. Tetrahedron Lett. 1998, 39, 2705–2706).

The formula (X) provides a general definition of the metallated aromatic compounds required as starting materials for carrying out the process (a). In this formula, $R^1$, $R^2$ and $R^3$ preferably, particularly preferably, very particularly preferably and especially preferably have those meanings which have already been mentioned in connection with the description of the compounds of the formula (I) according to the invention as being preferred, particularly preferred, etc., for these radicals. $M^1$ preferably represents Li, MgCl, MgBr, MgI or ZnCl, particularly preferably Li, MgCl, MgBr or MgI, very particularly preferably Li, MgCl or MgBr.

Metallated aromatic compounds of the formula (X) are known and/or can be prepared by known methods (for example lithiation or Grignard reaction) from the corresponding aromatic or halogenated aromatic compounds.

The formula (XI) provides a general definition of the lactams required as starting materials for carrying out the process (b). In this formula, Het preferably, particularly preferably, very particularly preferably and especially preferably has those meanings which have already been mentioned in connection with the description of the compounds of the formula (I) according to the invention as being preferred, particularly preferred, etc., for this radical.

Some of the lactams of the formula (XI) are known. They can be prepared, for example, by c) reacting alkoxylactams of the formula (XII)

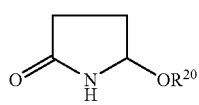

(XII)

in which

R$^{20}$ represents alkyl either

α) with heteroaromatic compounds of the formula (XIII)

in which

Het$^5$ represents 5- to 14-membered heteroaryl which comprises 1 to 3 aromatic rings and one or more heteroatoms from the group consisting of oxygen and sulphur and is optionally mono- to tetrasubstituted by identical or different R$^5$, where R$^5$ has the meanings given above, in the presence of a protonic acid (for example sulphuric acid, acetic acid) or a Lewis acid (for example-aluminium chloride), if appropriate in the presence of a diluent (for example dichloromethane or acetonitrile) (cf. Tetrahedron 1976, 32, 1571), or β) with Grignard compounds of the formula (XIV)

in which

Het has the meanings given above and

Hal$^1$ represents halogen in the presence of a diluent (for example tetrahydrofuran) (cf. Org. Prep. Proced. Int. 1993, 25, 255).

The formula (XII) provides a general definition of the alkoxylactams required as starting materials for carrying out the process (c). In this formula, R$^{20}$ preferably represents C$_1$–C$_6$-alkyl, particularly preferably C$_1$–C$_4$-alkyl, very particularly preferably methyl or ethyl.

The alkoxylactams of the formula (XII) are known and can be prepared, for example, from the corresponding unsubstituted imides by cathodic reduction or reduction with sodium boronate or from the unsubstituted lactams by anodic oxidation (cf. J. Org. Chem. 1991, 56, 1822; Synthesis 1980, 315).

The formula (XIII) provides a general definition of the heteroaromatic compounds required as starting materials for carrying out the process (α). In this formula, Het$^5$ preferably represents 5- to 14-membered heteroaryl which comprises 1 to 3 aromatic rings and 1 or 2 heteroatoms including 0 to 2 nonadjacent oxygen atoms and/or 0 to 2 nonadjacent sulphur atoms (in particular thienyl, benzothienyl, furyl, benzofuryl, thienothienyl, thienofuryl, thienobenzothienyl or thienobenzofuryl), each of which radicals is optionally mono- to tetrasubstituted by identical or different R$^5$. Het$^5$ particularly preferably represents 2-thienyl, 3-thienyl, 2-benzo[b]thienyl, 2-furyl, 3-furyl, 2-benzo[b]furyl, 2-thieno[3,2-b]thienyl, 2-thieno[3,2-b]furyl, 5-thieno[3,2--b]furyl, 2-thieno[2,3-f][1]benzothienyl, 2-thieno[2,3-f][1]benzofuryl or 6-thieno[2,3-f][1]benzofuryl, each of which is optionally mono- to trisubstituted by identical or different R$^5$. Het$^5$ very particularly preferably represents 2-thienyl, 3-thienyl, 2-benzo[b]thienyl, 2-furyl, 3-furyl, 2-benzo[b]furyl, 2-thieno[3,2-b]thienyl, 2-thieno[3,2-b]furyl, 5-thieno[3,2-b]furyl, 2-thieno[2,3-f][1]benzothienyl, 2-thieno[2,3-f][)]benzofuryl or 6-thieno[2,3-f][1]benzofuryl, each of which is optionally mono- or disubstituted by identical or different R$^5$. R$^5$ here preferably, particularly preferably, very particularly preferably and especially preferably has those meanings which have already been mentioned in connection with the description of the compounds of the formula (I) according to the invention as being preferred, particularly preferred, etc., for these radicals.

The heteroaromatic compounds of the formula (XIII) are known and/or can be prepared by known methods.

The formula (XIV) provides a general definition of the Grignard compounds required as starting materials for carrying out the process (β). In this formula, Het preferably, particularly preferably, very particularly preferably and especially preferably has those meanings which have already been mentioned in connection with the description of the compounds of the formula (I) according to the invention as being preferred, particularly preferred, etc., for this radical. Hall preferably represents chlorine, bromine or iodine.

The Grignard compounds of the formula (XIV) are known and/or can be prepared by known processes.

Suitable diluents for carrying out the process (A) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; or sulphones, such as sulpholane. Methylene chloride, chloroform, toluene, methanol or ethanol are used with particular preference.

Suitable for carrying out the process (A) according to the invention are in each case all customary Lewis acids or protonic acids. Methods for removing Boc are generally known (cf., for example, T. W. Greene, P. G. M. Wuts, Protective Groups in Organic Synthesis, Ed. 3, New York, Wiley & Sons, 1999, pp. 520–525). Preference is given to using trifluoroacetic acid, HCl or HBr for removing the Boc protective group.

When carrying out the process (A) according to the invention, the reaction temperatures can in each case be varied within a relatively wide range. In general, the process is carried out at temperatures between –20° C. and +120° C., preferably between –10° C. and 60° C.

When carrying out the process (A) according to the invention, in general 100 mol of a protonic acid are employed per mole of the compounds of the formula (II).

However, it is also possible to employ the reaction components in other ratios. Work-up is carried out by customary methods. In general, the reaction mixture is concentrated, taken up in a suitable solvent and adjusted to pH 12 using sodium hydroxide, and the organic phase is washed with water, dried over sodium sulphate, filtered and concentrated. The residue is, if appropriate, freed from any impurities that may still be present using customary methods, such as chromatography or recrystallization.

Process (B)

The formula (III) provides a general definition of the azides required as starting materials for carrying out the process (B) according to the invention. In this formula R$^1$, $R^2$, $R^3$ and Het preferably, particularly preferably, very particularly preferably and especially preferably have those meanings which have already been mentioned in connection with the description of the compounds of the formula (I) as being preferred, particularly preferred, etc., for these radicals.

Azides of the formula (III) are novel. They can be prepared by d) reacting halides of the formula (XV)

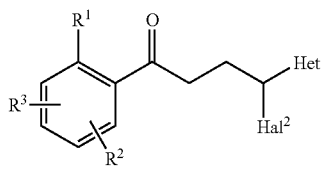

in which
$R^1$, $R^2$, $R^3$ and Het have the meanings given above and
$Hal^2$ represents halogen
with azides of the formula (XVI)

Q-N$_3$ (XVI)

in which
Q represents a cation
in the presence of a diluent (for example water/acetone mixtures or water/ethanol mixtures) and, if appropriate, in the presence of a catalyst (for example methyltrioctylammonium chloride=Aliquat 336, cf. M. Es-Sayed, Phd Thesis, University of Göttingen, 1992).

The formula (XV) provides a general definition of the halides required as starting materials for carrying out the process (d). In this formula $R^1$, $R^2$, $R^3$ and Het preferably, particularly preferably, very particularly preferably and especially preferably have those meanings which have already been mentioned in connection with the description of the compounds of the formula (I) according to the invention as being preferred, particularly preferred, etc., for these radicals. $Hal^2$ preferably represents chlorine, bromine or iodine, particularly preferably chlorine or bromine, very particularly preferably chlorine.

Halides of the formula (XV) are novel. They can be prepared by e) reacting cyclopropanes of the formula (XVII)

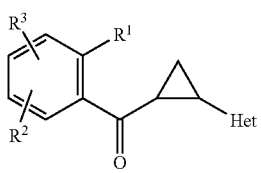

in which
$R^1$, $R^2$, $R^3$ and Het have the meanings given above
with a protonic acid (for example HCl), if appropriate in the presence of a diluent (for example water).

The formula (XVI) provides a general definition of the azides required as starting materials for carrying out the process (d). In this formula, Q preferably represents alkali metal ions, trialkylsilyl, tetraalkylammonium, tetraalkylguanidinium or polymer-bound trialkylammonium. With particular preference, Q represents sodium, lithium, trimethylsilyl, tetraethylammonium, tetra-n-butylammonium or tetramethylguanidinium, very particularly preferably sodium or lithium.

Azides of the formula (XVI) are commercially available and/or can be prepared by known methods (cf. Houben-Weyl: Methoden der Organischen Chemie, 4. edition, Organonitrogen Compounds I, pages 1243–1290; Editor: D. Klamann).

The formula (XVII) provides a general definition of the cyclopropanes required as starting materials for carrying out the process (e). In this formula $R^1$, $R^2$, $R^3$ and Het preferably, particularly preferably, very particularly preferably and especially preferably have those meanings which have already been mentioned in connection with the description of the compounds of the formula (I) as being preferred, particularly preferred, etc., for these radicals.

Some of the cyclopropanes of the formula (XVII) are known. They can be prepared, for example, by f) reacting α,β-unsaturated ketones of the formula (XVIII)

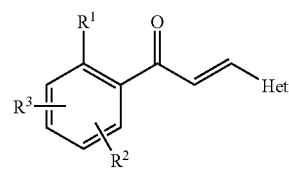

in which
$R^1$, $R^2$, $R^3$ and Het have the meanings given above
with a trialkylsulphoxonium halide (for example trimethylsulphoxonium iodide) in the presence of a base (for example sodium hydride) and, if appropriate, in the presence of a diluent (for example dimethyl sulphoxide) (cf. Tetrahedron Asymmetry 1998, 9, 1035).

The formula (XVIII) provides a general definition of the α,β-unsaturated ketones required as starting materials for carrying out the process (f). In this formula $R^1$, $R^2$, $R^3$ and Het preferably, particularly preferably, very particularly preferably and especially preferably have those meanings which have already been mentioned in connection with the description of the compounds of the formula (I) according to the invention as being preferred, particularly preferred, etc., for these radicals.

α,β-Unsaturated ketones of the formula (XVIII) are known. They can be prepared, for example, by g) reacting aldehydes of the formula (XIX)

Het-CHO (XIX)

in which
Het has the meanings given above
with acetophenones of the formula (XX)

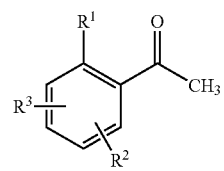

in which

R$^1$, R$^2$ and R$^3$ have the meanings given above in the presence of a base (for example sodium hydroxide) and in the presence of a diluent (for example methanol).

The formula (XIX) provides a general definition of the aldehydes required as starting materials for carrying out the process (g). In this formula, Het preferably, particularly preferably, very particularly preferably and especially preferably has those meanings which have already been mentioned in connection with the description of the compounds of the formula (I) according to the invention as being preferred, particularly preferred, etc., for these radicals.

Aldehydes of the formula (XIX) are known and/or can be prepared by known methods.

The formula (XX) provides a general definition of the acetophenones required as starting materials for carrying out the process (g). In this formula R$^1$, R$^2$ and R$^3$ preferably, particularly preferably, very particularly preferably and especially preferably have those meanings which have already been mentioned in connection with the description of the compounds of the formula (I) according to the, invention as being preferred, particularly preferred, etc., for these radicals.

Acetophenones of the formula (XX) are known and/or can be prepared by known methods.

Cyclopropanes of the formula (XVII-a)

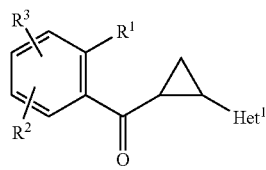

(XVII-a)

in which

R$^1$, R$^2$, R$^3$ and Het$^1$ have the meanings given above can also be prepared by h) reacting cyclopropanes of the formula (XVII-b)

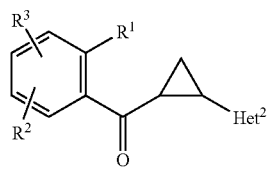

(XVII-b)

in which

R$^1$, R$^2$, R$^3$ and Het$^2$ have the meanings given above with boronic acid derivatives of the formula (VII)

A$^2$-Y$^1$-E     (VII)

in which

Y$^1$, E and A$^2$ have the meanings given above in the presence of a catalyst, if appropriate in the presence of an acid binder and, if appropriate, in the presence of a diluent.

This process corresponds to the process (F) according to the invention in which Δ$^1$-pyrrolines of the formula (I-b) are reacted. The coupling reactions according to processes (D) and (E) can also be applied to cyclopropanes of the formula (XVII-a).

The cyclopropanes of the formula (XVII-b) used as starting materials in process (h) are a sub-group of the compounds of the formula (XVII) and can be prepared analogously to process (f).

Boronic acid derivatives of the formula (VII) are described below in the description of process (F) according to the invention.

For process (h), it is possible to use the same reaction conditions, diluents, reaction auxiliaries and catalysts as for process (F) described below.

When carrying out the process (B) according to the invention, it is possible to employ all the trialkylphosphines, triarylphosphines and trialkyl phosphites which are customarily used for this purpose (cf. Tetrahedron Lett. 1999, 40, 4825; Tetrahedron 1997, 53, 3693; Tetrahedron 1997, 55, 8353; J. Chem. Soc. Chem. Commun. 1982, 1224; Synthesis 1996, 123). Preference is given to using organophosphorus compounds such as triphenylphosphine, tri-n-butylphosphine or trimethyl phosphite, particularly preferably triphenylphosphine.

It is furthermore possible to convert azides of the formula (III) by catalytic hydrogenation, for example with the catalyst PtO$_2$, according to the process according to the invention and compounds of the formula (I) (cf. J. Am. Chem. Soc. 1954, 76, 1231).

Further alternatives for reducing azido compounds are described in the literature (cf. Houben-Weyl: Methoden der Organischen Chemie, 4. Edition, Organonitrogen Compounds II, pages 956–975; Editor: D. Klamann).

Suitable diluents for carrying out the process (B) according to the invention are aliphatic or aromatic hydrocarbons, halogenated hydrocarbons or ethers. Preference is given to using pentane, hexane, heptane, benzene, toluene, tetrahydrofuran, diethyl ether, dioxane or acetonitrile, particularly preferably pentane, hexane or heptane.

The reaction temperatures for carrying out the process (B) according to the invention can be varied within a relatively wide range. In general, the process is carried out at temperatures between −10° C. and +60° C., preferably between 0° C. and 40° C., particularly preferably at room temperature.

When carrying out the process (B) according to the invention, in general 1 mol of trialkylphosphine or triarylphosphine or trialkyl phosphite and a suitable diluent are employed per mole of the azide of the formula (III). However, it is also possible to choose other ratios of the reaction components. Work-up is carried out by customary methods. In general, the reaction mixture is concentrated in the presence of Florisil and then chromatographed using a mixture of n-hexane and ethyl acetate.

Process (C)

The formula (IV) provides a general definition of the amides required as starting materials for carrying out the process (C) according to the invention. In this formula R$^1$, R$^2$, R$^3$ and Het preferably, particularly preferably very particularly preferably and especially preferably have those meanings which have already been mentioned in connection with the description of the compounds of the formula (I) according to the invention as being preferred, particularly preferred, etc., for these radicals. R$^{19}$ preferably represents C$_1$–C$_4$-alkyl, C$_1$–C$_4$-halogenoalkyl, phenyl or arylalkyl, particularly preferably methyl, ethyl, phenyl or benzyl, very particularly preferably methyl, phenyl or benzyl.

Amides of the formula (IV) are novel. They can be prepared by
i) reacting cyclopropanes of the formula (XVII)

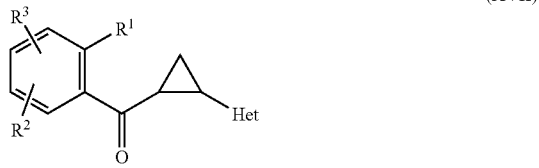

in which
R¹, R², R³ and Het have the meanings given above
with a nitrile of the formula (XXI)

in which
R¹⁹ has the meanings given above
in the presence of a protonic acid (for example sulphuric acid) if appropriate in the presence of a diluent.

The cyclopropanes of the formula (XVII) required as starting materials for carrying out the process (i) have already been described in connection with the explanation of the process (B) according to the invention.

The formula (XXI) provides a general definition of the nitriles required as starting materials for carrying out the process (i). In this formula, R¹⁹ preferably, particularly preferably, very particularly preferably and especially preferably has those meanings which have already been mentioned in connection with the description of the compounds of the formula (IV) as being preferred, particularly preferred, etc. for these radicals.

When carrying out the process (C) according to the invention, protonic acids (cf. J. Org. Chem. 1978, 43, 4593), inorganic bases (cf. J. Chem. Soc. 1964, 4142), hydrazines (cf. J. Org. Chem. 1978, 43, 3711) or biotransformations with enzymes (cf. Appl. Microbiol. Biotechnol. 1997, 47, 650) are used for N-deacylating the amides of the formula (IV) during the conversion into pyrrolines of the formula (I). Other customary processes for deacetylating amides have been described in T. W. Greene, P. G. M. Wuts, Protective Groups in Organic Synthesis (Ed. 3, New York, Wiley 1999, pp. 553–555).

Preferred N-deacetylating agents are protonic acids or organic acids, particularly preferably aqueous hydrochloric acid, aqueous hydrobromic acid or trifluoroacetic acid, very particularly preferably aqueous hydrochloric acid; preferably inorganic bases, particularly preferably barium hydroxide [Ba(OH)₂] and sodium hydroxide (NaOH) and preferably biotransformations, particularly preferably with the use of acylases.

If the N-deacylation is carried out using biotransformations, the compounds of the formula (I) are obtained in a form where one of the two enantiomers is present in excess.

Suitable diluents for carrying out the process (C) according to the invention are water or alcohols and mixtures of these. Preference is given to using water, methanol or ethanol or mixtures of two or three of these three diluents.

When carrying out the process (C) according to the invention, the reaction temperatures can be varied within a relatively wide range. In general, the process is carried out at temperatures between 20° C. and 200° C., preferably between 60° C. and 140° C., particularly preferably between 80° C. and 120° C. If the N-deacylation is carried out enzymatically using acylases, the process is generally carried out at temperatures between 20° C. and 60° C., preferably between 20° C. and 40° C.

When carrying out the process (C) according to the invention, in general 2 parts by volume of a protonic acid are employed per part by volume of a 10% strength (w/v) alcoholic solution of the amide of the formula (IV). However, it is also possible to choose other ratios of the reaction components. Work-up is carried out by customary methods. In general, the reaction mixture is neutralized with aqueous sodium hydroxide solution and then extracted with ethyl acetate and the organic phase is dried, filtered and concentrated.

Process (D)

In a first reaction step, a compound of the formula (I-b) is coupled with a diboronic acid ester in the presence of a palladium catalyst, if appropriate in the presence of an acid binder and if appropriate in the presence of a solvent. Without any isolation of the intermediate, a compound of the formula (V) is coupled in the same reaction vessel in a second reaction step in the presence of a catalyst, if appropriate in the presence of an acid binder and if appropriate in the presence of a solvent (cf., for example, Tetrahedron Lett. 1997, 38, 3841).

The process (D) according to the invention can be carried out in two variants. It is possible either to initially charge a compound of the formula (I-b) or to initially charge a compound of the formula (V). Process (D) is to be considered a tandem reaction of the processes E) and (F) described below.

The formula (I-b) provides a general definition of the Δ¹-pyrrolines required as starting materials for carrying out the process (D) according to the invention. In this formula R¹, R² and R³ preferably, particularly preferably, very particularly preferably and especially preferably have those meanings which have already been mentioned in connection with the description of the compounds of the formula (I) according to the invention as being preferred, particularly preferred, etc., for these radicals. Het² preferably represents 5- to 14-membered heteroaryl which comprises 1 to 3 aromatic rings and one or more heteroatoms from the group consisting of nitrogen, oxygen and sulphur and which is monosubstituted by R⁵⁻². Het² particularly preferably represents 5- to 14-membered heteroaryl which comprises 1 to 3 aromatic rings and 1 to 4 heteroatoms including 0 to 4 nitrogen atoms, 0 to 2 nonadjacent oxygen atoms and/or 0 to 2 nonadjacent sulphur atoms (in particular thienyl, benzothienyl, furyl, benzofuryl, indolyl, thienothienyl, thienofuryl, thienobenzothienyl, thienobenzofuryl, pyridinyl, pyrimidinyl, pyridazinyl, pyrazinyl, triazolyl or tetrazolyl) which is monosubstituted by R⁵⁻². Het² very particularly preferably represents 2-thienyl, 3-thienyl, 2-benzo[b]thienyl, 2-furyl, 3-furyl, 2-benzo[b]furyl, 2-indolyl, 2-thieno[3,2-b]thienyl, 2-thieno[3,2-b]furyl, 5-thieno[3,2-b]furyl, 2-thieno[2,3-f][1]benzothienyl, 2-thieno[2,3-f][1]benzofuryl, 6-thieno[2,3-f][1]benzofuryl, 2-pyridinyl, 3-pyridinyl, 2-pyrimidinyl, 5-pyrimidinyl, 3-pyridazinyl, 4-pyridazinyl, 2-pyrazinyl, triazolyl or tetrazolyl which is monosubstituted by R⁵⁻². Het² especially preferably represents 2-thienyl, 3-thienyl, 2-benzo[b]thienyl, 2-furyl, 3-furyl, 2-benzo[b]furyl, 2-thieno[3,2-b]thienyl, 2-thieno[3,2-b]furyl, 5-thieno[3,2-b]furyl, 2-thieno[2,3-f][1]benzothienyl, 2-thieno[2,3-f][1]benzofuryl, 6-thieno[2,3-f][1]benzofuryl, 2-pyridinyl, 3-pyridinyl, 2-pyrimidinyl, 5-pyrimidinyl, 3-pyridazinyl, 4-pyridazinyl or 2-pyrazinyl which is monosubstituted by R⁵⁻². R⁵⁻² preferably represents bromine, iodine —OSO₂CF₃ or —OSO$_2$(CF$_2$)$_3$CF$_3$, particularly preferably bromine, —OSO$_2$CF$_3$ or —OSO$_2$(CF$_2$)$_3$, very particularly preferably bromine or —OSO$_2$CF$_3$.

Δ$^1$-Pyrrolines of the formula (I-b) form part of the subject-matter of the present invention and can be prepared by one of the processes (A), (B) or (C).

The formula (V) provides a general definition of the heterocycles required as starting materials for carrying out the process (D) according to the invention. In this formula E preferably, particularly preferably, very particularly preferably and especially preferably has those meanings which have already been mentioned in connection with the description of the compounds of the formula (I) according to the invention as being preferred, particularly preferred, etc., for these radicals. Y$^1$ preferably represents phenylene or 5- to 10-membered saturated or unsaturated heterocyclylene having one or more heteroatoms from the group consisting of nitrogen, oxygen and sulphur, each of which radicals is optionally mono- to tetrasubstituted by identical or different radicals from the list W$^1$. Y$^1$ particularly preferably represents 1,4-phenylene, 1,3-phenylene or 1,2-phenylene, each of which is optionally mono- to tetrasubstituted by identical or different radicals from the list W$^1$; or represents 5- to 6-membered saturated or unsaturated heterocyclylene having 1 to 3 heteroatoms including 0 to 3 nitrogen atoms, 0 to 2 nonadjacent oxygen atoms and 0 to 2 nonadjacent sulphur atoms (in particular furylene, thienylene, pyrrolylene, oxazolylene, thiazolylene, pyridinylene, pyrimidinylene, pyridazinylene or pyrazinylene), each of which radicals is optionally mono- to tetrasubstituted by identical or different radicals from the list W$^1$. Y$^1$ very particularly preferably represents 1,4-phenylene, 1,3-phenylene, 1,2-phenylene, 2,4-furylene, 2,4-thienylene, 2,4-pyrrolylene, 2,5-oxazolylene, 2,5-thiazolylene, 2,5-pyridinylene, 2,6-pyridinylene, 2,5-pyrimidinylene, 3,6-pyridazinylene or 2,5-pyrazinylene each of which is optionally mono- to trisubstituted by identical or different radicals from the list W$^1$. Y$^1$ especially preferably represents 1,4-phenylene, 1,3-phenylene, 2,4-furylene, 2,4-thienylene, 2,5-pyridinylene, 2,5-pyrimidinylene, 3,6-pyridazinylene or 2,5-pyrazinylene each of which is optionally mono- or disubstituted by identical or different radicals from the list W$^1$. W$^1$ preferably, particularly preferably, very particularly preferably and especially preferably has those meanings which have already been mentioned in connection with the description of the compounds of the formula (I) according to the invention as being preferred, particularly preferred, etc., for these radicals. A$^1$ preferably represents bromine, chlorine, iodine or —OSO$_2$CF$_3$ particularly preferably bromine, chlorine or iodine, very particularly preferably bromine or chlorine.

The heterocycles of the formula (V) are known or can be prepared by known processes (cf. Aust. J. Chem. 1964, 17, 794; Chem. Ber. 1992, 125, 1169; Chem. Pharm. Bull. 1995, 43, 247; Eur. J. Med. Chem. 1989, 24, 249; J. Chem. Soc. C 1971, 1889; J. Chem. Soc. Perkin Trans. 1 1995, 2497; J. Med. Chem. 1991, 34, 315; J. Org. Chem. 1984, 49, 2240; J. Org. Chem. 1990, 55, 69; Org. Prep. Proced. Int. 1998, 30, 433; Synthesis 1999, 1163; Tetrahedron 1999, 40, 7975; Tetrahedron Lett. 1996, 37, 4447; Tetrahedron Lett. 2000, 41, 4335).

Suitable diboronic acid esters for carrying out the process (D) according to the invention are 4,4,4',4',5,5,5',5'-octamethyl-2,2'-bis-1,3,2-dioxaborolane, 5,5,5',5'-tetramethyl-2,2'-bis-1,3,2-dioxaborinane, 4,4,4',4',6,6'-hexamethyl-2,2'-bis-1,3,2-dioxaborinane or 2,2'-bis-1,3,2-benzodioxaborole. Preference is given to using 4,4,4',4',5,5,5',5'-octamethyl-2,2'-bis-1,3,2-dioxaborolane, 5,5,5',5'-tetramethyl-2,2'-bis-1,3,2-dioxaborinane or 4,4,4',4',6,6'-hexamethyl-2,2'-bis-1,3,2-dioxaborinane, particularly preferably 4,4,4',4',5,5,5',5'-octamethyl-2,2'-bis-1,3,2-dioxaborolane or 5,5,5',5'-tetramethyl-2,2'-bis-1,3,2-dioxaborinane, very particularly preferably 4,4,4',4',5,5,5',5'-octamethyl-2,2'-bis-1,3,2-dioxaborolane.

When carrying out the process (D) according to the invention, in general 1 mol or a slight excess of a diboronic ester and 1 mol or a slight excess of a compound of the formula (V), and 3% of a palladium catalyst, are employed per mole of the compound of the formula (I-b). However, it is also possible to employ the reaction components in other ratios. It is possible to initially charge the compound of the formula (I-b) or, alternatively, the compound of the formula (V). Work-up is carried out by customary methods. In general, the reaction, mixture is diluted with water and extracted with ethyl acetate. The organic phase is washed, dried, filtered and concentrated. The residue is, if appropriate, freed from any impurities that may still be present using customary methods, such as chromatography or recrystallization.

Process (E)

The formula (VI) provides a general definition of the Δ$^1$-pyrrolines required as starting materials for carrying out the process (E) according to the invention. In this formula R$^1$, R$^2$ and R$^3$ preferably, particularly preferably, very particularly preferably and especially preferably have those meanings which have already been mentioned in connection with the description of the compounds of the formula (I) as being preferred, particularly preferred etc., for these radicals. Het$^3$ preferably represents 5- to 14-membered heteroaryl which comprises 1 to 3 aromatic rings and one or more heteroatoms from the group consisting of nitrogen, oxygen and sulphur and is monosubstituted by A$^2$. Het$^3$ particularly preferably represents 5- to 14-membered heteroaryl which comprises 1 to 3 aromatic rings and 1 to 4 heteroatoms including 0 to 4 nitrogen atoms, 0 to 2 nonadjacent oxygen atoms and/or 0 to 2 nonadjacent sulphur atoms (in particular thienyl, benzothienyl, furyl, benzofuryl, indolyl, thienothienyl, thienofuryl, thienobenzothienyl, thienobenzofuryl, pyridinyl, pyrimidinyl, pyridazinyl, pyrazinyl, triazolyl or tetrazolyl), which radicals are monosubstituted by A$^2$. Het$^3$ very particularly preferably represents 2-thienyl, 3-thienyl, 2-benzo[b]thienyl, 2-furyl, 3-furyl, 2-benzo[b]furyl, 2-indolyl, 2-thieno[3,2b]thienyl, 2-thieno[3,2-b]furyl, 5-thieno[3,2-b]furyl, 2-thieno[2,3-f][1]benzothienyl, 2-thieno[2,3-f][1]benzofuryl, 6-thieno[2,3-f][1]benzofuryl, 2-pyridinyl, 3-pyridinyl, 2-pyrimidinyl, 5-pyrimidinyl, 3-pyridazinyl, 4-pyridazinyl, 2-pyrazinyl, triazolyl or tetrazolyl which is monosubstituted by A$^2$. Het$^3$ especially preferably represents 2-thienyl, 3-thienyl, 2-benzo[b]thienyl, 2-furyl, 3-furyl, 2-benzo[b]furyl, 2-thieno[3,2-b]thienyl, 2-thieno[3,2-b]furyl, 5-thieno[3,2-b]furyl, 2-thieno[2,3-f][1]benzothienyl, 2-thieno[2,3-f][1]benzofuryl, 6-thieno[2,3-f][1]benzofuryl, 2-pyridinyl, 3-pyridinyl, 2-pyrimidinyl, 5-pyrimidinyl, 3-pyridazinyl, 4-pyridazinyl or 2-pyrazinyl which is monosubstituted by A$^2$. A$^2$ preferably represents —B(OH)$_2$, (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxaborol-2-yl, particularly preferably —B(OH)$_2$, (4,4,5,5-tetramethyl-1,3,2-dioxaborolan)-2-yl, (5,5-dimethyl-1,3,2-dioxaborinan)-2-yl or (4,4,6-trimethyl-1,3,2-dioxaborinan)-2-yl, very particularly preferably —B(OH)$_2$, (4,4,5,5-tetramethyl-1,3,2-dioxaborolan)-2-yl, (5,5-dimethyl-1,3,2-dioxaborinan)-2-yl.

$\Delta^1$-Pyrrolines of the formula (VI) can be prepared by
k) reacting compounds of the formula (I-b)

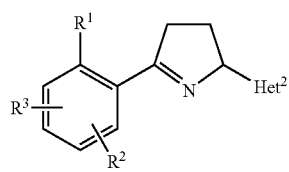

(I-b)

in which
R$^1$, R$^2$, R$^3$ and Het$^2$ have the meanings given above,
with a diboronic acid ester in the presence of a catalyst, if appropriate in the presence of an acid binder and if appropriate in the presence of a diluent (cf. J. Org. Chem. 1995, 60, 7508; Tetrahedron Lett. 1997, 38, 3447).

Diboronic acid esters suitable for carrying out the process (k) have already been mentioned in the description of the process (D) according to the invention.

The heterocycles of the formula (V) required as starting materials for carrying out the process (E) according to the invention have already been described above in the description of the process (D).

When carrying out the process (E) according to the invention, in general 1 mol or a slight excess of a compound of the formula (V) is employed per mole of the compound of the formula (VI). However, it is also possible to employ the reaction components in other ratios. Work-up is carried out by customary methods. In general, the reaction mixture is taken up in ethyl acetate and the organic phase is washed with water, dried over sodium sulphate, filtered and concentrated. The residue is, if appropriate, freed from any impurities that may still be present using customary methods, such as chromatography or recrystallization.

Process (F)

The $\Delta^1$-pyrrolines of the formula (I-b) required as starting materials for carrying out the process (F) according to the invention have already been described in the description of the process (D).

The formula (VII) provides a general definition of the boronic acid derivatives required as starting materials for carrying out the process (F) according to the invention. In this formula, E preferably, particularly preferably, very particularly preferably and especially preferably has those meanings which have already been mentioned in connection with the description of the compounds of the formula (I) according to the invention as being preferred, particularly preferred, etc., for these radicals. Y$^1$ preferably, particularly preferably, very particularly preferably and especially preferably has those meanings which have already been mentioned in connection with the description of the compounds of the formula (V) as being preferred, particularly preferred, etc., for these radicals. A$^2$ preferably, particularly preferably, very particularly preferably and especially preferably has those meanings which have already been mentioned in connection with the description of the compounds of the formula (VI) as being preferred, particularly preferred, etc., for these radicals.

The compounds of the formula (VII) are known or can be prepared by known processes (cf. J. Org. Chem. 1995, 60, 7508, Tetrahedron Lett. 1997, 38, 3447).

When carrying out the process (F) according to the invention, in general 1 mol or a slight excess of a compound of the formula (VII) is employed per mole of the compound of the formula (I-b). However, it is also possible to employ the reaction components in other ratios. Work-up is carried out by customary methods. In general, the reaction mixture is taken up in ethyl acetate and the organic phase is washed with water, dried over sodium sulphate, filtered and concentrated. The residue is, if appropriate, freed from any impurities that may still be present using customary methods, such as chromatography or recrystallization.

Process (G)

The formula (I-c) provides a general definition of the $\Delta^1$-pyrrolines required as starting materials for carrying out the process (G) according to the invention. In this formula R$^1$, R$^2$ and R$^3$ preferably, particularly preferably, very particularly preferably and especially preferably have those meanings which have already been mentioned in connection with the description of the compounds of the formula (I) according to the invention as being preferred, particularly preferred, etc., for these radicals. Het$^4$ preferably represents 5- to 14-membered heteroaryl which comprises 1 to 3 aromatic rings and one or more heteroatoms from the group consisting of nitrogen, oxygen and sulphur and is substituted by R$^{5-3}$. Het$^4$ particularly preferably represents 5- to 14-membered heteroaryl having 1 to 4 heteroatoms including 0 to 4 nitrogen atoms, 0 to 2 nonadjacent oxygen atoms and/or 0 to 2 nonadjacent sulphur atoms (in particular thienyl, benzothienyl, furyl, benzofuryl, indolyl, thienothienyl, thienofuryl, thienobenzothienyl, thienobenzofuryl, pyridinyl, pyrimidinyl, pyridazinyl, pyrazinyl, triazolyl or tetrazolyl), which radicals are monosubstituted by R$^{5-3}$. Het$^4$ very particularly preferably represents 2-thienyl, 3-thienyl, 2-benzo[b]thienyl, 2-indolyl, 2-furyl, 3-furyl, 2-benzo[b]furyl, 2-thieno[3,2-b]thienyl, 2-thieno[3,2-b]furyl, 5-thieno[3,2-b]furyl, 2-thieno[2,3-f][1]benzothienyl, 2-thieno[2,3-f][1]benzofuryl, 6-thieno[2,3-f][1]benzofuryl, 2-pyridinyl, 3-pyridinyl, 2-pyrimidinyl, 5-pyrimidinyl, 3-pyridazinyl, 4-pyridazinyl, 2-pyrazinyl, triazolyl or tetrazolyl which is monosubstituted by R$^{5-3}$. Het$^4$ especially preferably represents 2-thienyl, 3-thienyl, 2-benzo[b]-thienyl, 2-furyl, 3-furyl, 2-benzo[b]furyl, 2-thieno[3,2-b]thienyl, 2-thieno[3,2-b]furyl, 5-thieno[3,2-b]furyl, 2-thieno[2,3-f][1]benzothienyl, 2-thieno[2,3-f][1]benzofuryl, 6-thieno[2,3-f][1]benzofuryl, 2-pyridinyl, 3-pyridinyl, 2-pyrimidinyl, 5-pyrimidinyl, 3-pyridazinyl, 4-pyridazinyl or 2-pyrazinyl which is monosubstituted by R$^{5-3}$. R$^{5-3}$ preferably represents bromine or iodine.

$\Delta^1$-Pyrrolines of the formula (I-c) form part of the subject-matter of this invention and can be prepared by one of the processes (A), (B) or (C).

The formula (VIII) provides a general definition of the organometallic compounds required as starting materials for carrying out the process (G) according to the invention. In this formula, E preferably, particularly preferably, very particularly preferably and especially preferably has those meanings which have already been mentioned in connection with the description of the compounds of the formula (I) according to the invention as being preferred, particularly preferred, etc., for these radicals. In this formula, Y$^1$ preferably, particularly preferably, very particularly preferably and especially preferably has those meanings which have already been mentioned in connection with the description of the compounds of the formula (V) as being preferred, particularly preferred, etc., for these radicals. M preferably represents ZnCl, Sn(Me)$_3$ or Sn(n-Bu)$_3$.

Some of the organometallic compounds of the formula (VIII) are known, and/or they can be prepared by known methods. It is possible, for example, to prepare compounds of the formula (VIII) in situ from the corresponding compounds of the formula (V) in which $A^1$ represents —$OSO_2CF_3$ (cf. Tetrahedron Lett. 1995, 36, 9085).

When carrying out the process (G) according to the invention, in general 1 mol or a slight excess of a compound of the formula (VIII) is employed per mole of the compound of the formula (I-c). However, it is also possible to employ the reaction components in other ratios. Work-up is carried out by customary methods. In general, the reaction mixture is taken up in ethyl acetate and the organic phase is washed with water, dried over sodium sulphate, filtered and concentrated. The residue is, if appropriate, freed from any impurities that may still be present using customary methods, such as chromatography or recrystallization.

When carrying out the processes (D), (E), (F) and (G) according to the invention, in each case a palladium catalyst is employed, which for its part can be used with or without addition of further ligands. The catalyst used is preferably $PdCl_2(dppf)$ [dppf=1,1'-bis(diphenylphosphino)ferrocene], $Pd(PPh_3)_4$, $PdCl_2(PPh_3)_2$, $PdCl_2(CH_3CN)_2$, $Pd_2(dba)_3$ [dba=dibenzylideneacetone] or $Pd(OAc)_2$, particularly preferably $PdCl_2(dppf)$, $Pd(PPh_3)_4$, $PdCl_2(PPh_3)_2$, or $Pd(OAc)_2$, very particularly preferably $PdCl_2(dppf)$ or $PdCl_2(PPh_3)_2$.

Suitable ligands are triarylphosphines; trialkylphosphines or arsines. Preference is given to using dppf, $PPh_3$, $P(t-Bu)_3$, $Pcy_3$ or $AsPh_3$, particularly preferably dppf.

Suitable diluents for carrying out the processes (D), (E) and (F) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide or sulphones, such as sulpholane. Particular preference is given to using acetone, dimethoxyethane, dioxane, tetrahydrofuran, dimethylformamide, dimethylacetamide, dimethyl sulphoxide, ethanol, toluene or, if appropriate, mixtures of the diluents mentioned with water.

Suitable diluents for carrying out the process (G) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decaline; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole. Particular preference is given to using dioxane, tetrahydrofuran or toluene.

Suitable acid binders for carrying out the processes (D), (E), (F) and (G) according to the invention are in each case all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, alkali metal fluorides, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). However, it is also possible to operate without additional acid binder, or to employ an excess of the amine component, so that it simultaneously acts as acid binder. Barium hydroxide, sodium hydroxide, potassium hydroxide, tripotassium phosphate, caesium carbonate, potassium carbonate, sodium carbonate, potassium acetate, triethylamine, potassium tert-butoxide, caesium fluoride or potassium fluoride are used with particular preference., When carrying out the processes (D), (E) and (F), the reaction temperatures can in each case be varied within a relatively wide range. In general, the reactions are carried out at temperatures between 0° C. and 140° C., preferably between 20° C. and 120° C., particularly preferably between 60° C. and 100° C.

When carrying out the process (G) according to the invention, the reaction temperatures can in each case be varied within a relatively wide range. In general, the reaction is carried out at temperatures between 0° C. and 140° C., preferably between 20° C. and 120° C.

Chiral Compounds of the Formula (I-d)

To prepare chiral compounds of the formula (I-d), it is possible, for example, to subject $\Delta^1$-pyrrolines of the formula (I-e)

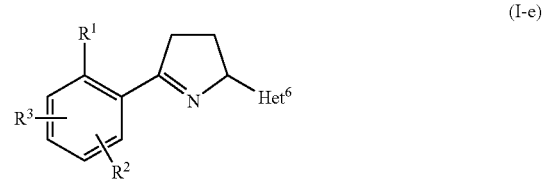

(I-e)

in which
$R^1$, $R^2$ and $R^3$ have the meanings given above,
$Het^6$ represents heteroaryl which is monosubstituted by $R^{5-4}$ and
$R^{5-4}$ represents chlorine, bromine or iodine to an optical resolution. However, it is also possible to use other compounds of the formula (I) according to the invention. To this end, for example, methods of preparative chromatography, preferably the high performance liquid chromatography (HPLC) method, are employed. Here, a chiral stationary silica gel phase is used. A tris-(3,5-dimethylphenylcarbamate)-cellulose-modified silica gel has been found to be particularly suitable for separating the compounds of the formula (I-e) into the two enantiomers. This separating material is commercially available. However, it is also possible to use other stationary phases. Suitable mobile phases are all customary inert organic solvents, and mixtures of these. Preference is given to using optionally halogenated aliphatic, alicyclic or aromatic hydrocarbons, such as petroleum ether, hexane, heptane, cyclohexane; dichloromethane, chloroform; alcohols, such as methanol, ethanol, propanol;

nitriles, such as acetonitrile; esters, such as methyl acetate or ethyl acetate. Particular preference is given to using aliphatic hydrocarbons, such as hexane or heptane, and alcohols, such as methanol or propanol, very particularly preferably n-heptane and isopropanol or mixtures of these.

In general, the separation is carried out at temperatures between 10° C. and 60° C., preferably between 10° C. and 40° C., particularly preferably at room temperature.

$\Delta^1$-Pyrrolines of the formula (I-e) form part of the subject-matter of this invention and can be prepared by one of the processes (A), (B) or (C). The (R)-configured enantiomers obtained in this manner are then used as starting materials for the processes (D), (F) or (G).

All of the processes according to the invention are generally carried out under atmospheric pressure. However, in each case it is also possible to operate under elevated or reduced pressure.

The active compounds, according to the invention, having good plant tolerance and favourable warm-blood toxicity, are suitable for controlling animal pests, in particular insects, arachnids and nematodes, which are encountered in agriculture, in forestry, in the protection of stored products and of materials, and in the hygiene sector. They may be preferably used as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera., for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporaniorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium comi, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Omithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

The compounds of the formula (I) according to the invention are particularly effective against caterpillars, beetle larvae, spider mites, aphids and leaf-mining flies.

At certain concentrations or application rates, the compounds according to the invention may, if appropriate, also be used as herbicides and microbicides, for example as fungicides, antimycotics and bactericides. If appropriate, they may also be used as intermediates or precursors for the synthesis of further active compounds.

All plants and plant parts can be treated in accordance with the invention. Plants are to be understood as meaning in the present context all plants and plant populations such as desired and undesired wild plants or crop plants (inclusive of naturally occurring crop plants). Crop plants can be plants which can be obtained by conventional plant breeding and optimization methods or by biotechnological and recombinant methods or by combinations of these methods, inclusive of the transgenic plants and inclusive of the plant cultivars protectable or not protectable by plant breeders' rights. Plant parts are to be understood to mean all aboveground and underground parts and organs of plants, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on their surroundings, environment or storage space by the customary treatment methods, for example by immersion, spraying, evaporation, fogging, scattering, painting on and, in the case of propagation material, in particular in the case of seeds, also by applying one or more coats.

The active compounds can be converted into the customary formulations, such as solutions, emulsions, wettable powders, suspensions, powders, dusts, pastes, soluble powders, granules, suspension-emulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are:

for example ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and, also protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyes, such as alizarin dyes, azo dyes and metal phthalocyanine dyes, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilizing agenis, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable examples of co-components in mixtures are the following compounds:

Fungicides:
aldimorph, ampropylfos, ampropylfos-potassium, andoprim, anilazine, azaconazole, azoxystrobin,
benalaxyl, benodanil, benomyl, benzamacril, benzamacril-isobutyl, bialaphos, binapacryl, biphenyl, bitertanol, blasticidin-S, bromuconazole, bupirimate, buthiobate,
calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
guazatine,
hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozplin, nickel dimethyldithiocarbamate, nitrothal-isopropyl, nuarimol, ofurace, oxadixyl, oxamocarb, oxolinic acid, oxycarboxim; oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705, OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidinedione, 1-[(diiodomethyl)-sulphonyl]4-methyl-benzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2,4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinol, 2',6'-dibromo-2-methyl-4'-trifluoromethoxy-4'-trifluoromethyl-1,3-thiazole-5-carboxanilide, 2,2-dichloro-N-[1-(4-chlorophenyl)-ethyl]-1-ethyl-3-methyl-cyclopropanecarboxamide, 2,6-dichloro-5-(methylthio)-4-pyrimidinyl-thiocyanate, 2,6-dichloro-N-(4-trifluoromethylbenzyl)-benzamide, 2,6-dichloro-N-[[4-(trifluoromethyl)-phenyl]-methyl]-benzamide, 2-(2,3,3-triiodo-2-propenyl)-2H-tetrazole, 2-[(1-methylethyl)-sulphonyl]-5-(trichloromethyl)-1,3,4-thiadiazole, 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile, 2-aminobutane, 2-bromo-2-(bromomethyl)-pentanedinitrile, 2-chloro-N-(2,3-dihydro-1,1,3-trimethyl-1H-inden-4-yl)-3-pyridinecarboxamide, 2-chloro-N-(2,6-dimethylphenyl)-N-(isothiocyanatomethyl)-acetamide, 2-phenylphenol (OPP), 3,4-dichloro-1-[4-(difluoromethoxy)-phenyl]-1H-pyrrole-2,5-dione, 3,5-dichloro-N-[cyano-[(1-methyl-2-propynyl)-oxy]-methyl]-benzamide, 3-(1,1-dimethylpropyl)-1-oxo-1H-indene-2-carbonitrile, 3-[2-(4-chlorophenyl)-5-ethoxy-3-isoxazolidinyl]-pyridine, 4-chloro-2-cyano-N,N-dimethyl-5-(4-methylphenyl)-1H-imidazole-1-sulphonamide, 4-methyl-tetrazolo[1,5-a]quinazolin-5(4H)-one, 8-(1,1-dimethylethyl)-N-ethyl-N-propyl-1,4-dioxaspiro[4.5]decane-2-methanamine, 8-hydroxyquinoline sulphate, 9H-xanthene-2-[(phenylamino)-carbonyl]-9-carboxylic hydrazide, bis-(1-methylethyl)-3-methyl-4-[(3-methylbenzoyl)-oxy]-2,5-thiophenedicarboxylate, cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholinehydrochloride, ethyl [(4-chlorophenyl)-azo]-cyanoacetate, potassium hydrogen carbonate, methanetetrathiol sodium salt, methyl 1-(2,3-dihydro-2,2-dimethyl-1H-inden-1-yl)-1H-imidazole-5-carboxylate, methyl N-(2,6-dimethylphenyl)-N-(5-isoxazolylcarbonyl)-DL-alaninate, methyl N-(chloroacetyl)-N-(2,6-dimethylphenyl)-DL-alaninate, N-(2,3-dichloro-4-hydroxyphenyl)-1-methyl-cyclohexanecarboxamide, N-(2,6-dimethylphenyl-2-methoxy-N-(tetrahydro-2-oxo-3-furanyl)-acetamide, N-(2,6-dimethylphenyl)-2-methoxy-N-(tetrahydro-2-oxo-3-thienyl)-acetamide, N-(2-chloro-4-nitrophenyl)-4-methyl-3-nitro-benzene-sulphonamide, N-(4-cyclohexylphenyl)-1,4,5,6-tetrahydro-2-pyrimidinamine, N-(4-hexylphenyl)-1,4,5,6-tetrahydro-2-pyrimidinamine, N-(5-chloro-2-methylphenyl)-2-methoxy-N-(2-oxo-3-oxazolidinyl)-acetamide, N-(6-methoxy)-3-pyridinyl)-cyclopropanecarboxamide, N-[2,2,2-trichloro-1-[(chloroacetyl)-amino]-ethyl]-benzamide, N-[3-chloro-4,5-bis-(2-propinyloxy)-phenyl]-N'-methoxy-methanimidamide, N-formyl-N-hydroxy-DL-alanine sodium salt, O,O-diethyl [2-(dipropylamino)-2-oxoethyl]-ethylphosphoramidothioate, O-methyl S-phenyl phenylpropylphosphoramidothioate, S-methyl 1,2,3-benzothiadiazole-7-carbothioate, spiro[2H]-1-benzopyrane-2,1'(3'H)-isobenzofuran-3'-one.

Bactericides:

bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:

abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis,* Baculoviruses, *Beauveria bassiana, Beauvena tenella,* bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cis-permethrin, clocythrin, cloethocarb, clofentezine, clothianidine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, *Entomopfthora* spp., eprinomectin, esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathion, ivermectin, nuclear polyhedrosis viruses, lambda-cyhalothrin, lufenuron, malathion, mecarbam, metaldehyde, methamidophos, metharhizium anisopliae, metharhizium flavoviride, methidathion, methiocarb, methomyl, methoxyfenozide, metolcarb, metoxadiazone, mevinphos, milbemectin, monocrotophos, naled, nitenpyram, nithiazine, novaluron, omethoate, oxamyl, oxydemethon M,

*Paecilomyces fumosoroseus,* parathion A, parathion M, permethrin, phenthoate, phorate, phosalone, phosmet, phosphamidon, phoxim, pirimicarb; pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, selamectin, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazurone, trichlophenidine, tnichlorfon, triflumuron, trimethacarb, vamidothion, vaniliprole, *Verticillium lecanii,*

YI 5302, zeta-cypermethrin, zolaprofos, (1R-cis)-[5-(phenylmethyl)-3-furanyl]-methyl 3-[(dihydro-2-oxo-3(2H)-furanylidene)-methyl]-2,2-dimethylcyclopropanecarboxylate, (3-phenoxyphenyl)-methyl 2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(H)-pyridazinone, 4-chloro-5-[(6-chloro-3-pyridinyl)methoxy]-2-(3,4-dichlordphenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1—oxaspiro [4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

A mixture with other known active compounds, such as herbicides, or with fertilizers and growth regulators is also possible.

The active compounds according to the invention can furthermore be present when used as insecticides in their commercially available formulations and in the use forms, prepared from these formulations, as a mixture with synergistic agents.

Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having certain properties ("traits") which have been obtained by conventional breeding, by mutagenesis or by recombinant DNA techniques. This can be varieties, bio- and genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant cultivars (i.e. those obtained by genetic engineering) which are preferred according to the invention include all plants which, in the genetic modification, received genetic material which imparted particularly advantageous useful traits to these plants. Examples of such traits are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitous and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still-to-be-developed genetic traits, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants.

Particular emphasis is given to the treatment of plants with the compounds or the mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphhonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattela germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

These are highly effective, for example, against the development stages of ticks, for example *Amblyomma hebraeum*, against parasitic flies, for example against *Lucilia cuprina*, and against fleas, for example against *Ctenocephalides felis*.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) according to the invention can be used as formulations (for example, powders, emulsions, free-flowing compositions), which comprise the active compounds according to the invention in an amount of 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as being preferred—but without any limitation:

Beetles, such as
*Hylotrupes bajulus, Chlorophorus pilosis, Anobium punctatum, Xestobium rufdvillosum, Ptilinus pecticornis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec. and *Dinoderus minutus*.

Hymenopterons, such as
*Sirex juvencus, Urocerus gigas, Urocerus gigas taignus* and *Urocerus augur.*

Termites, such as
*Kalotermes flavicollis, Cryptotermes brevis, Heterotermes indicola, Reticuliterrnes flavipes, Reticulitermes santonensis, Reticulitermes lucifugus, Mastotermes darwiniensis, Zootermopsis nevadensis* and *Coptotermes formosanus.*

Bristletails, such as *Lepisma saccharina*.

Industrial materials in the present context are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising this are to be understood as meaning, for example:
building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compounds according to the invention can be used as such, in the form of concentrates or in generally customary formulations, such as powders, granules, solutions, suspensions, emulsions or pastes.

The formulations mentioned can be prepared in a manner known per se, for example by mixing the active compounds according to the invention with at least one solvent or diluent, emulsifier, dispersing agent and/or binder or fixing agent, a water repellent, if appropriate siccatives and UV stabilizers and if appropriate dyes and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., turpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace. 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypernethrin, deltamethrin, permethrin, imidacloprid, NI-25, flufenoxuron, hexaflumuron, transfluthrin, thiacloprid, methoxyphenoxide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects which come into contact with salt water or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis-(trialkyltin) sulphides, tri-n-butyltin laurate, tri-n-butyltin chloride, copper(I) oxide, triethyltin chloride, tri-n-butyl-(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthio-carbamate, zinc dimethyldithio-carbamate, zinc ethylenebisthiocarbamate, zinc salts and copper salts of 2-pyridinethiol 1-oxide, bisdimethyldithio-carbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

Algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

Fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

Molluscicides such as
fentin acetate, metaldehyde, methiocarb, niclosamid, thiodicarb and trimethacarb; or conventional antifouling active compounds such as
4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed-oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed in domestic insecticide products for controlling these pests alone or in combination with other active compounds and auxiliaries. They are active against sensitive and resistant species and against all development stages.

These pests include:
From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus* and *Dermatophagoides forinae*.

From the order of the Araneae, for example, *Aviculariidae* and *Araneidae*.

From the order of the Opiliones, for example, *Pseudoscorpiones chelifer, Pseudoscorpiones cheiridium* and *Opiliones phalangium*.

From the order of the Isopoda, for example, *Oniscus asellus* and *Porcellio scaber*.

From the order of the Diplopoda, for example, *Blaniulus guttulatus* and *Polydesmus* spp.

From the order of the Chilopoda, for example, *Geophilus* spp.

From the order of the Zygentoma, for example, *Ctenolepisma* spp., *Lepisma saccharina* and *Lepismodes inquilinus*.

From the order of the Blattaria, for example, *Blatta orientalies, Blattella germanica, Blattella asahinai, Leucophaea maderae, Panchlora* spp., *Parcoblatta*, spp., *Periplaneta australasiae, Periplaneta americana, Periplaneta brunnea, Periplarieta fuliginosa* and *Supella longipalpa*.

From the order of the Saltatoria, for example, *Acheta domesticus*.

From the order of the Dermaptera, for example, *Forficula auricularia*.

From the order of the Isoptera, for example, *Kalotermes* spp. and *Reticulitermes* spp.

From the order of the Psocoptera, for example, *Lepinatus* spp. and *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais* and *Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans* and *Tipula paludosa*.

From the order of the Lepidoptera, for example, *Achroia grisella, Gaileria mellonella, Plodia interpunctella, Tinea cloacella, Tinea pellionella* and *Tineola bisselliella*.

From the order of the Siphonaptera, for example, *Ctenocephalides canis, Ctenocephalides felis, Pulex irritans, Tunga penetrans* and *Xenopsylla cheopis*.

From the order of the Hymenoptera, for example, *Camponotus herculeanus, Lasius fuliginosus, Lasius niger, Lasius umbratus, Monomorium pharaonis, Paravespula* spp. and *Tetramorium caespitum*.

From the order of the Anoplura, for example, *Pediculus humanus capitis, Pediculus humanus corporis* and *Phthirus pubis*.

From the order of the Heteroptera, for example, *Cimex hemipterus, Cimex lectularius, Rhodinus prolixus* and *Triatoma infestans*.

They are used in the household insecticides sector alone or in combination with other suitable active compounds such as phosphoric esters, carbamates, pyrethroids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The preparation and the use of the compounds according to the invention is shown in the examples below.

PREPARATION EXAMPLES

Example 1

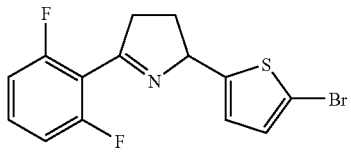

Trifluoroacetic acid (5 ml) is initially charged at 5° C. A solution of tert-butyl-1-(5-bromo-2-thienyl)$_4$-(2,6-difluorophenyl)$_4$-oxobutylcarbamate (II-1) (1.50 g, 3.1 mmol) in dichloromethane (10 ml) is added dropwise. The mixture is allowed to warm to room temperature and stirred at this temperature for another 3 hours. The liquid phase is concentrated under reduced pressure and the residue is taken up in ethyl acetate (50 ml). The organic solution is washed with 1N aqueous sodium hydroxide solution (50 ml), filtered and concentrated.

This gives 0.85 g (75% of theory) of 2-(5-bromo-2-thienyl)-5-(2,6-difluorophenyl)-3,4-dihydro-2H-pyrrole.

HPLC: log P (pH 2.3)=3.45 (93% pure)

NMR (CDCl$_3$): δ=2.05 (1H, m), 2.57 (1H, m), 3.08 (2H, m), 5.50 (1H, m), 6.76 (1H, d), 6.92 (1H, d), 6.97 (2H, m), 73.5 (1H, m) ppm.

The following compounds are obtained analogously to Example 1:

| No. | Compound | log P (pH 2.3) | $^1$H-NMR(δ in ppm) |
|---|---|---|---|
| 2 | | 1.95 | (CDCl$_3$) 1.90(1H, m), 2.55(1H, m), 3.01(2H, m), 5.51(1H, m), 7.02(2H, d), 7.22(2H, m), 7.42(1H, m), 7.56(1H, m) |
| 3 | | 3.34 | (CD$_3$CN) 1.87(1H, m), 2.69(1H, m), 3.08(2H, m), 5.57(1H, m), 6.98(1H, d), 7.08(2H, m), 7.34(1H, d), 7.48(1H, m) |
| 4 | | 2.34 | |
| 5 | | 3.11 | (CDCl$_3$) 2.00(1H, m), 2.63(1H, m), 3.07(2H, m), 5.70(1H, m), 6.94(2H, m), 7.19–7.37(4H, m), 7.76(1H, d), 7.83(1H, d) |

Example 6

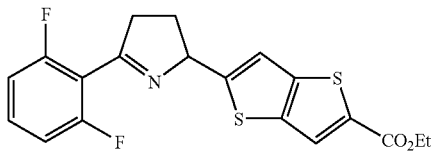

1.1 g (2.16 mmol) of ethyl 5-[1-[(tert-butoxycarbonyl)amino]-4-(2,6-difluorophenyl)-4-oxobutyl]thieno[3,2-b]thiophene-2-carboxylate (II-6) are dissolved in 5 ml of dichloromethane and, at 0° C., are added dropwise to 15 ml of trifluoroacetic acid. The mixture is stirred at 0° C. for another 30 min, and 100 ml of water are then added. The mixture is extracted 3 times with dichloromethane. The combined organic phases are washed twice with water and once with concentrated sodium chloride solution and dried over sodium sulphate. Using cyclohexane/ethyl acetate (2:1), the mixture is then filtered through a 3 g silica gel cartridge and the solvent is removed under reduced pressure. The orange oil is recrystallized from about 20 ml of methyl tert-butyl ketone.

This gives 0.26 g (38% of theory) of ethyl 5-[5-(2,6-difluorophenyl)-3,4-dihydro-2H-pyrrol-2-yl]thieno[3,2-b]thiophene-2-carboxylate in the form of slightly yellowish crystals.

m.p.: 107° C.

Example 7

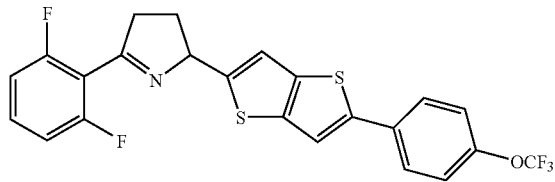

350 mg (0.58 mmol) of tert-butyl 4-(2,6-difluorophenyl)-4-oxo-1-{5-[4-(trifluoromethoxy) thieno[3,2-b]thien-2-yl}butylcarbamate (II-7) are dissolved in 5 ml of dichloromethane and, at 0° C., added dropwise to a solution of 15 ml of dichloromethane and 5 ml of trifluoroacetic acid. The reaction mixture is stirred for 5 min and then stirred into 100 ml of ice-water. The organic phase is separated off, the aqueous phase is extracted once with dichloromethane and the organic phases are combined. The organic phase is once more washed with water, dried over sodium sulphate and concentrated. The crude product is then purified twice by cartridge chromatography (1. cyclohexane/ethyl acetate-2. dichloromethane/cyclohexane gradient).

This gives 0.077 g (28% of theory) of 5-(2,6-difluorophenyl)-2-{5-[4-(trifluoromethoxy)phenyl]thieno[3,2-b]thien-2-yl}-3,4-dihydro-2H-pyrrole in the form of a yellow solid.

m.p.: 135° C.

Starting Materials of the Formula (II)

Example (II-1)

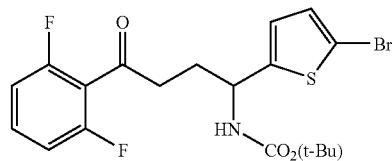

Under an atmosphere of argon, 1,3-difluorobenzene (18.20 g, 0.16 mol) is, at −65° C., initially charged in tetrahydrofuran (100 ml). n-Butyllithium (100 ml, 1.6 M in hexane, 0.16 mol) is added dropwise, and the reaction mixture is stirred at −65° C. for another 30 minutes. A solution of tert-butyl-2-(5-bromo-2-thienyl)-5-oxo-1-pyrrolidinecarboxylate (IX-1) (41.50 g, 0.12 mol) in tetrahydrofuran (250 ml) is added dropwise, and the reaction mixture is then allowed to warm to room temperature over a period of 16 hours. The reaction mixture is stirred into water (500 ml) and extracted with ethyl acetate (2×400 ml). The combined organic phases are dried over sodium sulphate, filtered and concentrated.

This gives 45.80 g (76% of theory) of tert-butyl 1-(5-bromo-2-thienyl)-4-(2,6-difluorophenyl)-4-oxobutylcarbamate.

HPLC: log P (pH 2.3)=4.29 (95% pure)

NMR (CDCl$_3$): δ=1.42 (9H, s), 2.26 (2H, m), 2.99 (2H, m), 4.84 (2H, br), 6.72 (1H, d), 6.90 (1H, d), 6.96 (2H, m), 7.39 (1H, m) ppm.

The following compounds are obtained analogously to Example (II-1):

| No. | Compound | log P (pH 2.3) | $^1$H-NMR(δ in ppm) |
|---|---|---|---|
| II-2 | ![structure] | 4.48 | (CDCl$_3$) 1.42(9H, s), 2.31(2H, m), 2.99(2H, m), 4.86(1H, br), 4.98(1H, br), 6.80–6.95(3H, m), 7.15–7.25(3H, m) |

| No. | Compound | log P (pH 2.3) | $^1$H-NMR($\delta$ in ppm) |
|---|---|---|---|
| II-3 | | 4.28 | (CD$_3$CN) 1.36(9H, s), 2.15(2H, m), 2.96(2H, m), 4.95(1H, m), 5.85(1H, br), 6.90(1H, d), 7.08 (2H, m), 7.35(1H, d), 7.51(1H, m) |
| II-4 | | 4.27 | |
| II-5 | | 4.20 | (CDCl$_3$) 1.41(9H, s), 2.42(2H, m), 3.07(2H, m), 4.80(1H, br), 5.15(1H, br), 6.94(2H, m), 7.39(4H, m), 7.89(2H, m) |

Example (II-6)

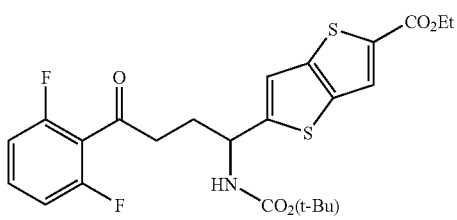

Under argon, 0.35 g (3.06, mmol/1.1 eq.) of 1,3-difluorobenzene is dissolved in 20 ml of tetrahydrofuran. At –65° C., 1.2 ml of butyllithium solution (23% in hexane) are added dropwise. The reaction mixture is stirred at –30° C. for 10 min. A solution of 1.10 g (2.78 mmol) of tert-butyl 2-[5-(ethoxycarbonyl)thieno[3,2-b]thien-2-yl]-5-oxo-1-pyrrolidinecarboxylate (IX-6) in 20 ml of tetrahydrofuran is then added dropwise, and the mixture is stirred at –20° C. for another 30 min. The mixture is warmed to room temperature and, after 30 min, stirred into 120 ml of cold water and extracted with methyl tert-butyl ketone. The organic phase is washed in each case once with water and concentrated sodium chloride solution, dried over sodium sulphate and concentrated. The crude product is filtered through a 3 g silica gel cartridge (mobile phase dichloromethane).

This gives 1.15 g (81% of theory) of ethyl 5-[1-[(tert-butoxycarbonyl)amino]-4-(2,6-difluorophenyl)-4-oxobutyl]thieno[3,2-b]thiophene-2-carboxylate as a brown gel.
m.p.: 104° C.

Example (II-7)

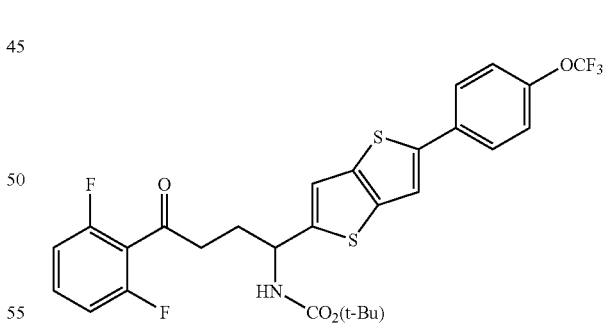

Under argon, 184 mg (1.62 mmol/1.1 eq.) of 1,3-difluorobenzene are dissolved in 20 ml of tetrahydrofuran and, at –65° C., 0.7 ml of butyllithium solution (23% in hexane) is added dropwise. The mixture is stirred at –30° C. for 10 min. A solution of 710 mg (1.47 mmol) of tert-butyl 2-oxo-5-{5-[4-(trifluoromethoxy)phenyl]thieno[3,2-b]thien-2-yl}-1-pyrrolidinecarboxylate (IX-7) in 5 ml of tetrahydrofuran is then added dropwise, and the mixture is stirred at –20° C. for 30 mm. The mixture is warmed to room temperature and, after 30 min under argon, diluted with 60 ml of water and extracted with methyl tert-butyl ketone. The organic phase is washed in each case once with water and concentrated sodium chloride solution, dried over sodium sulphate and concentrated. The crude product is filtered through a 3 g silica gel cartridge using the mobile phase dichloromethane.

This gives 0.24 g (28% of theory) of tert-butyl 4-(2,6-difluorophenyl)₄-oxo-1-{5-[4-(trifluoromethoxy)phenyl]thieno[3,2-b]thien-2-yl}butylcarbamate as a yellow solid.

m.p.: 128–130° C.

Starting Materials of the Formula (IX)

This gives 4.10 g (95% of theory) of tert-butyl 2-(5-bromo-2-thienyl)-5-oxo-1-pyrrolidinecarboxylate.

HPLC: log P (pH 2.3)=3.03 (96% pure)

m.p.: 93° C.

NMR (CDCl₃): δ=1.43 (9H, s), 2.03–2.09 (1H, m), 2.43–2.58 (2H, m), 2.75 (1H, m) 5.37 (1H, m), 6.72 (1H, d), 6.92 (1H, d) ppm.

The following compounds are obtained analogously to Example (IX-1):

| No. | Compound | m.p. | log P | ¹H-NMR(δ in ppm) |
|---|---|---|---|---|
| IX-2 | | | 2.39 (pH 2.3) | (CDCl₃) 1.39(9H, s), 2.05–2.12(1H, m), 2.48–2.58(2H, m), 2.77(1H, m) 5.47(1H, m), 6.95(2H, m), 7.23(1H, m) |
| IX-3 | | | 2.77 (pH 7.5) | (CDCl₃) 1.36(9H, s), 2.00(1H, m), 2.47–2.60(2H, m), 2.70–2.80(1H, m) 5.55(1H, m), 6.91(1H, d), 7.21(1H, d) |
| IX-4 | | | 2.65 (pH 2.3) | (CDCl₃) 1.36(9H, s), 1.98(1H, m), 2.48–2.59(2H, m), 2.77(1H, m) 5.55(1H, m), 6.91(1H, d), 7.21(1H, d) |
| IX-5 | | 171° C. | 3.03 (pH 2.3) | (CD₃CN) 1.20(9H, s), 1.93(1H, m), 2.45–2.63(3H, m), 5.60(1H, m), 7.30(1H, s) 7.42(2H, m), 7.82(1H, d), 7.95(1H, d) |

Example (IX-1)

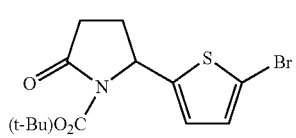

Example (IX-6)

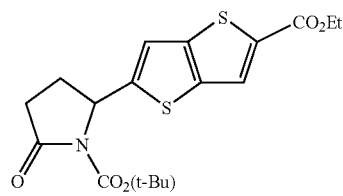

At 0° C., 5-(5-bromo-2-thienyl)-2-pyrrolidinone (XI-1) (3.26 g, 94% pure, ≈0.012 mol) is initially charged in dichloromethane (65 ml). Di-tert-butyl dicarbonate (3.00 g, 0.014 mol) and 4-dimethylaminopyridine (92 mg, 0.75 mmol) are added successively. The mixture is stirred at room temperature for 24 hours, after which more di-tert-butyl dicarbonate (0.65 g, 3.0 mmol) and 4-dimethylaminopyridine (10 mg, 0.08 mmol) is added. The mixture is stirred for another 4 hours. The organic solution is washed successively with 1N hydrochloric acid, saturated aqueous sodium bicarbonate solution, water and sodium chloride solution, dried over sodium sulphate, filtered and concentrated.

Under argon, 2.00 g (6.77 mmol) of ethyl 5-(5-oxo-2-pyrrolidinyl)thieno[3,2-b]thiophene-2-carboxylate (XI-6) are dissolved in 40 ml of dichloromethane and, at 0° C., 3.00 g (13.7 mmol/2 eq.) of di-tert-butyl dicarbonate, 0.84 g (6.9 mmol/1.02 eq.) of 4-dimethylaminopyridine and 9.0 ml of triethylamine are added successively. The mixture is stirred at 0° C. for 60 min. The mixture is diluted with 60 ml of dichloromethane, washed twice with in each case 100 ml of aqueous hydrochloric acid (0.25 N), once with water and once with concentrated sodium chloride solution, dried over sodium sulphate and concentrated. At about 40° C., the crude product is then stirred in 10 ml of methyl tert-butyl ketone, filtered off with suction and dried.

This gives 2.3 g (86% of theory) of tert-butyl 2-[5-(ethoxycarbonyl)thieno[3,2-b]thien-2-yl]-5-oxo-1-pyrrolidinecarboxylate as a light-brown solid.

m.p.: 178° C.

Example (IX-7)

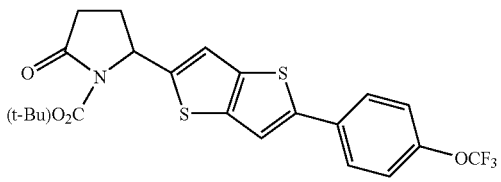

Under argon, 6.6 g (8.94 mmol, 52% pure) of 5-{5-[4-(trifluoromethoxy)phenyl]thieno[3,2-b]thien-2-yl}-2-pyrrolidinone (XI-7) are dissolved in 120 ml of dichloromethane, and 7.5 g (34.2 mmol/2, eq.) of di-tert-butyl dicarbonate, 2.2 g (17.5 mmol/1.02 eq.) of 4-dimethylaminopyridine and 23 ml of triethylamine are added successively at 0° C. The mixture is stirred at 0° C. for another 2 hours. The mixture is diluted with 60 ml of dichloromethane, washed twice with in each case 50 ml of aqueous hydrochloric acid (0.25 N), once with water and once with concentrated sodium chloride solution and then dried over sodium sulphate. The resulting solution is filtered through silica gel using dichloromethane and the solvent is then removed.

This gives 4.1 g (95% of theory) of tert-butyl 2-oxo-5-{5-[4-(trifluoromethoxy)phenyl]thieno[3,2-b]thien-2-yl)-1-pyrrolidinecarboxylate in the form of a grey solid.

m.p.: 164° C.

Starting Materials of the Formula (XI)

Example (XI-1)

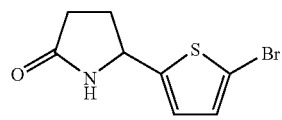

A mixture of glacial acetic acid (15 ml) and concentrated sulphuric acid (5 ml) is initially charged and cooled to 0° C. 5-Ethoxy-pyrrolidin-2-one (3.04 g, 85% pure, 0.02 mol) and 2-bromothiophene (13.12 g, 0.08 mol) are added successively. The reaction mixture is allowed to slowly warm to room temperature and then stirred at this temperature for 60 hours. The mixture is poured into ice-water and extracted with ethyl acetate. The organic phase is washed successively with saturated aqueous sodium bicarbonate solution, water and sodium chloride solution, dried over sodium sulphate, filtered and concentrated.

This gives 3.94 g (75% of theory) of 5-(5-bromo-2-thienyl)-2-pyrrolidinone.

HPLC: log P (pH 2.3)=1.62 (94% pure)

m.p.: 104° C.

NMR (CDCl$_3$): δ=2.10 (1H, m), 2.34–2.66 (3H, m), 4.94 (1H, m), 6.01 (1H, br), 6.75 (1H, d), 6.91 (1H, d) ppm.

The following compounds are obtained analogously to Example (IX-1):

| No. | Compound | m.p. (° C.) | log P (pH 2.3) | $^1$H-NMR(δ in ppm) |
|---|---|---|---|---|
| XI-2 | | 111 | 1.03 | (CDCl$_3$) 2.14(1H, m), 2.36–2.63(3H, m), 5.04(1H, m), 6.15(1H, br), 6.98(2H, m), 7.26(1H, m) |
| XI-3 | | 122 | 1.41 | (CDCl$_3$) 2.14(1H, m), 2.38–2.73(3H, m), 5.16(1H, m), 6.00(1H, br), 6.91(1H, d), 7.25(1H, d) |
| XI-4 | | 104 | 1.33 | (CDCl$_3$) 2.12(1H, m), 2.44–2.60(3H, m), 5.10(1H, m), 6.15(1H, br), 6.81(1H, d), 7.25(1H, d) |
| XI-5 | | 115 | 1.73 | (CD$_3$CN) 2.03(1H, m), 2.33(2H, m), 2.66(1H, m), 5.14(1H, m), 6.45(1H, br), 7.42(3H, m), 7.83(1H, d), 7.94(1H, d) |

Example (XI-6)

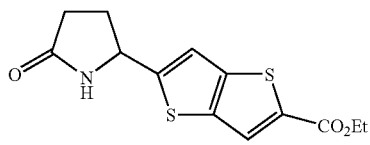

1.2 g (9.42 mmol) of 5-ethoxy-2-pyrrolidinone are initially charged in 15 ml of glacial acetic acid and 5 ml of concentrated sulphuric acid. At a temperature below 10° C., 1.0 g (4.71 mmol) of ethyl thieno[3,2-b]thiophene-2-carboxylate is added, and the mixture is stirred at room temperature for another 40 h. The mixture is stirred into 150 ml of cold water and extracted three times with in each case 25 ml of dichloromethane. The combined organic phases are washed twice with water and once with concentrated sodium chloride solution, dried and concentrated. The yellow crude product is stirred in about 20 ml of methyl tert-butyl ketone. The residue is filtered off with suction and dried.

This gives 1.0 g (72% of theory) of ethyl 5-(5-oxo-2-pyrrolidinyl)thieno[3,2-b]thiophene-2-carboxylate in the form of cream-coloured crystals.

m.p.: 140° C.

Example (XI-7)

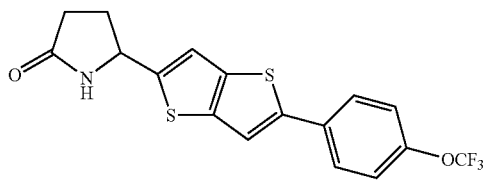

5.3 g (40.6 mmol) of 5-ethoxy-2-pyrrolidinone are initially charged in 80 ml of glacial acetic acid and 27 ml of concentrated sulphuric acid. At a temperature below 10° C., 6.1 g (20.3 mmol) of 2-[4-(trifluoromethoxy)-phenyl]thieno[3,2-b]thiophene (XIII-1) are added, and the mixture is stirred at room temperature for another 16 hours. The mixture is stirred into 300 ml of cold water and extracted three times with in each case 60 ml of dichloromethane. The organic phases are combined, washed twice with water and once with concentrated sodium chloride solution, dried over sodium sulphate and concentrated. The crude product is then stirred in 60 ml of methyl tert-butyl ketone at about 40° C., cooled, filtered off with suction and dried.

This gives 6.8 g (87% of theory) of 5-{5-[4-(trifluoromethoxy)phenyl]thieno[3,2-b]thien-2-yl}-2-pyrrolidinone as a light-grey solid.

m.p.: 220° C. (decomposition)

Starting Materials of the Formula (XIII)

Example (XIII-1)

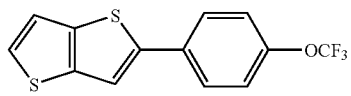

Under argon, 29.0 g (25.5 mmol) of 2-bromothien[3,2-b]thiophene-are dissolved in 150 ml of tetrahydrofuran, 10.0 g (48.5 mmol) of 4-trifluoromethoxyphenylboronic acid and 0.8 g (0.7 mmol) of tetrakis(triphenylphosphine)-palladium (0) are added at room temperature and the mixture is heated at reflux for 1 hour. Another 2.0 g of 4-trifluoromethoxyphenylboronic acid and 0.2 g tetrakis(triphenylphosphine)-palladium(0) are then added, and the mixture is stirred at reflux for another 16 hours.

At this temperature, a total of 100 ml of a 20% strength aqueous sodium carbonate solution are then added dropwise, and the mixture is heated at reflux for 1 hour. The reaction mixture is diluted with 400 ml of water and extracted three times with in each case 100 ml of methyl tert-butyl ketone. The organic phases are combined, washed in each case once with water and concentrated sodium chloride solution, dried over sodium sulphate and concentrated. The crude product is absorbed on about 25 g of silica gel and purified by flash chromatography using the mobile phase n-hexane.

This gives 6.2 g (81% of theory) of 2-[4-(trifluoromethoxy)phenyl]thieno[3,2-b]thiophene in the form of a white solid.

m.p.: 162° C.

Example 8

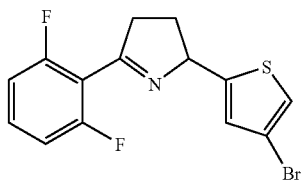

4-Azido-4-(4-bromo-2-thienyl)-1-(2,6-difluorophenyl)-1-butanone (III-1) (1.63 g, 42% pure, ≈1.79 mmol) is initially charged in n-pentane (100 ml). At room temperature, triphenylphosphine (0.65 g, 2.50 mmol) is added a little at a time. The mixture is stirred at room temperature for another 16 hours. Florisil (5 g) is added, and the mixture is concentrated to dryness. The crude product is purified by silica gel chromatography (mobile phase: cyclohexane/ethyl acetate 9:1→7:3).

This gives 0.15 g (37% of theory) of 2-(4-bromo-2-thienyl)-5-(2,6-difluorophenyl)-3,4-dihydro-2H-pyrrole.

HPLC: log P (pH 2.3)=3.41 (100% pure)

NMR (CD₃CN): δ=1.95 (1H, m), 2.60 (1H, m), 3.05–3.08 (2H, m), 5.47 (1H, m), 6.96 (1H, s), 7.07 (2H, m), 7.27 (1H, s), 7.44–7.47 (1H, m) ppm.

A further batch (0.15 g, 78% pure) was also isolated.

Example 9

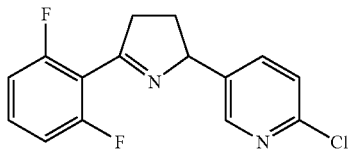

4-Azido-4-(6-chloro-3-pyridinyl)-1-(2,6-difluorophenyl)-1-butanone (III-2) (1.20 g, 54.4% pure, 1.94 mmol) is initially charged in n-hexane (100 ml). At room temperature, triphenylphosphine (0.94 g, 3.56 mmol) is added a little at a time. The mixture is stirred at room temperature for another 16 hours. Florisil (7 g) is added, and the reaction mixture is then evaporated to dryness. The crude product is purified by silica gel chromatography (mobile phase: cyclohexane/ethyl acetate 9:1→7:3).

This gives 0.47 g (83% of theory) of 2-(6-chloro-3-pyridinyl)-5-(2,6-difluorophenyl)-3,4-dihydro-2H-pyrrole.

HPLC: log P (pH 2.3)=1.93 (100% pure)

NMR (CD₃CN): δ=1.77–1.84 (1H, m), 2.60–2.66 (1H, m), 3.05–3.09 (2H, m), 5.32 (1H, m), 7.07 (2H, m), 7.38 (1H, d), 7.47 (1H, m), 7.69 (1H, dd), 8.37 (1H, d) ppm.

Example 10

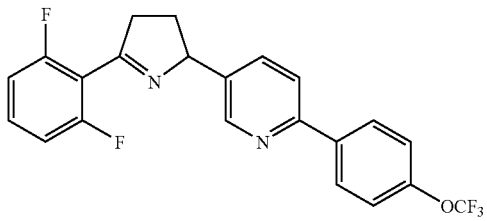

4-Azido-1-(2,6-difluorophenyl)-4-{6-[4-(trifluoromethoxy)phenyl]-3-pyridinyl}-1-butanone (1-3) (0.80 g, 1.73 mmol) is initially charged in n-hexane (100 ml).

Triphenylphosphine (0.45 g, 1.73 mmol) is added. The mixture is stirred at room temperature for another 16 hours. Florisil (5 g) is added, and the reaction mixture is concentrated. The crude product is purified by silica gel chromatography (mobile phase: hexane/ethyl acetate 9:1→4:1).

This gives 0.42 g (50% of theory) of 5-[5-(2,6-difluorophenyl)-3,4-dihydro-2H-pyrrol-2-yl]-2-[4-(trifluoromethoxy)phenyl]pyridine.

HPLC: log P (pH 2.3)=3.50 (86% pure)

Starting Materials of the Formula (III)

Example (III-1)

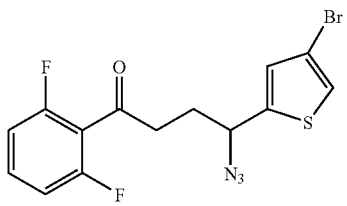

4-(4-Bromo-2-thienyl)-4-chloro-1-(2,6-difluorophenyl)-1-butanone (XV-1) (0.95 g, 84.65% pure, ≈2.1 mmol) is initially charged in acetone (4 ml). A solution of sodium azide (0.25 g, 3.75 mmol) in water (10 ml) and methyl-tri-n-octylammonium chloride (0.30 g, 0.74 mmol) are added successively. The mixture is stirred at 50° C. for another 16 hours. Water (30 ml) is added, and the reaction mixture is extracted with ethyl acetate (2×50 ml). The combined organic phases are dried over sodium sulphate, filtered and concentrated. The crude product is reacted further without any purification.

This gives 1.63 g (85% of theory) of 4-azido-4-(4-bromo-2-thienyl)-1-(2,6-difluorophenyl)-1-butanone.

HPLC: log P (pH 2.3)=3.00 (42% pure)

$\tilde{v}_{azide}$: 2090 cm⁻¹

Example (III-2)

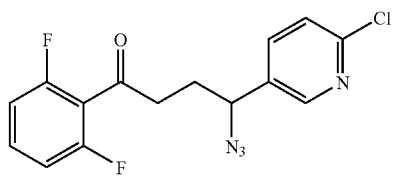

4-(6-Chloro-3-pyridinyl)-4-chloro-1-(2,6-difluorophenyl)-1-butanone (XV-2) (1.30 g, 57.6% pure, 2.27 mmol) is initially charged in acetone (7.5 ml). A solution of sodium azide (0.38 g, 5.90 mmol) in water (15 ml) and methyl tri-n-octylammonium chloride (0.30 g, 0.74 mmol) are added successively. The mixture is stirred at 50° C. for another 16 hours. Water (30 ml) is added, and the reaction mixture is extracted with ethyl acetate (2×50 ml). The combined organic phases are dried over sodium sulphate, filtered and concentrated. The crude product is reacted further without any purification.

This gives 1.20 g (85% of theory) of 4-azido-4-(6-chloro-3-pyridinyl)-1-(2,6-difluorophenyl)-1-butanone.

HPLC: log P (pH 2.3)=3.33 (54% pure)

$\tilde{v}_{azide}$: 2080 cm⁻¹

Example (III-3)

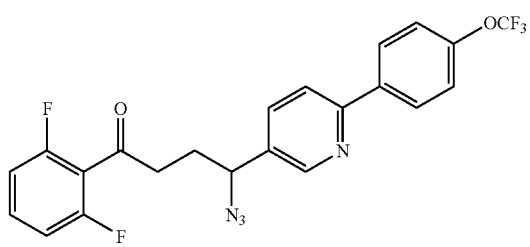

4-Chloro-1-(2,6-difluorophenyl)-4-{6-[4-(trifluoromethoxy)phenyl]-3-pyridinyl}-1-butanone (XV-3) (0.81g, 1.78 mmol) is initially charged in acetone (5 ml). A solution of sodium azide (0.17 g, 2.67 mmol) in water (10 ml) and methyl-tri-n-octylammonium chloride are added successively. The mixture is stirred at 50° C. for another 16 hours. Water is added, and the reaction mixture is extracted twice with ethyl acetate. The combined organic phases are dried over sodium sulphate, filtered and concentrated.

This gives 0.80 g (61% of theory) of 4-azido-1-(2,6-difluorophenyl)-4-{6-[4-(trifluoromethoxy)phenyl]-3-pyridinyl}-1-butanone.

HPLC: log P (pH 2.3)=4.78 (63% pure)

Starting Materials of the Formula (XV).

Example (XV-1)

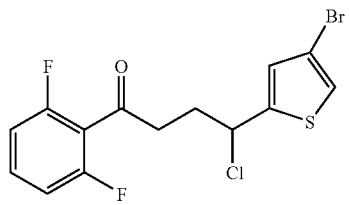

At room temperature, [2-(4-bromo-2-thienyl)cyclopropyl](2,6-difluorophenyl)methanone (XVII-1) (1.40 g, 82% pure, ≈3.4-mmol) is stirred with concentrated hydrochloric acid (10 ml) for 72 hours. Dichloromethane is added, and the organic phase is washed with water, dried over sodium sulphate, filtered and concentrated. The crude product is reacted further without any purification.

This gives 1.27 g (83% of theory) of 4-(4-bromo-2-thienyl)$_4$-chloro-1-(2,6-difluorophenyl)-1-butanone.

HPLC: log P (pH 2.3)=3.00 (85% pure)

NMR (CD$_3$CN): δ=2.48 (2H, m), 3.08 (2H, m), 5.36 (1H, m), 7.00–7.12 (3H, m 7.40 (1H, s), 7.47–7.57 (1H, m) ppm.

Example (XV-2)

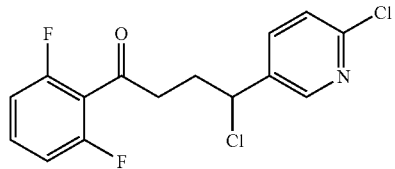

At room temperature, [2-(6-chloro-3-pyridinyl)cyclopropyl](2,6-difluorophenyl)methanone (XVII-2) (2.20 g, 7.50 mmol) is stirred with concentrated hydrochloric acid (22 ml) for 60 hours. The reaction mixture is concentrated under reduced pressure. The crude product is reacted further without any purification.

This gives 2.10 g (49% of theory) of 4-(6-chloro-3-pyridinyl)-4-chloro-1-(2,6-difluorophenyl)-1-butanone.

HPLC: log P (pH 2.3)=3.37 (58% pure)

Example (XV-3)

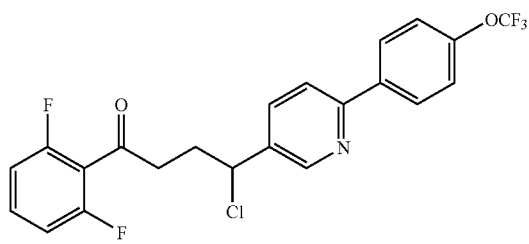

At room temperature, (2,6-difluorophenyl)(2-{6-[4-(trifluoromethoxy)phenyl]-3-pyridinyl}cyclopropyl)methanone (XVII-3) (0.75 g, 1.79 mmol) is stirred with concentrated hydrochloric acid (8.00 ml) for 60 hours. The reaction mixture is concentrated under reduced pressure.

This gives 0.81 g (85% of theory) of 4-chloro-1-(2,6-difluorophenyl)$_4$-{6-[4-(trifluoromethoxy)phenyl]-3-pyridinyl}-1-butanone.

HPLC: log P (pH 2.3)=4.88 (86% pure)

Starting Materials of the Formula (XVII)

Example (XVII-1)

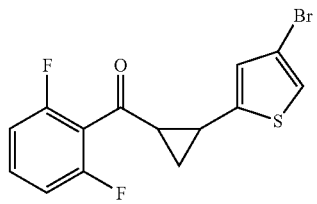

Sodium hydride (0.40 g, 0.01 mol, 60% suspension in paraffin oil) is suspended in DMSO (15 ml). At room temperature, trimethylsulphoxonium iodide (2.20 g, 0.01 mol) is added a little at a time. The reaction mixture is then stirred at room temperature for 0.5 hours. At room temperature, a solution of 3-(4-bromo-2-thienyl)-1-(2,6-difluorophenyl)-2-propen-1-one (XVII-1) (2.30 g, 7.0 mmol) in dimethyl sulphoxide (15 ml) is slowly added dropwise, and the mixture is then stirred at room temperature for another 16-hours. The mixture is poured into ice-water and extracted twice with ethyl acetate. The combined organic phases are dried over sodium sulphate, filtered and concentrated. The crude product is reacted further without any purification.

This gives 1.86 g (63% of theory) of [2-(4-bromo-2-thienyl)cyclopropyl](2,6-difluorophenyl)methanone.

HPLC: log P (pH 2.3)=4.14 (82.0% pure)

NMR (CD$_3$CN): δ=1.59 (1H, m), 1.87 (1H, m), 2.73 (1H, m), 2.84 (1H, m), 6.88 (1H, s), 7.08 (2H, m), 7.19 (1H, s), 7.54 (1H, m) ppm.

Example (XVII-2)

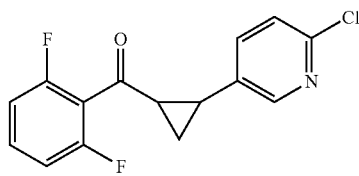

Sodium hydride (3.19 g, 79.84 mmol, 60% suspension in paraffin oil) is suspended in dimethyl sulphoxide (100 ml). At a temperature at or below 32° C., trimethylsulphoxonium iodide (17.57 g, 79.84 mmol) is added a little at a time. The reaction mixture is then stirred at room temperature for another 1.5 hours. A solution of 3-(6-chloro-3-pyridinyl)-1-(2,6-difluorophenyl)-2-propen-1-one (XVIII-2) (20.30 g, 72.59 mmol) in DMSO (120 ml) is slowly added dropwise at a temperature of 36° C. or below. The mixture is then stirred at room temperature for another 16 hours. The reaction mixture is poured into ice-water and the precipitate is filtered off with suction.

This gives 22.70 g (97% of theory) of [2-(6-chloro-3-pyridinyl)cyclopropyl](2,6-difluorophenyl)methanone.

HPLC: log P (pH 2.3)=2.92 (91% pure)

NMR (CD₃CN): δ=1.63 (1H, m), 1.91 (1H, m), 2.73 (2H, m), 7.07 (2H, m), 7.32 (2H, d), 7.50–7.55 (3H, m), 8.28 (1H, d) ppm.

Example (XVII-3)

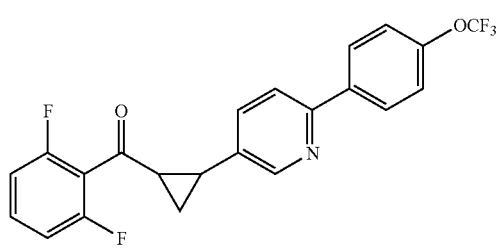

4,4,5,5-Tetramethyl-2-[4-(trifluoromethoxy)phenyl]-1,3,2-dioxaborolane (1.73 g, 6.00 mmol), bis(diphenylmethylphosphine)palladium(II) chloride (0.11 g, 0.15 mmol) and sodium carbonate solution (7.50 ml, 2 M) are added successively to a solution of [2-(6-chloro-3-pyridinyl)cyclopropyl](2,6-difluorophenyl)methanone (XVII-2) (1.47 g, 5.00 mmol) in 20 ml of dimethoxyethane, and the reaction mixture is then allowed to react at 80° C. for 16 hours. For work-up, water is added to the reaction mixture and the resulting precipitate is filtered off with suction. The precipitate is taken up in dichloromethane, 10 g of Florisil are added and the mixture is then purified by silica gel chromatography (mobile phase: hexane/ethyl acetate 9:1, v/v).

This gives 1.09 g (51% of theory) of (2,6-difluorophenyl)(2-{6-[4-(trifluoromethoxy)phenyl]-3-pyridinyl}cyclopropyl)methanone.

HPLC: log P (pH 2.3)=4.40 (98% pure)

Starting Materials of the Formula (XVIII)

Example (XVIII-1)

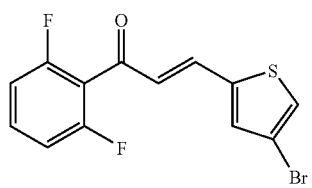

2,6-Difluoroacetophenone (1.56 g, 0.01 mol) and 4-bromothiophene-2-carboxaldehyde (1.91 g, 0.01 mol) are initially charged in methanol (70 ml) and, water (16 ml). At room temperature, aqueous sodium hydroxide solution (3 ml, 10% w/v) is added dropwise, and the mixture is then stirred at room temperature for another 16 hours. After cooling to 0° C., the precipitate is filtered off with suction and washed with an ice-cold methanol/water (3:1) mixture.

This gives 2.49 g (76% of theory) of 3-(4-bromo-2-thienyl)-1-(2,6-difluorophenyl)-2-propen-1-one.

HPLC: log P (pH 2.3)=3.78 (100% pure)

NMR (CD₃CN): δ=6.89 (1H, d), 7.11 (2H, m), 7.40 (1H, s), 7.54–7.59 (3H, m) ppm.

Example (XVIII-2)

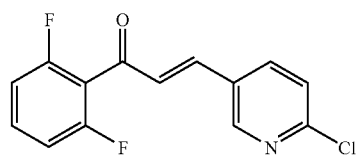

2,6-Difluoroacetophenone (15.60 g, 0.10 mol) and 2-chloropyridine-5-carboxaldehyde (14.20 g, 0.10 mol) are initially charged in methanol (300 ml) and water (100 ml). At 5–8° C., aqueous sodium hydroxide solution (30 ml, 10% w/v) is slowly added dropwise. The reaction mixture is then stirred at 8° C. for one hour. The precipitate is filtered off with suction.

This gives 20.30 g (73% of theory) of 3-(6-chloro-3-pyridinyl)-1-(2,6-difluorophenyl)-2-propen-1-one.

HPLC: log P (pH 2.3)=2.87 (98.54% pure)

NMR (CD₃CN): δ=7.09–7.20 (3H, m), 7.45–7.61 (3H, m), 8.04 (1H, dd), 8.58 (1H, d) ppm.

Example 11

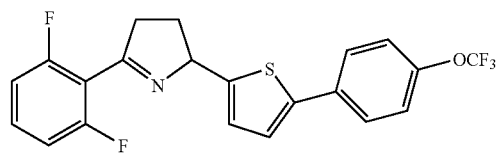

Under an atmosphere of argon, 2-(5-bromo-2-thienyl)-(2,6-difluorophenyl)-3,4-dihydro-2H-pyrrole (Ex. 1) (0.65 g, 1.90 mmol) and 4-trifluoromethoxyphenylboronic acid (0.50 g, 2.4 mmol) are initially charged in acetone (10 ml). A solution of potassium carbonate (0.70 g, 5.07 mmol) in water (10 ml) and a solution of palladium acetate (13 mg, 0.058 mmol) in acetone (2 ml) are added successively. The mixture is stirred at 60° C. for 4 hours, more 4-trifluoromethoxyphenylboronic acid (0.25 g, 1.2 mmol), of the solution of potassium carbonate (0.35 g, 2.37 mmol) in water (5 ml) and of the solution of palladium acetate (6 mg, 0.027 mmol) in acetone (1 ml) are added, and the mixture is stirred at 60° C. for another 6 hours. After cooling to room temperature, the mixture is filtered and concentrated. The filtrate is diluted with ethyl acetate and water and the phases are separated. The organic phase is dried over sodium sulphate, filtered and concentrated. The crude product is purified by silica gel chromatography (mobile phase: cyclohexane/ethyl acetate 4:1).

This gives 0.40 g (47% of theory) of 5-(2,6-difluorophenyl)-2-{5-[4-(trifluoromethoxy)phenyl]-2-thienyl}-3,4-dihydro-2H-pyrrole.

HPLC: log P (pH 2.3)=5.16(95% pure)

NMR (CD$_3$CN): δ=2.12 (1H, m), 2.62 (1H, m), 3.08 (1H, m), 3.14 (1H, m), 5.58 (1H, m), 6.97 (3H, m), 7.15 (1H, s), 7.20 (2H, d), 7.34 (1H, m), 7.58 (2H, d) ppm.

Example 12

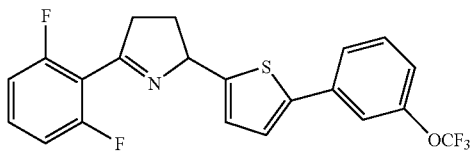

Under an atmosphere of argon, 2-(5-bromo-2-thienyl)-(2,6-difluorophenyl)-3,4-dihydro-2H-pyrrole (Ex. 1) (0.65 g, 1.90 mmol) and 3-trifluoromethoxyphenylboronic acid (0.50 g, 2.4 mmol) are initially charged in acetone (10 ml). A solution of potassium carbonate (0.70 g, 5.07 mmol) in water (10 ml) and a solution of palladium acetate (26 mg, 0.12 mmol) in acetone (3 ml) are added successively. The reaction mixture is stirred at 60° C. for 16 hours. After cooling to room temperature, the mixture is diluted with ethyl acetate and water and the phases are separated. The organic phase is dried over sodium sulphate, filtered and concentrated. The crude product is purified by silica gel chromatography (mobile phase: cyclohexane/ethyl acetate 9:1).

This gives 0.45 g (53% of theory) of 5-(2,6-difluorophenyl)-2-{5-[3-(trifluoromethoxy)phenyl]-2-thienyl}-3,4-dihydro-2H-pyrrole.

HPLC: log P (pH 2.3)=4.84 (94% pure)

NMR (CD$_3$CN): δ=2.15 (1H, m), 2.65 (1H, m), 3.13 (2H, m), 5.61 (1H, m), 6.99 (3H, m), 7.11 (1H, m), 7.22 (1H, d), 7.33–7.49 (3H, m), 7.51 (1H, m) ppm.

Example 13

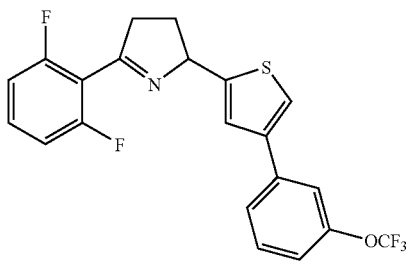

Under an atmosphere of argon, 2-(4-bromo-2-thienyl)-5-(2,6-difluorophenyl)-3,4-dihydro-2H-pyrrole (Ex. 8) (0.56 g, 1.70 mmol) and 3-trifluoromethoxyphenylboronic acid (0.50 g, 2.4 mmol) are initially charged in acetone (10 ml). A solution of potassium carbonate (0.70 g, 5.07 mmol) in water (10 ml) and a solution of palladium acetate (24 mg, 0.11 mmol) in acetone (3 ml) are added successively. The reaction mixture is stirred at 60° C. for 16 hours. After cooling to room temperature, the mixture is diluted with ethyl acetate and water and the phases are separated. The organic phase is dried over sodium sulphate, filtered and concentrated. The crude product is purified by silica gel chromatography (mobile phase: toluene/ethyl acetate 1:0 e 9:1).

This gives 0.41 g (53% of theory) of 5-(2,6-difluorophenyl)-2-{4-[3-(trifluoromethoxy)phenyl]-2-thienyl}-3,4-dihydro-2H-pyrrole.

HPLC: log P (pH 2.3)=4.08 (93.6% pure)

NMR (CD$_3$CN): δ=2.05 (1H, m), 2.64 (1H, m), 3.07 (2H, m), 5.54 (1H, m), 7.07 (2H, m), 7.23 (1H, d), 7.39 (1H, s), 7.51 (2H, m), 7.58 (2H, m), 7.67 (1H, d) ppm.

Example 14

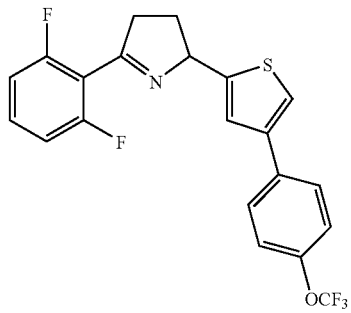

Under an atmosphere of argon, 2-(4-bromo-2-thienyl)-5-(2,6-difluorophenyl)-3,4-dihydro-2H-pyrrole (Ex. 8) (0.75 g, 2.30 mmol) and 4-trifluoromethoxyphenylboronic acid (0.71 g, 3.45 mmol) are initially charged in acetone (10 ml). A solution of potassium carbonate (0.75 g, 5.43 mmol) in water (10 ml) and a solution of palladium acetate (25 mg, 0.11 mmol) in acetone (3 ml) are added successively. The reaction mixture is stirred at 60° C. for 16 hours. After cooling to room temperature, the mixture is diluted with ethyl acetate and water and the phases are separated. The organic phase is dried over sodium sulphate, filtered and concentrated. The crude product is purified by silica gel chromatography (mobile phase: n-hexane/ethyl acetate 9:1).

This gives 0.15 g (15% of theory) of 5-(2,6-difluorophenyl)-2-{4-[4-(trifluoromethoxy)phenyl]-2-thienyl}-3,4-dihydro-2H-pyrrole.

HPLC: log P (pH 2.3)=4.66 (96.3% pure)

NMR (CD$_3$CN): δ=2.05 (1H, m), 2.65 (1H, m), 3.07 (2H, m), 5.54 (1H, m), 7.08 (2H, m), 7.33 (2H, d), 7.37 (1H, s), 7.47 (1H, m), 7.49 (1H, s), 7.73 (2H, d) ppm.

The stated logP values were determined in accordance with EEC Directive 79/831 Annex V.A8 by HPLC (High Performance Liquid Chromatography), using a reversed-phase column (C 18). Temperature: 43° C.

In the acidic range, the determination was carried out at pH 2.3 using the mobile phases 0.1% aqueous phosphoric acid and acetonitrile; linear gradient from 10% acetonitrile to 90% acetonitrile.

In the neutral range, the determination was carried out at pH 7.5 using the mobile phases 0.01 molar aqueous phosphate buffer solution and acetonitrile; linear gradient from 10% acetonitrile to 90% acetonitrile.

Calibration was carried out using unbranched alkan-2-ones (having 3 to 16 carbon atoms) with known logP values (determination of the logP values by the retention times using linear interpolation between two successive alkanones).

The lambda-max values were determined in the maxima of the chromatographic signals using the UV spectra from 200 nm to 400 nm.

USE EXAMPLES

Example A

*Meloidogyne* Test
Solvent: 30 parts by weight of dimethylformamide
Emulsifier: 1 part by weight of alkylaryl polyglycol ether To produce a suitable preparation of active compound, 1 part by weight of active compound is mixed with the stated amount of solvent and emulsifier, and the concentrated is diluted with water to the desired concentration.

Vessels are filled with sand, solution of active compound, *Meloidogyne incognita* egg/larvae suspension and lettuce seeds. The lettuce seeds germinate and the plants develop. On the roots galls are formed.

After the desired period of time, the nematicidal action is determined in % by the formation of galls. 100% means that no galls have been found; 0% means that the number of galls on the treated plants corresponds to that of the untreated control.

Active compounds and test results are shown in the Table below.

Example B

*Myzus* Test

Solvent: 7 parts by weight of dimethylformamide

Emulsifier: 1 part by weight of alkylaryl polyglycol ether

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by the peach aphid (*Myzus persicae*) are treated by being dipped into the preparation of active compound of the desired concentration.

After the desired period of time, the kill in % is determined. 100% means that all aphids have been killed; 0% means that none of the aphids have been killed.

Active compounds and test results are shown in the Table below.

TABLE A plant-damaging nematodes
Meloidogyne Test

| Active compounds | Concentration of active compound in ppm | Kill rate in % after 14 d |
|---|---|---|
| (structure shown) | 20 | 98 |

TABLE B plant-damaging insects
Myzus Test

| Active compounds | Concentration of active compound in ppm | Kill rate in % after 6$^d$ |
|---|---|---|
| 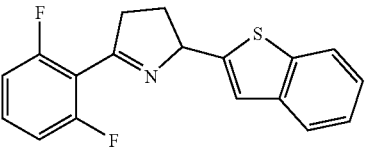 | 1000 | 95 |

Example C

*Phaedon Larvae Test*

Solvent: 30 parts by weight of dimethylformamide
Emulsifier: 1 part by weight of alkylaryl polyglycol ether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

Active compounds and test results are shown in the Table below.

TABLE C plant-damaging insects
Phaedon Larvae Test

| Active compounds | Concentration of active compound in ppm | Kill rate in % after 7$^d$ |
|---|---|---|
| 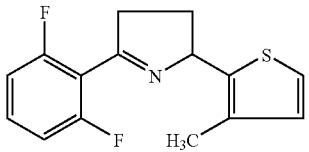 | 1000 | 100 |
| 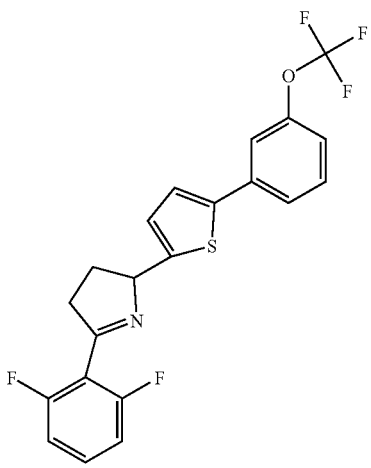 | 1000 | 100 |

TABLE C-continued

| | plant-damaging insects Phaedon Larvae Test | |
|---|---|---|
| Active compounds | Concentration of active compound in ppm | Kill rate in % after $7^d$ |
| 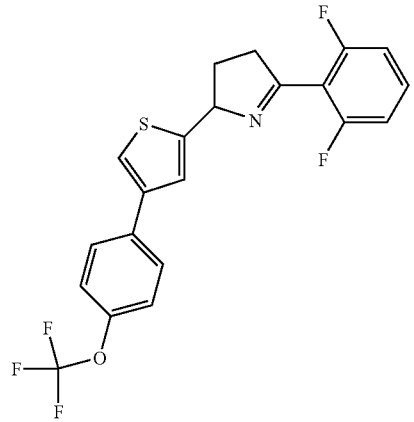 | 1000 | 100 |

Example D

*Plutella* Test
Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamond back moth (*Plutella xylostella*) while the leaves are still moist.

After the desired period of time, the kill in % is determined. 100% means that all caterpillars have been killed; 0% means that none of the caterpillars have been killed.

Active compounds and test results are shown in the Table below.

TABLE D

| | plant-damaging insects Plutella test | |
|---|---|---|
| Active compounds | Concentration of active compound in ppm | Kill rate in % after $6^d$ |
| 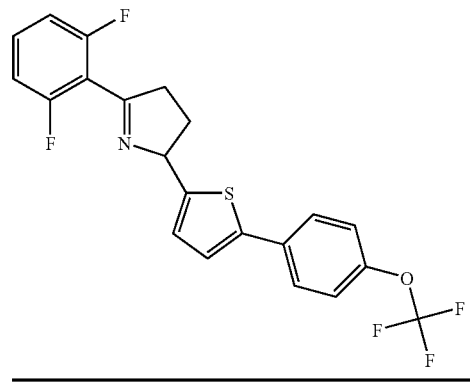 | 8 | 90 |

Example E

*Spodoptera frugiperda* Test
Solvent: 30 parts by weight of dimethylformamide.
Emulsifier: 1 part by weight of alkylaryl polyglycol ether To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the army worm (*Spodoptera frugiperda*) while the leaves are still moist.

After the desired period of time, the kill in % is determined. 100% means that all caterpillars have been killed; 0% means that none of the caterpillars have been killed.

Active compounds and test results are shown in the Table below.

TABLE E plant-damaging insects
*Spodoptera frugiperda* Test

| Active compounds | Concentration of active compound in ppm | Kill rate in % after $7^d$ |
|---|---|---|
| 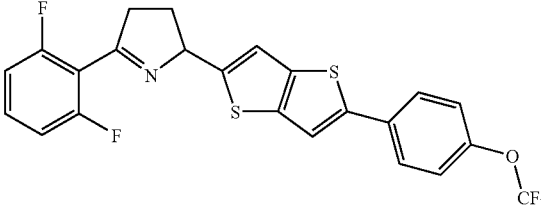 | 500 | 100 |
| 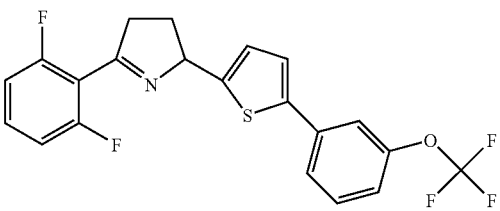 | 1000 | 100 |
| 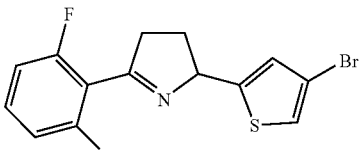 | 1000 | 100 |
| 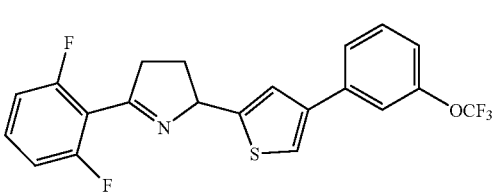 | 1000 | 100 |
| 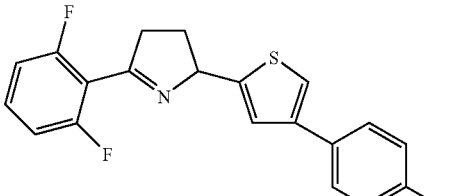 | 1000 | 100 |
|  | 500 | 100 |

Example F

*Tetranychus Test (OP-Resistent/Dip Treatment)*
Solvent: 30 parts by weight of dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse red spider mite (*Tetranychus urticae*) are dipped into a preparation of active compound of the desired concentration.

After the desired period of time, the effect in % is determined. 100% means that all spider mites have been killed; 0% means that none of the spider mites have been killed.

Active compounds and tests results are shown in the Table below.

TABLE F plant-damaging mites
Tetranychus Test (OP-resistent/dip treatment)

| Active compounds | Concentration of active compound in ppm | Kill rate in % after $7^d$ |
|---|---|---|
| (structure) | 500 | 80 |

Example G

*Diabrotica balteata* Test (Larvae in Soil)

Critical Concentration Test/Soil Insects—Treatment of Transgenic Plants

Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of the active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trademark of Monsanto Comp., USA) are placed into each pot.

After 2 days, the corresponding test insects are placed into the treated soil. After a further 7 days, the efficacy of the active compound is determined by counting the number of maize plants that have emerged (1 plant=20% activity).

Example H

*Heliothis virescens* Test (Treatment of Transgenic Plants)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Soyabean shoots (*Glycine max*) of the cultivar Roundup Ready (trademark of Monsanto Comp. USA) are treated by being dipped into the preparation of active compound of the desired concentration and are populated with the tobacco bud worm caterpillar *Heliothis virescens* while the leaves are still moist.

After the desired period of time, the kill in % is determined. 100% means that all caterpillars have been killed; 0% means that none of the caterpillars have been killed.

What is claimed is:

1. A $\Delta^1$ pyrroline of the Formula (I)

(I)

in which
$R^1$ represents halogen, in each case optionally substituted alkyl or alkoxy or —S(O)$_w$R$^4$,
$R^2$ and $R^3$ independently of one another represent hydrogen, halogen or in each case optionally substituted alkyl, alkoxy or alkoxyalkyl,
$R^4$ represents optionally substituted alkyl,
Het represents heteroaryl which is optionally mono- or polysubstituted by identical or different $R^5$,
$R^5$ represents the grouping —X—Y-Z-E with the proviso that Y does not represent a direct bond if X does not represent a direct bond,
X represents a direct bond, oxygen, —S(O)$_w$—, —NR$^6$—, carbonyl, carbonyloxy, oxycarbonyl, oxysulphonyl (OSO$_2$), alkylene, halogenalkylene, alkenylene, halogenoalkenylene, alkinylene, alkyleneoxy, oxyalkylene, oxyalkyleneoxy, —S(O)$_w$-alkylene, cyclopropylene or oxiranylene, Y represents a direct bond or represents in each case optionally substituted phenylene, naphthylene, tetrahydronaphthylene or heterocyclylene, Z represents a direct bond or —(CH$_2$)$_n$—, E represents hydrogen, halogen, hydroxyl, cyano, formyl, nitro, trialkylsilyl, pentafluorothio, —S(O)$_w$R$^7$, —OSO$_2$R$^7$, —NR$^8$R$^9$, —COR$^7$, —CO$_2$R$^7$, —OC(O)R$^7$, —CONR$^{10}$R$^{11}$, —N(R$^{12}$)COR$^{13}$, —C(R$^{14}$)=N—OR$^{15}$, —SO$_2$NR$^{16}$R$^{17}$; represents in each case optionally substituted alkyl, alkenyl, alkinyl, alkoxy, alkenyloxy, cycloalkyl, cycloalkylalkyl, cycloalkyloxy, aryl, arylalkyl, aryloxy, aryloxyalkyl, saturated or unsaturated heterocyclyl or heterocyclylalkyl, R$^6$ represents in each case optionally substituted alkyl, cycloalkyl, cycloalkylalkyl, aryl or arylalkyl, R$^7$ represents in each case optionally substituted alkyl, cycloalkyl, aryl or arylalkyl, R$^8$ and R$^9$ independently of one another represent hydrogen, —SO$_2$R$^7$, —COR$^7$, —CO$_2$R$^7$, represent in each case optionally substituted alkyl, alkenyl, cycloalkyl, cycloalkylalkyl, aryl, arylalkyl or saturated or unsaturated heterocyclyl or heterocyclylalkyl, or R$^8$ and R$^9$ furthermore together represent in each case optionally substituted alkenylene or alkylene, where the alkylene chain may in each case be interrupted by —O—, —S— or —NR$^{18}$—, R$^{10}$ and R$^{11}$ independently of one another represent hydrogen, —SO$_2$R$^7$, represent in each case optionally substituted alkyl, alkenyl, cycloalkyl, cycloalkylalkyl, aryl, arylalkyl or saturated or unsaturated heterocyclyl or heterocyclylalkyl, or R$^{10}$ and R$^{11}$ furthermore together represent optionally substituted alkylene, where the alkylene chain may in each case be interrupted by —O—, —S— or —NR$^{18}$—, R$^{12}$ and R$^{13}$ independently of one another represent hydrogen, represent in each case optionally substituted alkyl, cycloalkyl, cycloalkylalkyl, aryl or arylalkyl, or R$^{12}$ and R$^{13}$ furthermore together represent in each case optionally substituted alkylene or alkenylene, R$^{14}$ and R$^{15}$ independently of one another represent hydrogen, represent in each case optionally substituted alkyl or alkenyl, R$^{16}$ and R$^{17}$ independently of one another represent hydrogen, represent optionally substituted alkyl or cycloalkyl, or R$^{16}$ and R$^{17}$ furthermore together represent optionally substituted alkylene, alkoxyalkylene or alkylthioalkylene, R$^{18}$ represents hydrogen, —SO$_2$R$^7$, —COR$^7$ or —CO$_2$R$^7$; represents in each case optionally substituted alkyl, alkenyl, cycloalkyl, cycloalkylalkyl, aryl, arylalkyl or saturated or unsaturated heterocyclyl or heterocyclylalkyl, w represents 0, 1 or 2, n represents 1, 2, 3 or 4.

2. The Δ$^1$ pyrroline of the Formula (I) according to claim 1, in which

R$^1$ represents halogen, alkyl, halogenoalkyl, alkoxy, halogenoalkoxy or —S(O)$_w$R$^4$, R$^2$ and R$^3$ independently of one another represent hydrogen, halogen, alkyl, halogenoalkyl, alkoxy, halogenoalkoxy or alkoxyalkyl, R$^4$ represents alkyl or halogenoalkyl, Het represents 5- to 14-membered heteroaryl which comprises 1 to 3 aromatic rings and one or more heteroatoms from the group consisting of nitrogen, oxygen and sulphur and is optionally mono- to tetrasubstituted by identical or different R$^5$, R$^5$ represents the grouping —X—Y-Z-E, with the proviso that Y does not represent a direct bond if X does not represent a direct bond, X represents a direct bond, oxygen, —S(O)$_w$—, —NR$^6$—, carbonyl, carbonyloxy, oxycarbonyl, oxysulphonyl (OSO$_2$), alkylene, halogenoalkylene, alkenylene, halogenoalkenylene, alkinylene, alkyleneoxy, oxyalkylene, oxyalkyleneoxy, —S(O)$_w$-alkylene, cyclopropylene or oxiranylene, Y represents a direct bond or represents phenylene, naphthalene, tetrahydronaphthalene or 5- to 10-membered saturated or unsaturated heterocyclylene having one or more heteroatoms from the group consisting of nitrogen, oxygen and sulphur, each of which radicals is optionally mono- to tetrasubstituted by identical or different radicals from the list W$^1$, Z represents a direct bond or —(CH$_2$)$_n$—, E represents hydrogen, halogen, hydroxyl, cyano, formyl, nitro, trialkylsilyl, pentafluorothio, —S(O)$_w$R$^7$, —OSO$_2$R$^7$, —NR$^8$R$^9$, —COR$^7$, —CO$_2$R$^7$, —OC(O)R$^7$, —CONR$^{10}$R$^{11}$, —N(R$^{12}$)COR$^{13}$, —C(R$^{14}$)=N—OR$^{15}$, —SO$_2$NR$^{16}$R$^{17}$; represents alkyl, alkenyl, alkinyl, alkoxy, alkenyloxy; each of which is optionally mono- or polysubstituted by identical or different substituents from the group consisting of halogen, cyano, alkoxy and/or —NR$^8$R$^9$; or represents cycloalkyl, cycloalkylalkyl, cycloalkyloxy, aryl, arylalkyl, aryloxy, aryloxyalkyl, saturated or unsaturated 5- to 10-membered heterocyclyl or heterocyclylalkyl having one or more heteroatoms from the group consisting of nitrogen, oxygen and sulphur, each of which radicals is optionally mono- or polysubstituted by identical or different substituents from the group consisting of halogen, cyano, nitro, alkyl, halogenoalkyl, alkenyl, halogenoalkenyl, alkoxy, halogenoalkoxy, alkylthio and halogenoalkylthio, W$^1$ represents halogen, cyano, formyl, nitro, trialkylsilyl, alkyl, halogenoalkyl alkyl, alkoxy, halogenoalkoxy, alkenyl, halogenoalkenyl, alkenyloxy, halogenoalkenyloxy, alkylcarbonyl, alkoxycarbonyl, —S(O)$_w$R$^7$, —C(R$^{14}$)=N—OR$^{15}$, —SO$_2$NR$^{16}$R$^{17}$, —(CH$_2$)$_p$NR$^{16}$R$^{17}$, —(CH$_2$)$_p$N(R$^{16}$)COR$^{17}$, —(CH$_2$)$_p$N(R$^{16}$)SO$_2$R$^{17}$, —OSO$_2$R$^{16}$, —OSO$_2$NR$^{16}$R$^{17}$, R$^6$ represents alkyl, halogenoalkyl or represents cycloalkyl, cycloalkylalkyl, aryl or arylalkyl, each of which is optionally mono- or polysubstituted by identical or different substituents from the group consisting of halogen, alkyl, halogenoalkyl, alkoxy, halogenoalkoxy, alkylthio and/or halogenoalkylthio, R$^7$ represents alkyl which is optionally mono- or polysubstituted by identical or different substituents from the group consisting of halogen and —NR$^8$R$^9$, represents cycloalkyl, aryl or arylalkyl, each of which is optionally mono- or polysubstituted by identical or different substituents from the group consisting of halogen, cyano, alkyl, halogenoalkyl, alkoxy, halogenoalkoxy, alkylthio and halogenoalkylthio, $R^8$ and $R^9$ independently of one another represent hydrogen, —SO$_2$R$^7$, —COR$^7$, —CO$_2$R$^7$, represent alkyl or alkenyl, each of which is optionally mono- or polysubstituted by identical or different substituents from the group consisting of halogen, alkylcarbonyl, alkylcarbonyloxy, alkylamino, dialkylamino, alkoxy, halogenoalkoxy, alkylthio and halogenoalkylthio; represents cycloalkyl, cycloalkylalkyl, aryl, arylalkyl or saturated or unsaturated 5- to 10-membered heterocyclyl or heterocyclylalkyl having one or more heteroatoms from the group consisting of nitrogen, oxygen and sulphur, each of which radicals is optionally mono- or polysubstituted by identical or different substituents from the group consisting of halogen, cyano, alkyl, halogenoalkyl, alkoxy, halogenoalkoxy, alkylthio and halogenoalkylthio, or $R^8$ and $R^9$ furthermore together represent alkenylene which is optionally mono- or polysubstituted by identical or different substituents from the group consisting of halogen, cyano, alkoxy, halogenoalkoxy, alkylthio and halogenoalkylthio or represent alkylene which is optionally mono- or polysubstituted by identical or different substituents from the group consisting of halogen, cyano, alkyl, halogenoalkyl, alkoxy, halogenoalkoxy, alkylthio and halogenoalkylthio, where the alkylene chain may in each case be interrupted by —O—, —S— or —NR$^{18}$—, $R^{10}$ and $R^{11}$ independently of one another represent hydrogen, —SO$_2$R$^7$, represent alkyl or alkenyl, each of which is optionally mono- or polysubstituted by identical or different substituents from the group consisting of halogen, alkylamino, dialkylamino, alkoxy and alkylthio; represent cycloalkyl, cycloalkylalkyl, aryl, arylalkyl or saturated or unsaturated 5- to 10-membered heterocyclyl or heterocyclylalkyl having one or more heteroatoms from the group consisting of nitrogen, oxygen and sulphur, each of which radicals is optionally mono- or polysubstituted by identical or different substituents from the group consisting of halogen, cyano, alkyl, halogenoalkyl, alkoxy, halogenoalkoxy, alkylthio and halogenoalkylthio, or $R^{10}$ and $R^{11}$ furthermore together represent alkylene which is optionally mono- or polysubstituted by identical or different substituents from the group consisting of halogen, cyano, alkyl, halogenoalkyl, alkoxy, halogenoalkoxy, alkylthio and halogenoalkylthio, where the alkylene chain may in each case be interrupted by —O—, —S— or —NR$^{18}$—, $R^{12}$ and $R^{13}$ independently of one another represent hydrogen, represent alkyl which is optionally mono- or polysubstituted by identical or different substituents from the group consisting of cyano, alkoxy and alkylthio, represent cycloalkyl, cycloalkylalkyl, aryl or arylalkyl, each of which is optionally mono- or polysubstituted by identical or different substituents from the group consisting of halogen, cyano, alkyl, halogenoalkyl, alkoxy, halogenoalkoxy, alkylthio and halogenoalkylthio, or $R^{12}$ and $R^{13}$ furthermore together represent alkylene or alkenylene, each of which is optionally mono- or polysubstituted by identical or different substituents from the group consisting of halogen, alkyl, halogenoalkyl, alkoxy, halogenoalkoxy, alkylthio and halogenoalkylthio, $R^{14}$ and $R^{15}$ independently of one another represent hydrogen, represent alkyl, halogenoalkyl, alkenyl or halogenoalkenyl, $R^{16}$ and $R^{17}$ independently of one another represent hydrogen, alkyl, halogenoalkyl or represent cycloalkyl which is optionally mono- or polysubstituted by identical or different substituents from the group consisting of halogen and alkyl, or $R^{16}$ and $R^{17}$ furthermore together represent alkylene, alkoxyalkylene or alkylthioalkylene, each of which is optionally mono- or polysubstituted by identical or different substituents from the group consisting of halogen and alkyl, $R^{18}$ represents hydrogen, —SO$_2$R$^7$, —COR$^7$ or —CO$_2$R$^7$; represents alkyl or alkenyl, each of which is optionally mono- or polysubstituted by identical or different substituents from the group consisting of halogen, cyano, alkylamino, dialkylamino, alkoxy, halogenoalkoxy, alkylthio and halogenalkylthio; represents cycloalkyl, cycloalkylalkyl, aryl, arylalkyl, saturated or unsaturated 5- to 10-membered heterocyclyl or heterocyclylalkyl having one or more heteroatoms from the group consisting of nitrogen, oxygen and sulphur, each of which radicals is optionally mono- or polysubstituted by identical or different substituents from the group consisting of halogen, cyano, alkyl, halogenoalkyl, alkoxy, halogenoalkoxy, alkylthio and halogenoalkylthio, w represents 0, 1 or 2, n represents 1, 2, 3 or 4, p represents 0, 1 or 2.

3. The $\Delta^1$ pyrroline of the Formula (I) according to claim 1, in which $R^1$ represents halogen, $C_1$–$C_6$-alkyl, $C_1$–$C_6$-halogenoalkyl, $C_1$–$C_6$-alkoxy, $C_1$–$C_6$-halogenoalkoxy or —S(O)$_w$R$^4$, $R^2$ and $R^3$ independently of one another represent hydrogen, halogen, $C_1$–$C_6$-alkyl, $C_1$–$C_6$-halogenoalkyl, $C_1$–$C_6$-alkoxy, $C_1$–$C_6$-halogenoalkoxy or $C_1$–$C_6$-alkoxy-$C_1$–$C_6$-alkyl, $R^4$ represents $C_1$–$C_6$-alkyl or $C_1$–$C_6$-halogenoalkyl, Het represents 5- to 14-membered heteroaryl which comprises 1 to 3 aromatic rings and 1 to 4 heteroatoms including 0 to 4 nitrogen atoms, 0 to 2 nonadjacent oxygen atoms and/or 0 to 2 nonadjacent sulphur atoms (in particular thienyl, benzothienyl, furyl, benzofuryl, indolyl, thienothienyl, thienofuryl, thienobenzothienyl, thienobenzofuryl, pyridinyl, pyrimidinyl, pyridazinyl, pyrazinyl, triazolyl or tetrazolyl), each of which radicals is optionally mono- to tetrasubstituted by identical or different $R^5$, $R^5$ represents the grouping —X—Y-Z-E, with the proviso that Y does not represent a direct bond if X does not represent a direct bond, X represents a direct bond, oxygen, —S(O)$_w$—, —NR$^6$—, carbonyl, carbonyloxy, oxycarbonyl, oxysulphonyl (OSO$_2$), $C_1$–$C_6$-alkylene, $C_1$–$C_6$-halogenoalkylene, $C_2$–$C_6$-alkenylene, $C_2$–$C_6$-halogenoalkenylene, $C_2$–$C_6$-alkinylene, $C_1$–$C_6$-alkyleneoxy, $C_1$–$C_6$-oxyalkylene, oxy-$C_1$–$C_6$-alkylene-oxy, —S(O)$_w$—$C_1$–$C_6$-alkylene, cyclopropylene or oxiranylene, Y represents a direct bond or represents 1,4-phenylene, 1,3-phenylene, 1,2-phenylene, 2,6-naphthylene, 2,7-naphthylene, 1,4-naphthylene, 2,6-(1,2,3,4-tetrahydro) naphthylene, 2,7-(1,2,3,4-tetrahydro)-naphthylene, 1,4-(1,2,3,4-tetrahydro)naphthylene, 5,8-(1,2,3,4-tetrahydro)naphthylene, each of which is optionally mono- to tetrasubstituted by identical or different radicals from the list W$^1$; or represents 5- or 6-membered saturated or unsaturated heterocyclylene which comprises 1 to 3 heteroatoms including 0 to 3 nitrogen atoms, 0 to 2 nonadjacent oxygen atoms and/or 0 to 2 nonadjacent sulphur atoms (in particular furylene, thienylene, pyrrolylene, oxazolylene, thiazolylene, pyridinylene, pyrimidinylene, pyridazinylene or pyrazinylene), each of which radicals is optionally mono- to tetrasubstituted by identical or different radicals from the list $W^1$, Z represents a direct bond or $-(CH_2)_n-$, E represents hydrogen, fluorine, chlorine, bromine, hydroxyl, cyano, formyl, nitro, tri-($C_1$–$C_6$-alkyl)silyl, pentafluorothio, $-S(O)_wR^7$, $-OSO_2R^7$, $-NR^8R^9$, $-COR^7$, $-CO_2R^7$, $-OC(O)R^7$, $-CONR^{10}R^{11}$, $-N(R^{12})COR^{13}$, $-C(R^{14})=N-OR^{15}$, $-SO_2NR^{16}R^{17}$; represents $C_1$–$C_{20}$-alkyl, $C_2$–$C_{20}$-alkenyl, $C_2$–$C_{10}$-alkinyl, $C_1$–$C_{20}$-alkoxy, $C_2$–$C_{20}$-alkenyloxy, each of which is optionally mono- or polysubstituted by identical or different radicals from the group consisting of halogen, cyano, $C_1$–$C_{10}$-alkoxy and $-NR^8R^9$; or represents $C_3$–$C_{12}$-cycloalkyl, $C_3$–$C_7$-cycloalkyl-$C_1$–$C_4$-alkyl, $C_3$–$C_{12}$-cycloalkyloxy, aryl, aryl-$C_1$–$C_4$-alkyl, aryloxy, aryloxy-$C_1$–$C_4$-alkyl, saturated or unsaturated 5- to 10-membered heterocyclyl or heterocyclyl-$C_1$–$C_4$-alkyl which comprises 1 to 4 heteroatoms including 0 to 4 nitrogen atoms, 0 to 2 nonadjacent oxygen atoms and/or 0 to 2 nonadjacent sulphur atoms (in particular tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, piperidino, morpholinyl, thiomorpholinyl, morpholino, thiomorpholino, triazinyl, triazolyl, quinolinyl or isoquinolinyl), each of which radicals is optionally mono- to tetrasubstituted by identical or different substituents from the group consisting of halogen, cyano, nitro, $C_1$–$C_6$-alkyl, $C_1$–$C_6$-halogenoalkyl, $C_2$–$C_6$-alkenyl, $C_2$–$C_6$-halogenoalkenyl, $C_1$–$C_6$-alkoxy, $C_1$–$C_6$-halogenoalkoxy, $C_1$–$C_6$-alkylthio and $C_1$–$C_6$-halogenoalkylthio, $W^1$ represents fluorine, chlorine, bromine, cyano, formyl, nitro, tri-($C_1$–$C_6$-alkyl)silyl, $C_1$–$C_6$-alkyl, $C_1$–$C_6$-halogenoalkyl, $C_1$–$C_6$-alkoxy, $C_1$–$C_6$-halo-genoalkoxy, $C_2$–$C_6$-alkenyl, $C_2$–$C_6$-halogenoalkenyl, $C_2$–$C_6$-alkenyloxy, $C_2$–$C_6$-halogenoalkenyloxy, $C_1$–$C_6$-alkylcarbonyl, $C_1$–$C_6$-alkoxycarbonyl, $-S(O)_wR^7$, $-C(R^{14})=N-OR^{15}$, $-SO_2NR^{16}R^{17}$, $-(CH_2)_pNR^{16}R^{17}$, $-(CH_2)_pN(R^{16})COR^{17}$, $-(CH_2)_pN(R^{16})SO_2R^{17}$, $-OSO_2R^{16}$, $-OSO_2NR^{16}R^{17}$, $R^6$ represents $C_1$–$C_6$-alkyl, $C_1$–$C_6$-halogenoalkyl or represents $C_3$–$C_7$-cycloalkyl, $C_3$–$C_6$-cycloalkyl-$C_1$–$C_4$-alkyl, aryl or aryl-$C_1$–$C_4$-alkyl, each of which is optionally mono- to tetrasubstituted by halogen, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio, $R^7$ represents $C^1C^{20}$-alkyl which is optionally mono- or polysubstituted by identical or different substituents from the group consisting of halogen and $-NR^8R^9$, represents $C_3$–$C_6$-cycloalkyl, aryl or aryl-$C_1$–$C_4$-alkyl, each of which is optionally mono- to octasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio, $R^8$ and $R^9$ independently of one another represent hydrogen, $-SO_2R^7$, $-COR^7$, $-CO_2R^7$, represent $C_1$–$C_{20}$-alkyl or $C_2$–$C_{20}$-alkenyl, each of which is optionally mono- or polysubstituted by identical or different substituents from the group consisting of halogen, $C_1$–$C_6$-alkylcarbonyl, $C_1$–$C_6$-alkyl-carbonyloxy, $C_1$–$C_6$-alkylamino, di-($C_1$–$C_6$-alkyl)amino, $C_1$–$C_6$-alkoxy, $C_1$–$C_6$-halogenoalkoxy, $C_1$–$C_6$-alkylthio, $C_1$–$C_6$-halogenoalkylthio; represent $C_3$–$C_{12}$-cycloalkyl, $C_3$–$C_7$-cycloalkyl-$C_1$–$C_4$-alkyl, aryl, aryl-$C_1$–$C_4$-alkyl or saturated or unsaturated 5- to 10-membered heterocyclyl or heterocyclyl-$C_1$–$C_4$-alkyl which comprises 1 to 4 heteroatoms including 0 to 4 nitrogen atoms, 0 to 2 nonadjacent oxygen atoms and/or 0 to 2 nonadjacent sulphur atoms (in particular tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl), each of which radicals is optionally mono- to tetrasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio or $C_1$–$C_6$-halogenoalkylthio, or $R^8$ and $R^9$ furthermore together represent $C_2$–$C_{12}$-alkenylene which is optionally mono- or polysubstituted by identical or different substituents from the group consisting of halogen, cyano, $C_1$–$C_6$-alkoxy, $C_1$–$C_6$-halogenoalkoxy, $C_1$–$C_6$-alkylthio and $C_1$–$C_6$-halogenoalkylthio or represent $C_3$–$C_{12}$-alkylene which is optionally mono- or polysubstituted in the alkylene moiety by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio, where the alkylene chain may in each case be interrupted by $-O-$, $-S-$ or $-NR^{18}-$, $R^{10}$ and $R^{11}$ independently of one another represent hydrogen, $-SO_2R^7$, represents $C_1$–$C_6$-alkyl or $C_2$–$C_6$-alkenyl, each of which is optionally mono- to tridecasubstituted by identical or different substituents from the group consisting of halogen, $C_1$–$C_6$-alkylamino, di-($C_1$–$C_6$-alkyl)amino, $C_1$–$C_6$-alkoxy, $C_1$–$C_6$-halogenoalkoxy, $C_1$–$C_6$-alkylthio and $C_1$–$C_6$-halogenoalkylthio; represent $C_3$–$C_7$-cycloalkyl, $C_3$–$C_7$-cycloalkyl-$C_1$–$C_4$-alkyl, aryl, aryl-$C_1$–$C_4$-alkyl or saturated or unsaturated 5- to 10-membered heterocyclyl or heterocyclyl-$C_1$–$C_4$-alkyl which comprises 1 to 4 heteroatoms including 0 to 4 nitrogen atoms, 0 to 2 nonadjacent oxygen atoms and/or 0 to 2 nonadjacent sulphur atoms (in particular tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl), each of which radicals is optionally mono- to tetrasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio, or $R^{10}$ and $R^{11}$ furthermore together represent $C_3$–$C_6$-alkylene, —$(CH_2)_2$—O—$(CH_2)_2$—, —$(CH_2)_2$—S—$(CH_2)_2$— or —$(CH_2)_2$—N($R^{18}$)—$(CH_2)_2$—, each of which is optionally mono- to tetrasubstituted in the alkylene moiety by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio, $R^{12}$ and $R^{13}$ independently of one another represent hydrogen, represent $C_1$–$C_6$-alkyl which is optionally mono- to tridecasubstituted by identical or different substituents from the group consisting of halogen, cyano, $C_1$–$C_6$-alkoxy and $C_1$–$C_6$-alkylthio, represent $C_3$–$C_7$-cycloalkyl, $C_3$–$C_7$-cycloalkyl-$C_1$–$C_4$-alkyl, aryl or aryl-$C_1$–$C_4$-alkyl, each of which is optionally mono- to octasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio, or $R^{12}$ and $R^{13}$ furthermore together represent $C_3$–$C_{10}$-alkylene or $C_3$–$C_{10}$-alkenylene, each of which is optionally mono- to octasubstituted by identical or different substituents from the group consisting of halogen, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio, $R^{14}$ and $R^{15}$ independently of one another represent hydrogen, represent $C_1$–$C_6$-alkyl, $C_1$–$C_6$-halogenoalkyl, $C_2$–$C_6$-alkenyl or $C_2$–$C_6$-halogenoalkenyl, $R^{16}$ and $R^{17}$ independently of one another represent hydrogen, $C_1$–$C_6$-alkyl, $C_1$–$C_6$-halogenoalkyl or represent $C_3$–$C_7$-cycloalkyl which is optionally mono- to octasubstituted by identical or different substituents from the group consisting of fluorine, chlorine, bromine and/or $C_1$–$C_6$-alkyl, or $R^{16}$ and $R^{17}$ furthermore together represent $C_3$–$C_6$-alkylene, $C_1$–$C_3$-alkoxy-$C_1$–$C_3$-alkylene or $C_1$–$C_3$-alkylthio-$C_1$–$C_3$-alkylene, each of which is optionally mono- to nonasubstituted by identical or different substituents from the group consisting of fluorine, chlorine, bromine and $C_1$–$C_6$-alkyl, $R^{18}$ represents hydrogen, —$SO_2R^7$, —$COR^7$ or —$CO_2R^7$; represents $C_1$–$C_{20}$-alkyl or $C_2$–$C_{20}$-alkenyl, each of which is optionally mono- or polysubstituted by identical or different substituents from the group consisting of halogen, cyano, $C_1$–$C_6$-alkylamino, di-($C_1$–$C_6$-alkyl)amino, $C_1$–$C_6$-alkoxy, $C_1$–$C_6$-halogenoalkoxy, $C_1$–$C_6$-alkylthio and $C_1$–$C_6$-halogenoalkylthio; represents $C_3$–$C_{12}$-cycloalkyl, $C_3$–$C_7$-cycloalkyl-$C_1$–$C_4$-alkyl, aryl, aryl-$C_1$–$C_4$-alkyl, saturated or unsaturated 5- to 10-membered heterocyclyl or heterocyclyl-$C_1$–$C_4$-alkyl which comprises 1 to 4 heteroatoms including 0 to 4 nitrogen atoms, 0 to 2 nonadjacent oxygen atoms and/or 0 to 2 nonadjacent sulphur atoms (in particular tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl), each of which radicals is optionally mono- to tetrasubstituted by identical or different substituents from the group consisting of halogen, cyano, $C_1$–$C_6$-alkyl, $C_1$–$C_6$-halogenoalkyl, $C_1$–$C_6$-alkoxy, $C_1$–$C_6$-halogenoalkoxy, $C_1$–$C_6$-alkylthio and $C_1$–$C_6$-halogenoalkylthio, w represents 0, 1 or 2, n represents 1, 2 or 3, p represents 0, 1 or 2.

4. The $\Delta^1$ pyrroline of the Formula (I) according to claim 1, in which $R^1$ represents fluorine, chlorine, bromine, $C_1$–$C_4$-alkyl, $C_1$–$C_4$-halogenoalkyl having 1 to 9 fluorine, chlorine and/or bromine atoms, $C_1$–$C_4$-alkoxy, $C_1$–$C_4$-halogenoalkoxy having 1 to 9 fluorine, chlorine and/or bromine atoms or —$S(O)_wR^4$, $R^2$ and $R^3$ independently of one another represent hydrogen, fluorine, chlorine, bromine, $C_1$–$C_4$-alkyl, $C_1$–$C_4$-halogenoalkyl having 1 to 9 fluorine, chlorine and/or bromine atoms, $C_1$–$C_4$-alkoxy or $C_1$–$C_4$-halogenoalkoxy having 1 to 9 fluorine, chlorine and/or bromine atoms, $R^4$ represents $C_1$–$C_4$-alkyl or represents in each case fluorine- or chlorine-substituted methyl or ethyl, Het represents 2-thienyl, 3-thienyl, 2-benzo[b]thienyl, 2-furyl, 3-furyl, 2-benzo[b]furyl, 2-indolyl, 2-thieno[3,2-b]thienyl, 2-thieno[3,2-b]furyl, 5-thieno[3,2-b]furyl, 2-thieno[2,3-f][1]benzothienyl, 2-thieno[2,3-f][1]benzo-furyl, 6-thieno[2,3-f]]1]benzofuryl, 2-pyridinyl, 3-pyridinyl, 2-pyrimidinyl, 5-pyrimidinyl, 3-pyridazinyl, 4-pyridazinyl, 2-pyrazinyl, triazolyl or tetrazolyl, each of which is optionally mono- to trisubstituted by identical or different $R^5$, $R^5$ represents the grouping —X—Y-Z-E, with the proviso that Y does not represent a direct bond if X does not represent a direct bond, X represents a direct bond, oxygen —$S(O)_w$—, —$NR^6$—, carbonyl, carbonyloxy, oxycarbonyl, oxysulphonyl ($OSO_2$), $C_1$–$C_4$-alkylene, $C_1$–$C_4$-halogenoalkylene having 1 to 8 fluorine, chlorine and/or bromine atoms, $C_2$–$C_4$-alkenylene, $C_2$–$C_4$-halogenoalkenylene having 1 to 6 fluorine, chlorine and/or bromine atoms, $C_2$–$C_4$-alkinylene, $C_1$–$C_4$-alkyleneoxy, oxy-$C_1$–$C_4$-alkylene, oxy-$C_1$–$C_4$-alkyleneoxy or —$S(O)_w$—$C_1$–$C_4$-alkylene, Y represents a direct bond or represents 1,4-phenylene, 1,3-phenylene, 1,2-phenylene, 2,6-naphthylene, 2,7-naphthylene, 1,4-naphthylene, 2,6-(1,2,3,4-tetrahydro) naphthylene, 2,7-(1,2,3,4-tetrahydro)-naphthylene, 1,4-(1,2,3,4-tetrahydro)naphthylene, 5,8-(1,2,3,4-tetrahydro)naphthylene, 2,4-furylene, 2,4-thienylene, 2,4-pyrrolylene, 2,5-oxazolylene, 2,5-thiazolylene, 2,5-pyridinylene, 2,6-pyridinylene, 2,5-pyrimidinylene, 3,6-pyridazinylene or 2,5-pyrazinylene, each of which is optionally mono- to trisubstituted by identical or different radicals from the list $W^1$, Z represents a direct bond or —$(CH_2)_n$—, E represents hydrogen, fluorine, chlorine, bromine, hydroxyl, cyano, formyl, nitro, trimethylsilyl, dimethyl-tert-butylsilyl, —$S(O)_wR^7$, —$OSO_2R^7$, —$NR^8R^9$, —$COR^7$, —$CO_2R^7$, —$OC(O)R^7$, —$CONR^{10}R^{11}$, —$N(R^{12})COR^{13}$, —$SO_2NR^{16}R^{17}$; represents $C_1$–$C_{16}$-alkyl, $C_2$–$C_{16}$-alkenyl, $C_2$–$C_6$-alkinyl, $C_1$–$C_{16}$-alkoxy, $C_2$–$C_{16}$-alkenyloxy, each of which is optionally mono- or polysubstituted by identical or different substituents from the group consisting of fluorine, chlorine, bromine, cyano, $C_1$–$C_6$-alkoxy and —$NR^8R^9$; or represents $C_3$–$C_{10}$-cycloalkyl, $C_3$–$C_6$-cycloalkyl-$C_1$–$C_4$-alkyl, $C_3$–$C_{10}$-cycloalkyloxy, phenyl, phenoxy, benzyl, phenylethyl, benzyloxy, tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, piperidino, morpholinyl, thiomorpholinyl, morpholino, thiomorpholino, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_2$–$C_6$-alkenyl, $C_2$–$C_6$-halogenoalkenyl, $C_1$–$C_4$-alkoxy, $C_1$–$C_4$-halogenoalkoxy, $C_1$–$C_4$-alkylthio and $C_1$–$C_4$-halogenoalkylthio, $W^1$ represents fluorine, chlorine, bromine, cyano, formyl, trimethylsilyl, dimethyl-tert-butylsilyl, $C_1$–$C_4$-alkyl, $C_1$–$C_4$-alkoxy, $C_2$–$C_4$-alkenyl, $C_2$–$C_4$-alkenyloxy; represents $C_1$–$C_4$-halogenoalkyl, $C_1$–$C_4$-halogenoalkoxy having in each case 1 to 9 fluorine, chlorine and/or bromine atoms, $C_2$–$C_4$-halogenoalkenyl, $C_2$–$C_4$-halogenoalkenyloxy having in each case 1 to 8 fluorine, chlorine and/or bromine atoms; represents $C_1$–$C_4$-alkylcarbonyl, $C_1$–$C_4$-alkoxycarbonyl, —S(O)$_w$R$^7$, —SO$_2$NR$^{16}$R$^{17}$, —(CH$_2$)$_p$NR$^{16}$R$^{17}$, —(CH$_2$)$_p$N(R$^{16}$)COR$^{17}$, —(CH$_2$)$_p$N(R$^{16}$)SO$_2$R$^{17}$, —OSO$_2$R$^{16}$, —OSO$_2$NR$^{16}$R$^{17}$, $R^6$ represents methyl, ethyl, n-propyl, isopropyl, n-butyl, isobutyl, sec-butyl, tert-butyl, trifluoromethyl, trifluoroethyl, or represents cyclopropyl, cyclopropylmethyl, cyclopentyl, cyclopentylmethyl, cyclohexyl, cyclohexylmethyl, phenyl, benzyl or phenylethyl, each of which is optionally mono- to tetrasubstituted by identical or different substituents from the group consisting of fluorine, chlorine, bromine, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and $C_1$–$C_4$-halogenoalkylthio having in each case 1 to 9 fluorine, chlorine and/or bromine atoms, $R^7$ represents $C_1$–$C_{10}$-alkyl which is optionally mono- or polysubstituted by identical or different substituents from the group consisting of fluorine, chlorine, bromine and —NR$^8$R$^9$, represents cyclopropyl, cyclopentyl, cyclohexyl, phenyl or benzyl, each of which is optionally mono- to tetrasubstituted by identical or different substituents from the group consisting of fluorine, chlorine, bromine, cyano, $C_1$–$C_4$-alkyl, $C_1$–$C_4$-alkoxy, $C_1$–$C_4$-alkylthio, $C_1$–$C_4$-halogenoalkyl, $C_1$–$C_4$-halogenoalkoxy and $C_{1-4}$-halogenoalkylthio, $R^8$ and $R^9$ independently of one another represent hydrogen, —SO$_2$R$^7$, —COR$^7$, —CO$_2$R$^7$, represent $C_1$–$C_{16}$-alkyl or $C_2$–$C_{16}$-alkenyl, each of which is optionally mono- or polysubstituted by identical or different substituents from the group consisting of fluorine, chlorine, bromine, $C_1$–$C_4$-alkyl-carbonyl, $C_1$–$C_4$-alkylcarbonyloxy, $C_1$–$C_4$-alkylamino, di-($C_1$–$C_4$-alkyl)-amino, $C_1$–$C_4$-alkoxy, $C_1$–$C_4$-halogenoalkoxy, $C_1$–$C_4$-alkylthio and $C_1$–$C_4$-halogenoalkylthio; represent $C_3$–$C_{10}$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio, or $R^8$ and $R^9$ furthermore together represent $C_2C_{10}$-alkenylene which is optionally mono- or polysubstituted by identical or different substituents from the group consisting of fluorine, chlorine, bromine, $C_1$–$C_4$-alkoxy, $C_1$–$C_4$-halogenoalkoxy, $C_1$–$C_4$-alkylthio and $C_1$–$C_4$-halogenoalkylthio or represent $C_3$–$C_{10}$-alkylene, which is optionally mono- or polysubstituted in the alkylene moiety by identical or different substituents from the group consisting of fluorine, chlorine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio, where the alkylene chain may in each case be interrupted by —O—, —S— or —NR$^{18}$—, $R^{10}$ and $R^{11}$ independently of one another represent hydrogen, —SO$_2$R$^7$, represent $C_1$–$C_6$-alkyl or $C_2$–$C_6$-alkenyl, each of which is optionally mono- to nonasubstituted by identical or different substituents from the group consisting of fluorine, chlorine, bromine, $C_1$–$C_4$-alkylamino, di-($C_1$–$C_4$-alkyl)amino, $C_1$–$C_4$-alkoxy, $C_1$–$C_4$-halogenoalkoxy, $C_1$–$C_4$-alkylthio and $C_1$–$C_4$-halogenoalkylthio; represent $C_3$–$C_6$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio, or $R^{10}$ and $R^{11}$ furthermore together represent $C_4$–$C_6$-alkylene, —(CH$_2$)$_2$—O—(CH$_2$)$_2$—, —(CH$_2$)$_2$—S—(CH$_2$)$_2$ — or —(CH$_2$)$_2$—N(R$^{18}$)—(CH$_2$)$_2$—, each of which is optionally mono- to tetrasubstituted in the alkylene moiety by identical or different substituents from the group consisting of fluorine, chlorine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio, $R^{12}$ and $R^{13}$ independently of one another represent hydrogen, represent $C_1$–$C_6$-alkyl which is optionally mono- to nonasubstituted by identical or different substituents from the group consisting of fluorine, chlorine, bromine, $C_1$–$C_4$-alkoxy and $C_1$–$C_4$-alkylthio, represent $C_3$–$C_6$-cycloalkyl, $C_3$–$C_6$-cycloalkyl-$C_1$–$C_4$-alkyl, phenyl, benzyl or phenylethyl, each of which is optionally mono- to tetrasubstituted by identical or different substituents from the group consisting of fluorine, chlorine, bromine, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio, or $R^{12}$ and $R^{13}$ furthermore together represent $C_3$–$C_8$-alkylene or $C_3$–$C_8$-alkenylene, each of which is optionally mono- to tetrasubstituted by identical or different substituents from the group consisting of fluorine, chlo rine, bromine, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio, $R^{16}$ and $R^{17}$ independently of one another represent hydrogen, $C_1$–$C_6$-alkyl, $C_1$–$C_4$-halogenoalkyl having 1 to 9 fluorine, chlorine and/or bromine atoms or represent $C_3$–$C_6$-cycloalkyl which is optionally mono- to tetrasubstituted by identical or different substituents from the group consisting of fluorine, chlorine, bromine and $C_1$–$C_4$-alkyl, or $R^{16}$ and $R^{17}$ furthermore together represent —$(CH_2)_3$—, —$(CH_2)_4$—, —$(CH_2)_5$—, —$(CH_2)_2$—O—$(CH_2)_2$— or —$(CH_2)_2$—S—$(CH_2)_2$—, $R^{18}$ represents hydrogen, —$SO_2R^7$, represents —$COR^7$ or —$CO_2R^7$; represents $C_1$–$C_{16}$-alkyl or $C_2$–$C_{16}$-alkenyl, each of which is optionally mono- or polysubstituted by identical or different substituents from the group consisting of fluorine, chlorine, bromine, cyano, methylamino, ethylamino, di-($C_1$–$C_6$-alkyl)amino, $C_1$–$C_4$-alkoxy, $C_1$–$C_4$-halogenoalkoxy, $C_1$–$C_4$-alkylthio and $C_1$–$C_4$-halogenoalkylthio; represents $C_3$–$C_{10}$-cycloalkyl, $C_3$–$C_6$-cycloalkyl-$C_1$–$C_4$-alkyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio, w represents 0, 1 or 2, n represents 1 or 2, p represents 0 or 1.

5. The $\Delta^1$ pyrroline of the Formula (I) according to claim 1, in which $R^1$ represents fluorine, chlorine, bromine, methyl, trifluoromethyl, methoxy, trifluoromethoxy, methylthio or trifluoromethylthio, $R^2$ and $R^3$ independently of one another represent hydrogen, fluorine, chlorine, bromine, methyl, trifluoromethyl, methoxy or trifluoromethoxy, Het represents 2-thienyl, 3-thienyl, 2-benzo[b]thienyl, 2-furyl, 3-furyl, 2-benzo[b]furyl, 2-thieno[3,2-b]thienyl, 2-thieno[3,2-b]furyl, 5-thieno[3,2-b]furyl, 2-thieno[2,3-f][1]benzothienyl, 2-thieno[2,3-f][1]benzofuryl, 6-thieno[2,3-f][1]benzofuryl, 2-pyridinyl, 3-pyridinyl, 2-pyrimidinyl, 5-pyrimidinyl, 3-pyridazinyl, 4-pyridazinyl or 2-pyrazinyl, each of which is optionally mono- or disubstituted by identical or different $R^5$, $R^5$ represents the grouping —X—Y-Z-E, with the proviso that Y does not represent a direct bond if X does not represent a direct bond, X represents a direct bond, oxygen, sulphur, —$SO_2$—, —$NR^6$—, —CO—, —C(O)—O—, —O—C(O)—, —$CH_2$—, —$(CH_2)_2$—, —C=C— (E or Z), —C≡C—, —$CH_2$—O—, —$(CH_2)_2O$—, —$OCH_2$—, —$O(CH_2)_2$—, —O—$CH_2$—O—, —$SCH_2$—, —$S(CH_2)_2$—, —$CH_2S$— or —$(CH_2)_2S$—, Y represents a direct bond or represents 1,4-phenylene, 1,3-phenylene, 2,6-naphthylene, 2,7-naphthylene, 2,4-furylene, 2,4-thienylene, 2,5-pyridinylene, 2,5-pyrimidinylene, 3,6-pyridazinylene or 2,5-pyrazinylene, each of which is optionally mono- or disubstituted by identical or different dicals from the list $W^1$, Z represents a direct bond, methylene or ethylene, E represents hydrogen, fluorine, chlorine, bromine, hydroxyl, cyano, formyl, —$S(O)_wR^7$, —$OSO_2R^7$, —$NR^8R^9$, —$COR^7$, —$CO_2R^7$, —$OC(O)R^7$, —$CONR^{10}R^{11}$, —$N(R^{12})COR^{13}$, —$SO_2NR^{16}R^{17}$; represents $C_1$–$C_{16}$-alkyl, $C_2$–$C_{16}$-alkenyl, $C_1$–$C_{16}$-alkoxy, $C_2$–$C_{16}$-alkenyloxy, each of which is optionally mono- or polysubstituted by identical or different substituents from the group consisting of fluorine, chlorine, bromine, cyano, $C_1$–$C_6$-alkoxy and —$NR^8R^9$; or represents cyclopropyl, cyclopentyl, cyclohexyl, cyclopropyloxy, cyclopentyloxy, cyclohexyloxy, cyclopropylmethyl, cyclopentylmethyl, cyclohexylmethyl, phenyl, phenoxy, benzyl, phenylethyl, benzyloxy, tetrazolyl, furyl, furfuryl, benzofuryl, tetrahydrofuryl, thienyl, thenyl, benzothienyl, thiolanyl, pyrrolyl, indolyl, pyrrolinyl, pyrrolidino, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, piperidino, morpholinyl, thiomorpholinyl, morpholino, thiomorpholino, triazinyl, triazolyl, quinolinyl or isoquinolinyl, each of which is optionally mono- to trisubstituted by identical or different substituents from the group consisting of fluorine, chlorine, bromine, cyano, methyl, ethyl, n-propyl, isopropyl, —$CF_3$, —$CHF_2$, —$CClF_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, —$CF_2CHFCF_3$, vinyl, allyl, 1-propenyl, butenyl, —CF=CHF, —CF=$CH_2$, —CF=$CCl_2$, —CH=$CF_2$, —$CF_2CF$=$CF_2$, —CH=CFH, —$CH_2CF$=$CF_2$, —CF=$CF_2$, —$CF_2CH$=$CF_2$, methoxy, ethoxy, n-propoxy, isopropoxy, n-butoxy, isobutoxy, sec-butoxy, tert-butoxy, trifluoromethoxy, difluoromethoxy, chlorodifluoromethoxy, trifluoroethoxy, methylthio, ethylthio, n-propylthio, isopropylthio, n-butylthio, isobutylthio, sec-butylthio, tert-butylthio, trifluoromethylthio, difluoromethylthio, chlorodifluoromethylthio and trifluoroethylthio, $W^1$ represents fluorine, chlorine, bromine, cyano, formyl, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy, tert-butoxy, vinyl, allyl, trifluoromethyl, trifluoroethyl, trifluoromethoxy, trifluoroethoxy, —$OCF_2CF_2H$, —CH=$CF_2$, —CH=$CCl_2$, —OCF=$CF_2$, —COMe, —COEt, —$CO_2Me$, —$CO_2Et$, —$CO_2(t$-Bu), —SMe, —SOMe, —$SO_2Me$, —$SCF_3$, —$SOCF_3$, —$SO_2CF_3$, —$SCHF_2$, —$SOCHF_2$, —$SO_2CHF_2$, —$SO_2NMe_2$, —$NMe_2$, —$NEt_2$, —N(n-Pr)$_2$, —N(Me)COMe, —N(Me)COEt, —N(Me)COPr, —N(Me)CO(t-Bu), 2-pyrrolidonyl, 2-piperidonyl, —N(Me)$SO_2Me$, —N(Me)$SO_2Et$, —N(Me)$SO_2CF_3$, —N(Et)$SO_2CF_3$, —N(Me)$SO_2(CF_2)_3CF_3$ or —$OSO_2NMe_2$, $R^6$ represents methyl, ethyl, n-propyl, isopropyl, n-butyl, isobutyl, sec-butyl, tert-butyl, trifluoromethyl, trifluoroethyl, cyclopropyl, cyclopropylmethyl, cyclopentyl, cyclopentylmethyl, cyclohexyl, cyclohexylmethyl, phenyl, benzyl or phenylethyl, R[7] represents methyl, ethyl, n-propyl, isopropyl, n-butyl, isobutyl, sec-butyl, tert-butyl, pentyl, hexyl, —CF$_3$, —CHF$_2$, —CCl$_3$, —CCl$_2$F, dimethyl aminomethyl, dimethylaminoethyl, diethylaminomethyl, diethylaminoethyl, cyclopropyl, cyclopentyl, cyclohexyl, phenyl or benzyl, R[8] and R[9] independently of one another represent hydrogen, —SO$_2$R[7], —COR[7], —CO$_2$R[7], represent $C_1$–$C_{16}$-alkyl or $C_2$≠$C_4$-alkenyl, each of which is optionally mono- or polysubstituted by identical or different substituents from the group consisting of fluorine, chlorine, bromine, $C_1$–$C_4$-alkylcarbonyl, $C_1$–$C_4$-alkylcarbonyloxy, $C_1$–$C_4$-alkylamino, di-($C_1$–$C_4$-alkyl)amino, $C_1$–$C_4$-alkoxy, $C_1$–$C_4$-halogenoalkoxy, $C_1$–$C_4$-alkylthio and $C_1$–$C_4$-halogenoalkylthio; represent $C_3$–$C_8$-cycloalkyl, cyclopropylmethyl, cyclopentylmethyl, cyclohexylmethyl, cyclopropylethyl, cyclopentylethyl, cyclohexylethyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio and $C_1$–$C_4$-halogenoalkylthio, or R[8] and R[9] furthermore together represent $C_2$–$C_8$-alkenylene which is optionally mono- or polysubstituted by identical or different substituents from the group consisting of fluorine, chlorine, bromine, $C_1$–$C_4$-alkoxy, $C_1$–$C_4$-halogenoalkoxy, $C_1$–$C_4$-alkylthio and $C_1$–$C_4$-halogenoalkylthio or represent $C_3$–$C_8$-alkylene, which is optionally mono- or polysubstituted in the alkylene moiety by identical or different substituents from the group consisting of fluorine, chlorine, cyano, methyl, ethyl, n-propyl, isopropyl, n-butyl, isobutyl, sec-butyl, tert-butyl, $C_1$–$C_4$-halogenoalkyl, methoxy, ethoxy, n-propoxy, isopropoxy, n-butoxy, isobutoxy, sec-butoxy, tert-butoxy, $C_1$–$C_4$-halogenoalkoxy, methylthio, ethylthio, n-propylthio, isopropylthio, n-butylthio, isobutylthio, sec-butylthio, tert-butylthio and $C_1$–$C_4$-halogenoalkylthio, where the alkylene chain may in each case be interrupted by —O—, —S— or —NR[18]—, R[10] and R[11] independently of one another represent hydrogen, —SO$_{2CF3}$, methyl, ethyl, n-propyl, isopropyl, n-butyl, isobutyl, sec-butyl, tert-butyl, pentyl, hexyl, —CF$_3$, —CH$_2$CF$_3$, —(CF$_2$)$_3$CF$_3$, methoxymethyl, methoxyethyl, cyclopropyl, cyclopentyl, cyclohexyl, or represent phenyl or benzyl, each of which is optionally mono- to trisubstituted by identical or different substituents from the group consisting of fluorine, chlorine, bromine, methyl, trifluoromethyl, methoxy and trifluoromethoxy, or R[10] and R[11] furthermore together represent —(CH$_2$)$_4$—, —(CH$_2$)$_5$—, —(CH$_2$)$_6$—, —CH$_2$—CH(CH$_3$)—CH$_2$—CH(CH$_3$)—CH$_2$—, —(CH$_2$)$_2$—O—(CH$_2$)$_2$—, —(CH$_2$)$_2$—S—(CH$_2$)$_2$— or —(CH$_2$)$_2$—N(R[18])—(CH$_2$)$_2$—, R[12] and R[13] independently of one another represent hydrogen, methyl, ethyl, n-propyl, isopropyl, n-butyl, isobutyl, sec-butyl, tert-butyl, n-hexyl, trifluoromethyl, trifluoroethyl, cyclopropyl, cyclopentyl, cyclohexyl or represent phenyl or benzyl, each of which is optionally mono- to tetrasubstituted by identical or different substituents from the group consisting of fluorine, chlorine, bromine, methyl, trifluoromethyl, methoxy and trifluoromethoxy, or R[12] and R[13] furthermore together represent —(CH$_2$)$_3$—, —(CH$_2$)$_4$—, —(CH$_2$)$_5$— or —(CH$_2$)$_6$—, each of which is optionally mono- to tetrasubstituted by identical or different substituents from the group consisting of fluorine, chlorine, bromine, methyl, ethyl, methoxy, ethoxy, methylthio, ethylthio, trifluoromethyl, trifluoromethoxy and trifluoromethylthio, R[16] and R[17] independently of one another represent hydrogen, methyl, ethyl, n-propyl, isopropyl, n-butyl, isobutyl, sec-butyl, tert-butyl, n-hexyl, trifluoromethyl, trifluoroethyl, cyclopropyl, cyclopentyl or cyclohexyl, or R[16] and R[17] furthermore together represent —(CH$_2$)$_3$—, —(CH$_2$)$_4$—, —(CH$_2$)$_5$—, —(CH$_2$)$_2$—O—(CH$_2$)$_2$— or —(CH$_2$)$_2$—S—(CH$_2$)$_2$, R[18] represents hydrogen, —SO$_2$R[7], represents —COR[7] or —CO$_2$R[7]; represents $C_1$–$C_{16}$-alkyl or $C_2$–$C_{16}$-alkenyl, each of which is optionally mono- or polysubstituted by identical or different substituents from the group consisting of fluorine, chlorine, bromine, cyano, methylamino, ethylamino, di-($C_1$–$C_4$-alkyl)amino, $C_1$–$C_4$-alkoxy, $C_1$–$C_4$-halogenoalkoxy, $C_1$–$C_4$-alkylthio and $C_1$–$C_4$-halogenoalkylthio; represents $C_3$–$C_8$-cycloalkyl, cyclopropylmethyl, cyclopentylmethyl, cyclohexylmethyl, cyclopropylethyl, cyclopentylethyl, cyclohexylethyl, phenyl, benzyl, phenylethyl, tetrazolyl, furyl, furfuryl, benzofuryl, tetrahydrofuryl, thienyl, thenyl, benzothienyl, thiolanyl, pyrrolyl, indolyl, pyrrolinyl, pyrrolidinyl, oxazolyl, benzoxazolyl, isoxazolyl, imidazolyl, pyrazolyl, thiazolyl, benzothiazolyl, thiazolidinyl, pyridinyl, pyrimidinyl, pyridazyl, pyrazinyl, piperidinyl, morpholinyl, thiomorpholinyl, triazinyl, triazolyl, quinolinyl or isoquinolinyl, each of which is optionally mono- to trisubstituted by identical or different substituents from the group consisting of fluorine, chlorine, bromine, cyano, methyl, ethyl, n-propyl, isopropyl, n-butyl, isobutyl, sec-butyl, tert-butyl, $C_1$–$C_4$-halogenoalkyl, methoxy, ethoxy, n-propoxy, isopropoxy, n-butoxy, isobutoxy, sec-butoxy, tert-butoxy, $C_1$–$C_4$-halogenoalkoxy, methylthio, ethylthio, n-propylthio, isopropylthio, n-butylthio, isobutylthio, sec-butylthio, tert-butylthio and $C_1$–$C_4$-halogenoalkylthio.

6. A $\Delta^1$ pyrroline of the Formula

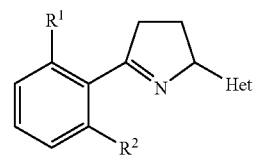

in which

R[1] represents fluorine or chlorine,

R[2] represents hydrogen or fluorine and

Het has the meaning given in claim 1.

7. A compound of the Formulae (I-1) to (I-16)
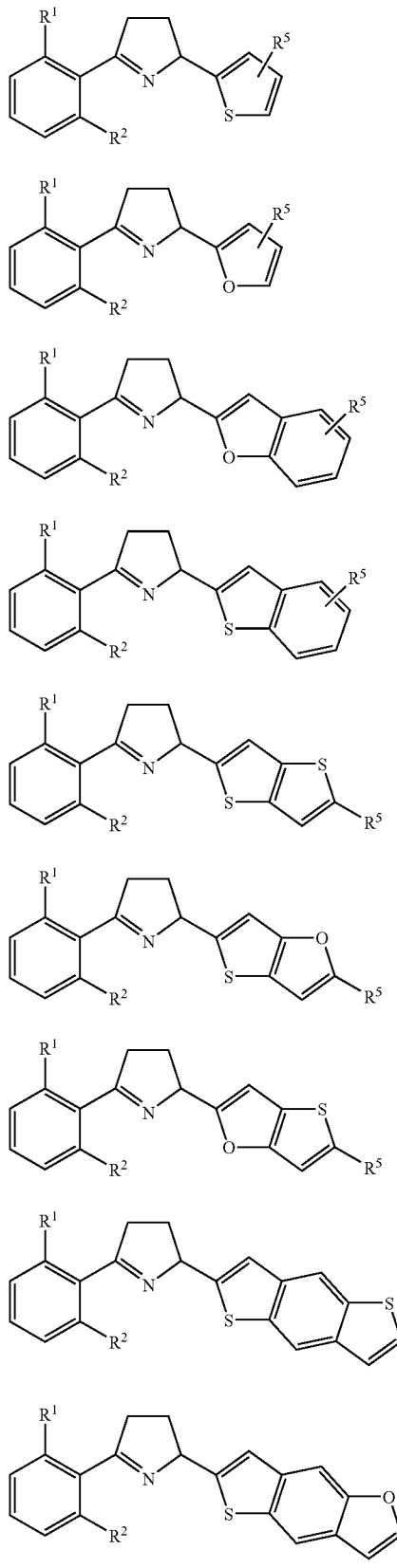
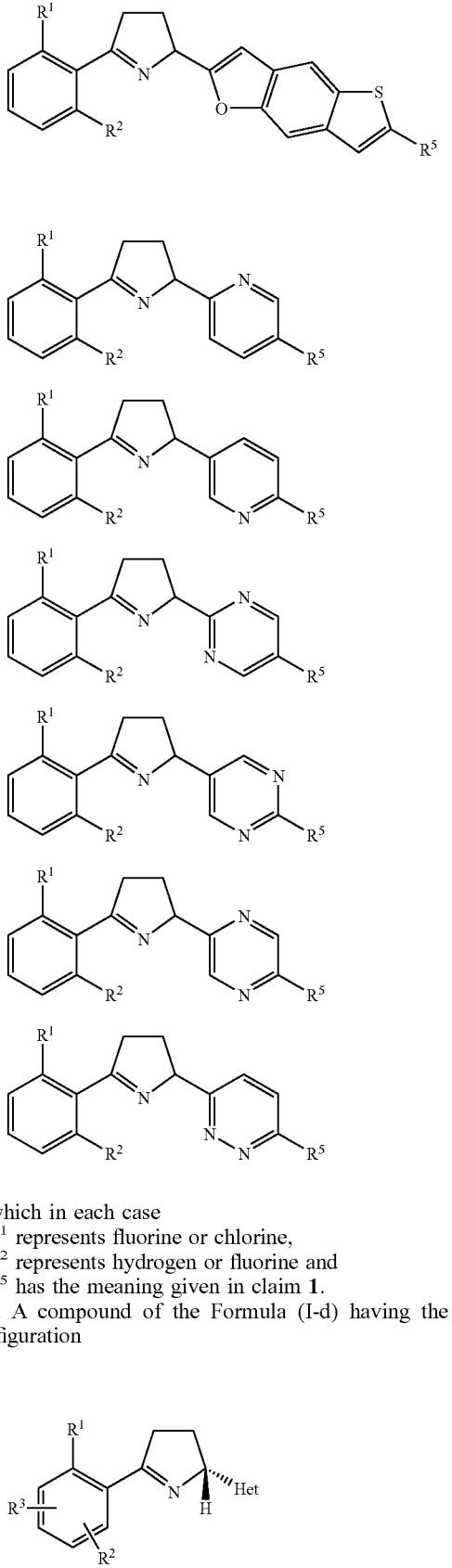
in which in each case
R¹ represents fluorine or chlorine,
R² represents hydrogen or fluorine and
R⁵ has the meaning given in claim 1.
8. A compound of the Formula (I-d) having the (R)-configuration in which R$^1$, R$^2$, R$^3$ and Het have the meanings given in claim 1.

9. The Δ$^1$ pyrroline of the Formula (I) according to claim 1 in which Het represents 2-thienyl, 3-thienyl, 2-thieno[3,2-b]-thienyl, 2-pyridinyl or 3-pyridinyl, each of which is optionally mono- or disubstituted by identical or different R$^5$.

10. The Δ$^1$ pyrroline of the Formula (I) according to claim 1 in which R$^1$ represents fluorine or chlorine, R$^2$ represents hydrogen or fluorine and R$^3$ represents hydrogen.

11. The Δ$^1$ pyrroline of the Formula (I) according to claim 1, in which R$^2$ represents hydrogen or fluorine, where R$^2$ is in the 6-position of the phenyl ring to which it is attached.

12. The Δ$^1$ pyrroline of the Formula (I) according to claim 1, in which X represents a direct bond and Y represents phenylene, preferably 1,4-phenylene.

13. The Δ$^1$ pyrroline of the Formula (I) according to claim 9, in which X represents a direct bond and Y represents phenylene, preferably 1,4-phenylene.

14. A process for preparing a compound of the Formula (I) according to claim 1, comprising A) treating an amino ketone of the Formula (II)

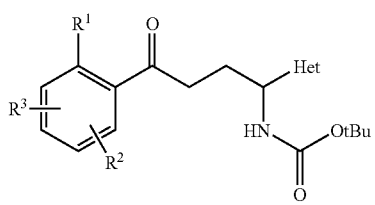

(II)

in which

R$^1$, R$^2$, R$^3$ and Het have the meanings given in claim 1 with a Lewis acid or a protonic acid, optionally in the presence of a diluent, or B) reacting an azide of the Formula (III)

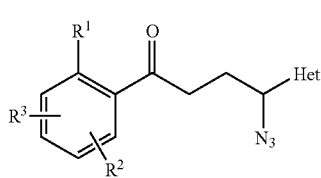

(III)

in which

R$^1$, R$^2$, R$^3$ and Het have the meanings given in claim 1 with a trialkylphosphine or a triarylphosphine or a trialkyl phosphite or a reducing agent in the presence of a diluent and, optionally in the presence of a catalyst, or C) reacting an amide of the Formula (IV)

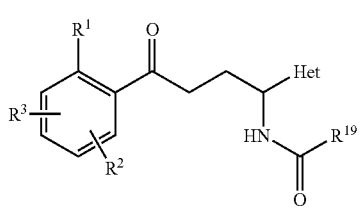

(IV)

in which

R$^{19}$ represents alkyl, halogenoalkyl, aryl or aralkyl and

R$^1$, R$^2$, R$^3$, Het have the meanings given in claim 1 with a N-deacetylating agent, optionally in the presence of a diluent, or to obtain a Δ$^1$-pyrroline of the Formula (I-a)

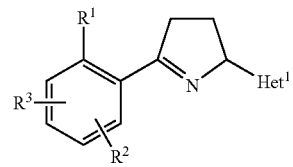

(I-a)

in which

Het$^1$ represents heteroaryl which is monosubstituted by R$^{5-1}$,

R$^{5-1}$ represents the grouping —Y$^1$-E,

Y$^1$ represents in each case optionally substituted phenylene or heterocyclylene and R$^1$, R$^2$, R$^3$ and E have the meanings given in claim 1

D) reacting a Δ$^1$-pyrroline of the Formula (I-b)

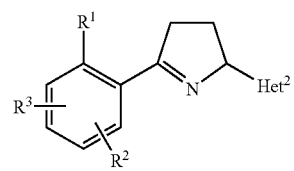

(I-b)

in which

Het$^2$ represents heteroaryl which is monosubstituted by R$^{5-2}$,

R$^{5-2}$ represents chlorine, bromine, iodine, —OSO$_2$CF$_3$ or —OSO$_2$(CF$_2$)$_3$CF$_3$, R$^1$, R$^2$ and R$^3$ have the meanings given in claim 1 with a(hetero)cycle of the Formula (V)

A$^1$-Y$^1$-E    (V)

in which

E has the meanings given in claim 1,

Y$^1$ has the meanings given above,

A$^1$ represents chlorine, bromine, iodine, —OSO$_2$CF$_3$ or —OSO$_2$(CF$_2$)$_3$CF$_3$, in the presence of a catalyst, in the presence of a diboronic ester and, optionally in the presence of an acid binder and, optionally, in the presence of a diluent, in a tandem reaction, or E) reacting a Δ$^1$-pyrroline of the Formula (VI)

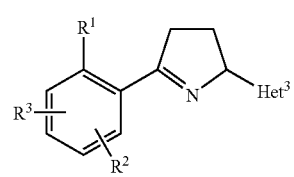

(VI)

in which
Het³ represents heteroaryl which is monosubstituted by A²,
A² represents -B(OH)₂, (4,4,5,5-tetramethyl-1,3,2-dioxaborolan)-2-yl, (5,5-dimethyl-1,3,2-dioxaborinan)-2-yl, (4,4,6-trimethyl-1,3,2-dioxaborinan)-2-yl or 1,3,2-benzodioxaborol-2-yl and
R¹, R² and R³ have the meanings given in claim 1 with a heterocycle of the Formula (V)

A¹-Y¹-E     (V)

in which
E has the meanings given in claim 1,
Y¹ and A¹ have the meanings given above,
in the presence of a catalyst, optionally in the presence of an acid binder and optionally in the presence of a diluent, or
F) reacting a Δ¹-pyrroline of the Formula (I-b)

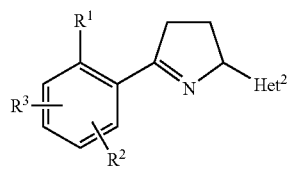

(I-b)

in which
R¹, R² and R³ have the meanings given in claim 1,
Het² has the meanings given above
with a boronic acid derivative of the Formula (VII)

A²-Y¹-E     (VII)

in which
E has the meanings given in claim 1,
Y¹ and A² have the meanings given above
in the presence of a catalyst, optionally in the presence of an acid binder and optionally in the presence of a diluent, or
G) reacting a Δ¹-pyrroline of the Formula (I-c)

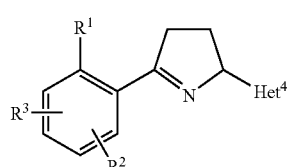

(I-c)

in which
Het⁴ represents heteroaryl which is monosubstituted by R⁵⁻³,
R⁵⁻³ represents bromine or iodine and
R¹, R² and R³ have the meanings given in claim 1 with an organometallic compound of the Formula (VIII)

M-Y¹-E     (VIII)

in which
E has the meanings given in claim 1,
Y¹ has the meanings given above,
M represents ZnCl, Sn(Me)₃ or Sn(n-Bu)₃
in the presence of a catalyst, optionally in the presence of an acid binder and optionally in the presence of a diluent.

15. A Δ¹ pyrroline of the Formula (I-d)

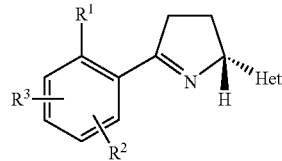

(I-d)

in which
R¹, R², R³ and Het have the meanings given in claim 1.

16. An aminoketone of the Formula (II)

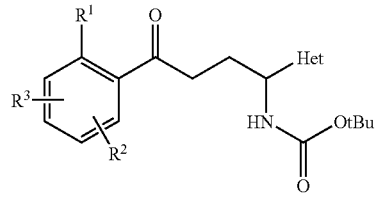

(II)

in which
R¹, R², R³ and Het have the meanings given in claim 1.

17. An azide of the Formula (III)

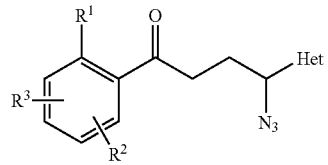

(III)

in which
R¹, R², R³ and Het have the meanings given in claim 1.

18. An amide of the Formula (IV)

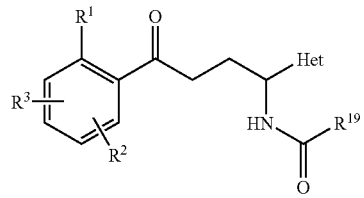

(IV)

in which
R¹⁹ represents alkyl, halogenoalkyl, aryl or arylalkyl and
R¹, R², R³ and Het have the meanings given in claim 1.

19. A lactam of the Formula (IX)

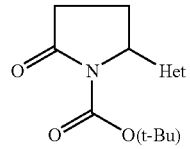

(IX)

in which

Het has the meanings given in claim 1.

20. A halide of the Formula (XV)

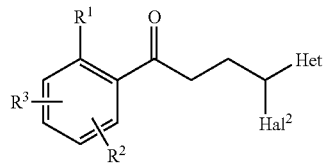

(XV)

in which

R$^1$, R$^2$, R$^3$ and Het have the meanings given in claim 1 and

Hal$^2$ represents halogen.

21. A pesticide comprising one or more compounds of the Formula (I) according to claim 1 and one or more extenders and/or surfactants.

22. A method for controlling pests, comprising allowing a compound of the Formula (I) according to claim 1 to act on pests and/or their habitat.

23. A process for preparing a pesticide comprising mixing a compound of the Formula (I) according to claim 1 with one or more extenders and/or surfactants.

* * * * *